(12) United States Patent
Kurimoto et al.

(10) Patent No.: US 6,329,381 B1
(45) Date of Patent: Dec. 11, 2001

(54) HETEROCYCLIC COMPOUNDS

(75) Inventors: Ayumu Kurimoto; Tetsuhiro Ogino; Hajime Kawakami, all of Nishinomiya (JP)

(73) Assignees: Sumitomo Pharmaceuticals Company, Limited, Osaka-fu; Japan Energy Corporation, Tokyo-to, both of (JP)

( * ) Notice: Subject to any disclaimer, the term of this patent is extended or adjusted under 35 U.S.C. 154(b) by 0 days.

(21) Appl. No.: 09/555,292

(22) PCT Filed: Nov. 26, 1998

(86) PCT No.: PCT/JP98/05318

§ 371 Date: May 26, 2000

§ 102(e) Date: May 26, 2000

(87) PCT Pub. No.: WO99/28321

PCT Pub. Date: Jun. 10, 1999

(30) Foreign Application Priority Data

| Nov. 28, 1997 | (JP) | 9-347422 |
| Dec. 11, 1997 | (JP) | 9-367451 |
| Dec. 17, 1997 | (JP) | 9-367449 |

(51) Int. Cl.[7] ............... C07D 473/16; C07D 473/18; C07D 473/24; A61K 31/522; A61P 37/01
(52) U.S. Cl. ............................................. 514/262
(58) Field of Search ........................ 514/262; 544/276

(56) References Cited

U.S. PATENT DOCUMENTS 6,028,076  2/2000  Hirota et al. .

FOREIGN PATENT DOCUMENTS

| 201289A2 | 11/1986 | (EP) . |
| 61-277686 | 12/1986 | (JP) . |
| 8-165292 | 6/1996 | (JP) . |
| WO9817279 | 4/1998 | (JP) . |

OTHER PUBLICATIONS

"Field Virology, Third Ed.", B. N. Fields et al eds., Lippincott–Raven, Philadelphia, 1996, p. 431.*
Testerman et al—"Journal of Leukocyte Biology", vol. 58, 365–372 (1995.)
Stringfellow—"Methods in Enzymology", vol. 78, 262–284 (1981).
Good et al., The Journal of Pharmacology and Experimental Therapeutics, vol. 227, No. 3, pp. 644–651.

* cited by examiner

Primary Examiner—Mukund J. Shah
Assistant Examiner—Thomas C McKenzie
(74) Attorney, Agent, or Firm—Birch, Stewart, Kolasch & Birch, LLP

(57) ABSTRACT

The present invention relates to a heterocyclic compound of the following general formula (I):

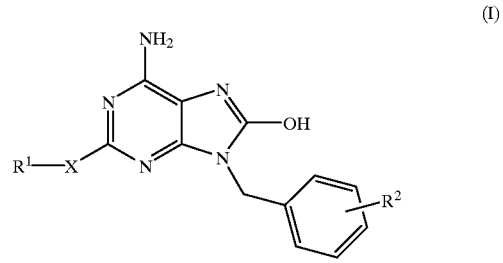

wherein X is sulfur atom, oxygen atom or —NR$^3$— (R$^3$ may form a heterocyclic ring or a substituted heterocyclic ring with R$^1$ via the nitrogen atom), R$^1$ is alkyl group, substituted alkyl group, aryl group, substituted aryl group, heterocyclic group or substituted heterocyclic group, and R$^2$ is hydrogen atom, halogen atom etc.;

or its pharmaceutically acceptable salt and interferon inducers, antiviral agents, anticancer agents and therapeutic agents for immunologic diseases comprising the compound (I) or its pharmaceutically acceptable salt as active ingredients.

13 Claims, No Drawings

HETEROCYCLIC COMPOUNDS

This application is the national phase under 35 U.S.C. §371 of PCT International Application No. PCT/JP98/05318 which has an International filing date of Nov. 26, 1998, which designated the United States of America.

TECHNICAL FIELD

The present invention relates to novel heterocyclic compounds having inducing activity for biosynthesis of interferon. The heterocyclic compounds of the present invention induce biosynthesis of endogenous interferon in a living body, and are useful for medicines, such as antiviral agents, anticancer agents and therapeutic agents for immunologic diseases.

BACKGROUND OF THE ART

It has been recently determined that endogenous interferon plays not only central role to bio-defensive mechanism against virus infections and microbial infections, but also an important role dn antitumor and immune modulator. Mass production of interferon is established. Namely, it is possible to obtain of natural interferon by cell culture and also to produce a large amount of recombinant interferon from *E. coli* transferred with a gene of interferon and therefore, many research achievements on these interferons have accumulated. For example, many kinds of biological activity on interferon, such as antiviral activity, prevention of cell growth and immune modulation have been confirmed and interferon is practiced on clinics as treating agents for virus infected diseases, such as hepatitis C and hepatitis B, anticancer agents and therapeutic agents for immunologic disease. Furthermore, it is suggested that interferon will prevent carcinogenesis by hepatitis C and hepatitis B.

Since there is no therapeutic method for almost of the above diseases, interferon is especially made much of.

DISCLOSURE OF INVENTION

The object of the present invention is to provide novel low molecular weight compounds having inducing activity for biosynthesis of interferon, and interferon inducers, antiviral agents, anticancer agents and therapeutic agents for immunologic diseases comprising these compounds as active ingredients.

Viruses of many kinds of animals, microbes such as mycobacteria and protozoa, extracts of them, mitogen, specific antigens and immunopotenciators are known as inducers for biosynthesis of interferon. It is known that for example, many kinds of natural double strand RNAS, synthesized double strand RNAs such as poly-I:C, and anionic high molecular compounds such as polyacrylic acid and oxyamylose oxidized with chlorite have inductive activity of interferon.

On the other hand, among low molecular weight compounds have been found fluorenones, pyrimidine derivatives, anthraquinones, acridines and so on having inductive activity of interferon (Stringfollow, D. A.: Methods in Enzymology, 1981, 78, 262).

However, when these compounds are used in clinical trial, their inducing activity of interferon is unexpectedly low and these compounds have side effects or by administering them repeatedly, their inducing activity of interferon decreases and therefore, development on these compounds has not succeeded. Furthermore, imidazo-quinolines are known as interferon inducers among low molecular compounds. However, it is known that these compounds are inferior in selective interferon inducing activity and simultaneously induce cytokines such as IL-6, TNF-α, etc (Testerman, T. L., et al.: J. Leukocyte Biol., 1995, 58, 365).

As the result of extensive investigation of interferon biosynthesis inducers among low molecules, the present inventors have found that the heterocyclic compounds of the present invention have excellent interferon biosynthesis inducing activity.

The present invention relates to a heterocyclic compound of the following general formula (I):

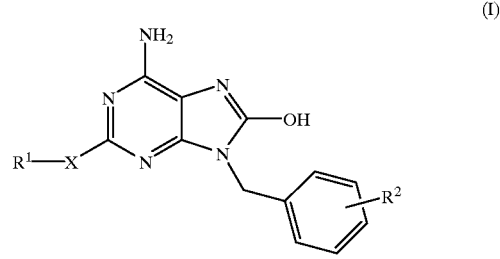

(I)

wherein X is sulfur atom, oxygen atom, —$NR^3$— (in which $R^3$ is hydrogen atom, alkyl group or substituted alkyl, or may form a heterocyclic ring or a substituted heterocyclic ring together with $R^1$ via the nitrogen atom), $R^1$ is alkyl group, substituted alkyl group, aryl group, substituted aryl group, heterocyclic group or substituted heterocyclic group, and $R^2$ is hydrogen atom, or one or more substituents on the benzene ring, and said substituent is the same or different and is hydroxy group, lower alkyl group, substituted lower alkyl group, lower alkoxy group, substituted lower alkoxy group, lower alkanoyl group, substituted lower alkanoyl group, aroyl group, substituted aroyl group, carboxyl group, lower alkoxycarbonyl group, substituted lower alkoxycarbonyl group, amino group, lower alkylamino group, di(lower alkyl)amino group, carbamoyl group, lower alkylcarbamoyl group, di(lower alkyl)carbamoyl group, halogen atom, nitro group or cyano group; or a pharmaceutically acceptable salt thereof.

Further, the present invention relates to a pharmaceutical composition comprising a heterocyclic compound of the above formula (I) or its pharmaceutically acceptable salt as an active ingredient.

Further, the present invention relates to an interferon inducer, an antiviral agent, an anticancer agent and a therapeutic agent for immunologic diseases comprising a heterocyclic compound of the above formula (I) or its pharmaceutically acceptable salt as an active ingredient.

Furthermore, the present invention relates to a process for preparing a heterocyclic compound of the above formula (I) or its pharmaceutically acceptable salt.

Groups $R^1$, $R^2$ and $R^3$ in the formula (I) are explained below.

In $R^1$ alkyl group includes straight or branched $C_{1-10}$ alkyl group (e.g. methyl, ethyl, propyl, butyl, pentyl, isopropyl, isobutyl, 1-methylpropyl, 3-methylbutyl or hexyl), $C_{3-7}$ cycloalkyl group (e.g. cyclopropyl, cyclopentyl, cyclohexyl or cycloheptyl), and alkyl-substituted $C_{3-7}$ cycloalkyl group, preferably straight or branched $C_{1-6}$ alkyl group (e.g. methyl, ethyl, propyl, butyl or pentyl), and $C_{5-7}$ cycloalkyl group (e.g. cyclopentyl or cyclohexyl).

In $R^1$ substituted alkyl group means the above alkyl substituted by the same or different and one or more substituents.

Said substituents include cycloalkyl group ($C_{3-6}$ cycloalkyl group, such as cyclopropyl, cyclopentyl or cyclohexyl), hydroxy group, lower alkoxy group ($C_{1-6}$ alkoxy such as methoxy, ethoxy, propoxy, butoxy or pentoxy), substituted lower alkoxy group (substituted $C_{1-6}$ alkoxy group, such as methoxyethoxy, ethoxyethoxy, hydroxyethoxy or chloroethoxy), amino group, alkylamino group, cyano group, nitro group, acyl group, carboxyl group, lower alkoxycarbonyl group ($C_{2-7}$ alkoxycarbonyl group, such as methoxycarbonyl or ethoxycarbonyl), halogen atom, such as fluorine atom, chlorine atom or bromine atom, mercapt group, lower alkylthio group ($C_{1-6}$ alkylthio group, such as methylthio, ethylthio, propylthio or butylthio), substituted lower alkylthio group (substituted $C_{1-6}$ alkylthio group, such as methoxyethylthio, methylthioethylthio, hydroxyethylthio or chloroethylthio), aryl group ($C_{6-10}$ monocyclic or fused cyclic aryl group, such as phenyl or naphthyl), substituted aryl group (substituted $C_{6-10}$ monocyclic or fused cyclic aryl group, such as 4-hydroxyphenyl, 4-methoxyphenyl, 4-fluorophenyl, 4-chlorophenyl or 3,4-dichlorophenyl), and heterocyclic group (5–6 membered saturated heterocyclic group containing nitrogen atoms from 0–2 and oxygen atoms from 0–2, such as piperidyl, piperazinyl, morpholinyl, tetrahydrofuranyl, pyrrolidinyl, pyrazolinyl or 1,3-dioxolanyl, 5–6 membered unsaturated heterocyclic group, such as furyl, pyrrolyl, pyrazolyl, imidazolyl, thiazolyl, thienyl, pyridyl or pyrimidinyl, or bicyclic unsaturated heterocyclic group, such as indolyl, isoindolyl, quinolyl, benzothiazolyl, chromanyl, benzofuranyl or phthalimino).

In $R^1$ aryl group means $C_{6-10}$ monocyclic or fused cyclic aryl group, such as phenyl or naphthyl.

In $R^1$ substituted aryl group means the above aryl group substituted by the same or different and one or more substituents.

Said substituent includes lower alkyl group ($C_{1-6}$ alkyl group, such as methyl, ethyl, propyl, butyl, cyclopentyl or cyclohexyl), hydroxy lower alkyl group (hydroxy $C_{1-6}$ alkyl group, such as hydroxymethyl, 2-hydroxyethyl or 3-hydroxypropyl), lower alkoxy lower alkyl group ($C_{1-6}$ alkoxy $C_{1-6}$ alkyl group, such as 2-methoxyethyl, 2-ethoxyethyl or 3-methoxypropyl), hydroxy group, lower alkoxy group ($C_{1-6}$ alkoxy group such as methoxy, ethoxy, propoxy, butoxy or pentoxy), cyano group, amino group, substituted amino group, lower alkoxycarbonyl group ($C_{2-7}$ alkoxycarbonyl group, such as methoxycarbonyl, ethoxycarbonyl or propoxycarbonyl), acyl group, nitro group, halogen atom, such as fluorine atom, chlorine atom or bromine atom, aryl group ($C_{6-10}$ monocyclic or fused cyclic aryl group, such as phenyl or naphthyl), substituted aryl group (substituted $C_{6-10}$ monocyclic or fused cyclic aryl group, such as 4-hydroxyphenyl, 4-methoxyphenyl, 4-chlorophenyl or 3,4-dichlorophenyl), and heterocyclic group (alicyclic or aromatic heterocyclic group containing nitrogen atoms from 1–2 and oxygen atom from 0–1, such as pyrrolidinyl, piperidyl, piperazinyl or morpholinyl).

In $R^1$ heterocyclic group means monocyclic saturated heterocyclic group, or unsaturated monocyclic or fused heterocyclic group containing at least one heteroatom, that is, 0–3 nitrogen atoms, 0–1 oxygen atom and 0–1 sulfur atom.

Said saturated monocyclic heterocyclic group includes 5 or 6 membered saturated heterocyclic group, such as tetrahydrofuranyl, pyrrolidinyl, morpholinyl, piperidyl, piperazinyl or pyrazolidinyl. Said unsaturated monocyclic heterocyclic group means 5 or 6 membered unsaturated heterocyclic group, such as furyl, pyrrolyl, pyrazolyl, imidazolyl, thiazolyl, thienyl, pyridyl or pyrimidinyl. Said unsaturated fused heterocyclic group means unsaturated bicyclic heterocyclic group, such as indolyl, isoindolyl, quinolyl, benzothizolyl, chromanyl or benzofuranyl.

In $R^1$ substituted heterocyclic group means the above heterocyclic group substituted by the same or different and one or more substituents.

Said substituents include lower alkyl group ($C_{1-6}$ alkyl group, such as methyl, ethyl, propyl, butyl, cyclopentyl or cyclohexyl), hydroxy lower alkyl group (hydroxy $C_{1-6}$ alkyl group, such as hydroxymethyl, 2-hydroxyethyl or 3-hydroxypropyl), lower alkoxy lower alkyl group ($C_{1-6}$ alkoxy $C_{1-6}$ alkyl group, such as 2-methoxyethyl, 2-ethoxyethyl or 3-methoxypropyl), hydroxy group, lower alkoxy group ($C_{1-6}$ alkoxy group such as methoxy, ethoxy, propoxy, butoxy or pentoxy), cyano group, nitro group, halogen atom, such as fluorine atom, chlorine atom or bromine atom, amino group, substituted amino group, lower alkoxycarbonyl group ($C_{2-7}$ alkoxycarbonyl group, such as methoxycarbonyl, ethoxycarbonyl or propoxycarbonyl), acyl group, aryl group ($C_{6-10}$ monocyclic or fused cyclic aryl group, such as phenyl or naphthyl), substituted aryl group (substituted $C_{6-10}$ monocyclic or fused cyclic aryl group, such as 4-hydroxyphenyl, 4-methoxyphenyl, 4-chlorophenyl or 3,4-dichlorophenyl), and heterocyclic group (alicyclic or aromatic heterocyclic group containing nitrogen atoms from 1–2 and oxygen atom from 0–1, such as pyrrolidinyl, piperidyl, piperazinyl or morpholinyl).

In $R^2$ lower alkyl group includes $C_{1-6}$ alkyl group (e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl).

In $R^2$ substituted lower alkyl group means the above alkyl substituted by the same or different and one or more substituents.

Said substituents include hydroxy group, lower alkoxy group (for example, $C_{1-6}$ alkoxy group, such as methoxy, ethoxy or propoxy), carboxyl group, lower alkoxycarbonyl group (for example, $C_{2-7}$ alkoxycarbonyl group, such as methoxycarbonyl, ethoxycarbonyl or propoxycarbonyl) and halogen atom, such as fluorine atom, chlorine atom or bromine atom.

In $R^2$ lower alkoxy group means $C_{1-6}$ alkoxy group, such as methoxy, ethoxy or propoxy.

In $R^2$ substituted lower alkoxy group means the above alkoxy group substituted by the same or different and one or more substituents.

Said substituents include hydroxy group, lower alkoxy group ($C_{1-6}$ alkoxy group, such as methoxy, ethoxy or propoxy), carboxyl group, lower alkoxycarbonyl group ($C_{2-7}$ alkoxy-carbonyl group, such as methoxycarbonyl, ethoxycarbonyl group or propoxycarbonyl) and halogen atom, such as fluorine atom, chlorine atom or bromine atom.

In $R^2$ lower alkanoyl group means $C_{1-6}$ alkanoyl group, such as formyl, acetyl, propanoyl, butanoyl, pentanoyl or hexanoyl.

In $R^2$ substituted lower alkanoyl group means the above alkanoyl group substituted by the same or different and one or more substituents.

Said substituents include hydroxy group, lower alkoxy group ($C_{1-6}$ alkoxy group, such as methoxy, ethoxy or propoxy), carboxyl group, lower alkoxycarbonyl group ($C_{2-7}$ alkoxycarbonyl group, such as methoxycarbonyl or propoxycarbonyl) and halogen atom, such as fluorine atom, chlorine atom or bromine atom.

In $R^2$ aroyl group means $C_{7-11}$ aroyl group, such as benzoyl or naphthoyl.

In $R^2$ substituted aroyl group means the above aroyl group substituted by the same or different and one or more substituents.

Said substituents include hydroxy group, lower alkoxy group ($C_{1-6}$ alkoxy group, such as methoxy, ethoxy or propoxy), carboxyl group, lower alkoxycarbonyl group ($C_{2-7}$ alkoxycarbonyl group, such as methoxycarbonyl, ethoxycarbonyl or propoxycarbonyl) and halogen atom, such as fluorine atom, chlorine atom or bromine atom.

In $R^2$ lower alkoxycarbonyl group means $C_{2-7}$ alkoxycarbonyl group, such as methoxycarbonyl, ethoxycarbonyl or propoxycarbonyl.

In $R^2$ substituted lower alkoxycarbonyl group means the above alkoxycarbonyl group substituted by the same or different and one or more substituents.

Said substituents include hydroxy group, lower alkoxy group ($C_{1-6}$ alkoxy group, such as methoxy, ethoxy or propoxy), carboxyl group, lower alkoxycarbonyl group ($C_{2-7}$ alkoxycarbonyl group, such as methoxycarbonyl, ethoxycarbonyl or propoxycarbonyl) and halogen atom, such as fluorine atom, chlorine atom or bromine atom.

In $R^2$ lower alkylamino group means amino group substituted by $C_{1-6}$ alkyl group (e.g. methylamino, ethylamino, propylamino, butylamino).

In $R^2$ di(lower alkyl)amino group means amino group substituted by the same or different and $C_{1-6}$ alkyl group (e.g. dimethylamino, diethylamino, ethylmethylamino).

In $R^2$ lower alkylcarbamoyl group means carbamoyl group substituted by $C_{1-6}$ alkyl group (e.g. methylcarbamoyl, ethylcarbamoyl, propylcarbamoyl, butylcarbamoyl).

In $R^2$ di(lower alkyl)carbamoyl group means carbamoyl group substituted by the same or different and $C_{1-6}$ alkyl group (e.g. dimethylcarbamoyl, diethylcarbamoyl, ethylmethylcarbamoyl).

In $R^2$ halogen atom means halogen atom such as fluorine atom, chlorine atom, bromine atom or iodine atom.

In $R^3$ alkyl group includes straight or branched $C_{1-10}$ alkyl group (e.g. methyl, ethyl, propyl, butyl, pentyl, hexyl) and $C_{3-7}$ cycloalkyl group (e.g. cyclopropyl, cyclopentyl, cyclohexyl, cycloheptyl), preferably straight or branched $C_{1-6}$ alkyl group (e.g. methyl, ethyl, propyl, butyl, pentyl), and $C_{5-7}$ cycloalkyl group (e.g. cyclopentyl, cyclohexyl).

In $R^3$ substituted alkyl group means the above alkyl group substituted by the same or different and one or more substituents.

Said substituents include cycloalkyl group ($C_{3-6}$ cycloalkyl group, such as cyclopropyl, cyclopentyl or cyclohexyl), hydroxy group, lower alkoxy group ($C_{1-6}$ alkoxy, such as methoxy, ethoxy, propoxy, butoxy or pentoxy), amino group, cyano group, aryl group such as phenyl, substituted aryl group, such as 4-hydroxyphenyl, 4-methoxyphenyl, 4-chlorophenyl or 3,4-dichlorophenyl, nitro group and halogen atom, such as fluorine atom, chlorine atom or bromine atom.

Heterocyclic ring formed together with $R^3$ and $R^1$ via the nitrogen atom means 5 or 6 membered saturated heterocyclic ring, such as 1-pyrrolidinyl, 4-morpholinyl, 1-piperidyl, 1-piperazinyl or 1-pyrazolidinyl, and 5 or 6 membered unsaturated heterocyclic ring such as 1-imidazolyl.

Substituted heterocyclic ring formed together with $R^3$ and $R^1$ via the nitrogen atom means the above heterocyclic ring formed together with $R^3$ and $R^1$ via the nitrogen atom alkyl substituted by the same or different and one or more substituents.

Said substituents include lower alkyl group ($C_{1-6}$ alkyl group, such as methyl, ethyl, propyl, butyl, cyclopentyl or cyclohexyl), hydroxy lower alkyl group (hydroxy $C_{1-6}$ alkyl, such as hydroxymethyl, 2-hydroxyethyl or 3-hydroxypropyl), lower alkoxy lower alkyl group ($C_{1-6}$ alkoxy $C_{1-6}$ alkyl, such as 2-methoxyethyl, 2-ethoxyethyl or 3-methoxypropyl), hydroxy group, lower alkoxy group ($C_{1-6}$ alkoxy, such as methoxy, ethoxy, propoxy, butoxy or pentoxy) and cyano group.

The compound (I) of the present invention forms an equilibrium mixture with a tautomer represented by the following formula (Ia):

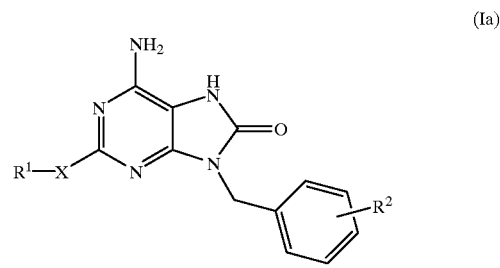

(Ia)

The compound (I) of the present invention may forms a salt with an acid.

The preferable acids are pharmaceutically acceptable acids, including inorganic acids, such as hydrochloric acid, sulfuric acid, hydrobromic acid, etc., organic acids, such as acetic acid, oxalic acid, citric acid, malic acid, tartaric acid, fumaric acid, maleic acid, etc.

Further, in case of the compound (I) having an acidic substituent, the compound may form a salt with a base.

The preferable bases are pharmaceutically acceptable bases, including inorganic bases like alkali metals, such as sodium or potassium, or organic bases, such as triethylamine or pyridine.

Preferable embodiments among the compounds (I) of the present invention are as follows.

(a) A heterocyclic compound of the formula (II):

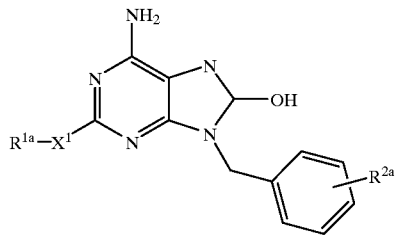

(II)

wherein $X^1$ is sulfur atom, oxygen atom or —$NR^{3a}$— in which $R^{3a}$ is hydrogen, $C_{1-6}$ alkyl group, or substituted $C_{1-6}$ alkyl group, or may form a heterocyclic ring or a substituted heterocyclic ring together with $R^{1a}$ via the nitrogen atom, $R^{1a}$ is $C_{1-6}$ alkyl group, substituted $C_{1-6}$ alkyl group, aryl group, substituted aryl group, heterocyclic group or substituted heterocyclic group, and $R^{2a}$ is hydrogen atom, or one or more substituents on the benzene ring, and said substituent is the same or different and is halogen atom, $C_{1-6}$ alkoxy group, nitro group or hydroxy group; or its pharmaceutically acceptable salt.

(b) A heterocyclic compound of the above (a) wherein $X^1$ is sulfur atom.

(c) A heterocyclic compound of the above (a) wherein $X^1$ is oxygen atom.

(d) A heterocyclic compound of the above (a) wherein $X^1$ is —NH—.

(e) A heterocyclic compound of the above (a) wherein $X^1$ is —$NR^{3a}$— in which $R^{3a}$ means $C_{1-6}$ alkyl group or substituted $C_{1-6}$ alkyl group.

(f) A heterocyclic compound of the above (a) wherein $R^{3a}$ forms a heterocyclic ring or a substituted heterocyclic ring together with $R^{1a}$ via the nitrogen atom.

(g) A heterocyclic compound of any of the above (a)–(d) wherein $R^{1a}$ means $C_{1-6}$ alkyl group or substituted $C_{1-6}$ alkyl group.

(h) A heterocyclic compound of any of the above (a)–(d) wherein $R^{1a}$ means $C_{1-6}$ alkyl group substituted by $C_{1-6}$ alkoxy, hydroxy, halogen atom, cyano, trifluoromethyl, pyridyl, phenyl, tolyl or thienyl.

(i) A heterocyclic compound of any of the above (a)–(d) wherein $R^{1a}$ means $C_{1-6}$ alkyl group.

(j) A heterocyclic compound of any of the above (a)–(d) wherein $R^{1a}$ means $C_{3-6}$ cycloalkyl group.

(k) A pharmaceutically acceptable salt of a heterocyclic compound of any of the above (b)–(j).

The compound (I) of the present invention has excellent inducing activity for biosynthesis of interferon and shows in general the following structure activity-relationship between $R^1$ and $R^2$ of the compound (I).

The inducing activity for biosynthesis of the compound (I) of the present invention is influenced by length or size of $R^1$. For instance, the activity at the minimum concentration reaches best when carbon number on the group of $R^1$ is around 3 or 4 and therefore, it shows bell-type activity-relationship.

On the other hand, although the activity at the minimum concentration when carbon number on the group of $R^1$ is around 1 or 2 is inferior to the activity when carbon number on the group of $R^1$ is around 3 or 4, the former is superior to the latter in induction amount of interferon judging from the view of the production of interferon.

Therefore, when $R^1$ is alkyl group, preferable range of carbon number in the view of the activity is 1 to 8, more preferably 3 to 5.

Preferable embodiments of alkyl group in $R^1$ are methyl, ethyl, propyl, butyl, pentyl, isopropyl, isobutyl, 1-methylpropyl, 3-methylbutyl, cyclopentyl and cyclohexyl.

Furthermore, it has been made clear that in case that $R^1$ is substituted alkyl group, the activity is also influenced by size or length of $R^1$.

That is, the activity is influenced by total size or length of $R^1$ including a substituent (e.g. lower alkoxy, hydroxy, halogen atom). For instance, preferable range of length in the view of the activity is 1 to 8, more preferably 3 to 5 by calculating in carbon number as the same as in alkyl group in $R^1$.

Preferable embodiment of alkyl group in $R^1$ are 2-hydroxyethyl, 3-hydroxypropyl, 4-hydroxybutyl, 2-aminoethyl, 3-aminopropyl, 4-aminobutyl, methoxymethyl, 2-methoxyethyl, 3-methoxypropyl, ethoxymethyl, 2-ethoxyethyl, methylthiomethyl, 2-methylthioethyl, 3-methylthiopropyl, 2-fluoroethyl, 3-fluoropropyl, 2,2,2-trifluoroethyl, cyanomethyl, 2-cyanoethyl, 3-cyanopropyl, methoxycarbonylmethyl, 2-methoxycarbonylethyl, 3-methoxycarbonylpropyl, benzyl, phenethyl, 4-pyridylmethyl, cyclohexylmethyl, 2-thienylmethyl, 4-methoxyphenylmethyl, 4-hydroxyphenylmethyl, 4-fluorophenylmethyl, and 4-chlorophenylmethyl.

When $R^1$ is aryl group or substituted aryl group, the same tendency as above is observed. The most preferable embodiment of aryl group or substituted aryl group in $R^1$ are phenyl, 4-methoxyphenyl, 4-hydroxyphenyl, 4-fluorophenyl and 4-chlorophenyl.

When $R^1$ is heterocyclic group or substituted heterocyclic group, or $R^3$ forms heterocyclic ring or substituted heterocyclic ring with $R^1$, the same tendency as above is also observed. The most preferable embodiments of heterocyclic group or substituted heterocyclic group in $R^1$ are 1-pyrrolidinyl, 4-morpholinyl and 3-(2-hydroxyethyl)-1-pyrrolidinyl.

Preferable X are sulfur atom, oxygen atom and nitrogen atom which may be substituted, in order.

Although influence by $R^2$ on inducing activity for biosynthesis of interferon is not so remarkable as that by $R^1$, preferable embodiments of $R^2$ are hydrogen atom, halogen atom such as fluorine atom or chlorine atom, hydroxy group, lower alkoxy group such as methoxy, and nitro group.

A preferable substituent of $R^2$ and its position among the above embodiments is 4-fluoro, 4-chloro, 4-hydroxy, 4-methoxy, 4-nitro, 2,4-difluoro, 2,4-dichloro, 3,4-difluoro, 3,4-dichloro, or 3,4-dimethoxy.

Process for preparation of the compound of the present invention.

The compound of the present invention can be prepared by the following methods. However, starting materials which are not described below are prepared in accordance with the following methods, known methods, or in accordance with known methods.

PROCESS 1

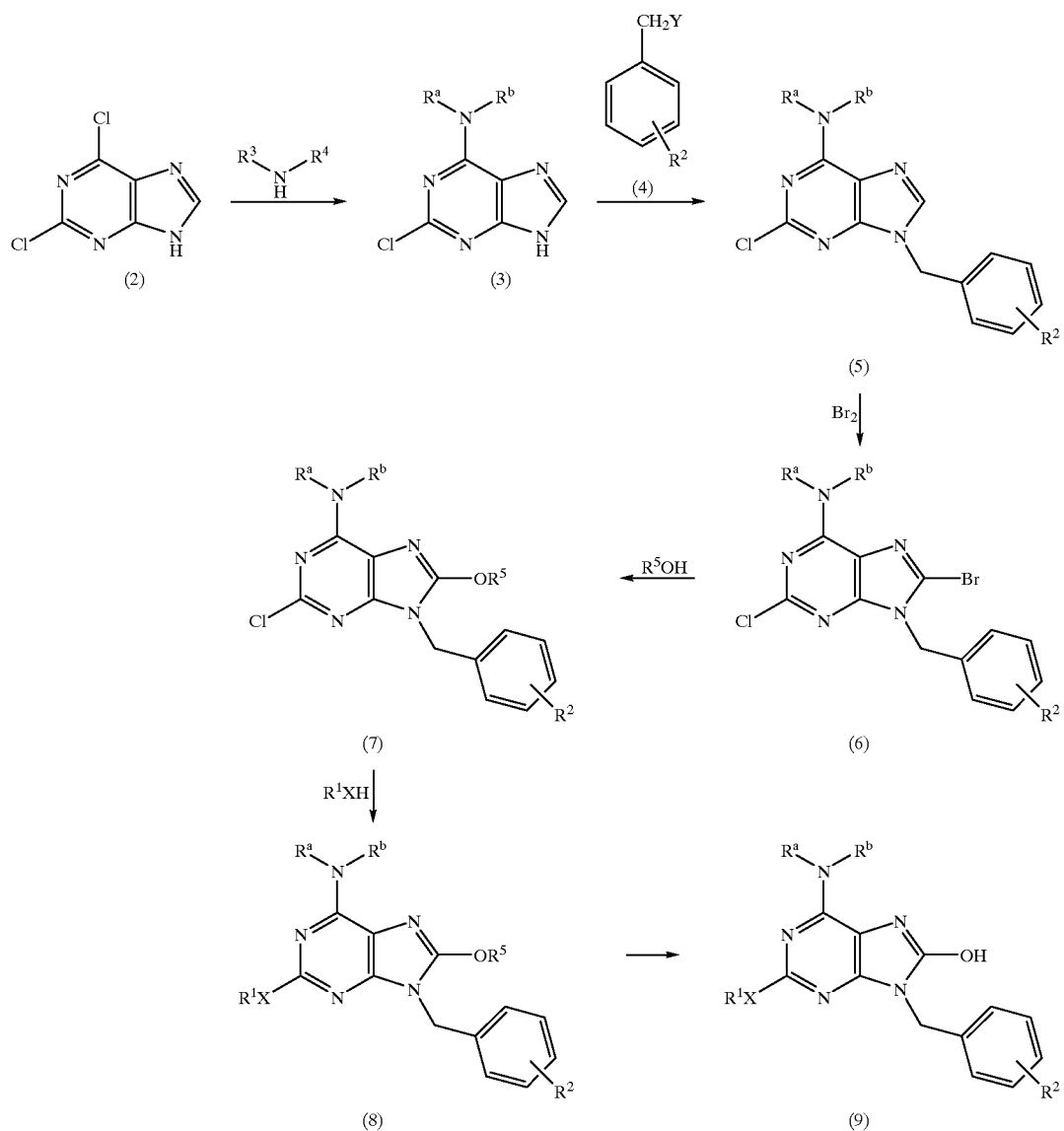

wherein $R^1$, X and $R^2$ are the same as definition in the formula (I), Y is leaving group such as halogen atom (e.g. chlorine atom, bromine atom), $R^5$ is alkyl group, and $R^a$ and $R^b$ are hydrogen atom, or mean amino protective group because they are protected by an amino protective group on the way of reaction, if necessary.

Compound (3) is prepared by reacting compound (2) with $NHR^aR^b$ in an aqueous solution or in an organic solvent.

$NHR^aR^b$ can be used about equal molar or large excess amount to compound (2).

Organic solvents are alcohols, such as methanol, ethanol, propanol or butanol, ethers such as tetrahydrofuran, 1,4-dioxane or diglyme, or aprotic solvents, such as dimethylformamide, dimethyl sulfoxide, acetonitrile or hexamethylphosphoroustriamide $[(CH_3)_2N)_3P]$.

The reaction temperature is selected from the range between room temperature and about 200° C.

Reaction vessels such as an autoclave etc. may be used in the reaction, if necessary.

Compound (5) is prepared by reacting compound (3) and compound (4) in the presence of a base in an organic solvent.

Compound (4) can be used about equal molar or several molars to compound (3).

Bases are inorganic bases such as alkali metal carbonates (e.g. sodium carbonate, potassium carbonate), or organic bases, such as tertiary amines (e.g. triethylamine, diisopropylethylamine) or pyridines (e.g. 4-dimethylaminopyridine, pyridine). The base is preferably used about equimolar to compound (4)

The organic solvents are halogenated hydrocarbons such as tetrachloromethane, chloroform or methylene chloride, ethers such as diethyl ether, tetrahydrofuran or 1,4-dioxane, or aprotic solvents, such as dimethylformamide, dimethyl sulfoxide, acetonitrile or hexamethylphosphoroustriamide.

The reaction temperature is selected from the range between about 0° C. and around the boiling point of the solvent.

Compound (6) is prepared by reacting compound (5) with $Br_2$ in an organic solvent.

A reaction promoter such as sodium acetate may be added to the reaction mixture.

Br$_2$ is used from equimolar to several moles of compound (5), preferably from equimolar to one and one-half moles.

The organic solvents are halogenated hydrocarbons, such as tetrachloromethane, chloroform or methylene chloride, ethers, such as diethyl ether, acetic acid, or carbon disulfide.

The reaction temperature is selected from the range between about 0° C. and around boiling point of the solvent.

Compound (7) is prepared by reacting compound (6) and an alcohol such as methanol in the presence of a base in an organic solvent.

The base are alkali metals, such as sodium or potassium, alkali metal hydrides, such as sodium hydride or potassium hydride, organometallic compounds, such as methyl lithium, butyl lithium or lithium diisopropylamide.

The base is preferably used from about equal molar to about two times as much to compound (6).

The organic solvents are ethers, such as diethyl ether, tetrahydrofuran or 1,4-dioxane, or aprotic solvents, such as dimethylformamide, dimethyl sulfoxide, acetonitrile or hexamethylphosphoroustriamide. The alcohol as the reagent, such as methanol, ethanol, propanol or butanol may serve as a solvent.

The reaction temperature is selected from the range between about room temperature and around boiling point of the solvent.

Compound (8) is prepared by reacting compound (7) with R$^1$XH in an organic solvent.

R$^1$XH is used from about equal molar to several molars to compound (7).

When X is oxygen atom or sulfur atom, the reaction is preferably carried out in the presence of a base.

The bases are alkali metals, such as sodium or potassium, alkali metal hydrides, such as sodium hydride or potassium hydride, organometalic compounds, such as methyl lithium, butyl lithium or lithium diisopropylamide. The base is preferably used about equimolar to R$^1$XH.

The organic solvents are aprotic solvents, such as dimethylformamide, acetonitrile or hexamethylphosphoroustriamide, or ethers such as diethyl ether, tetrahydrofuran or 1,4-dioxane or diglyme.

The reaction temperature is selected from the range between about room temperature and around the boiling point of the solvent.

Compound (9) is prepared by treating compound (8) with an acid in water or a mixture of water and an organic solvent.

The acids are inorganic acids, such as hydrochloric acid or hydrobromic acid, or organic acids such as trifluoroacetic acid.

The organic solvents are ethers, such as diethyl ether or tetrahydrofuran, aprotic solvents such as dimethylformamide, alcohols, such as methanol, ethanol or propanol, or acetic acid.

The reaction temperature is selected from the range between about room temperature and around boiling point of the solvent.

PROCESS 2

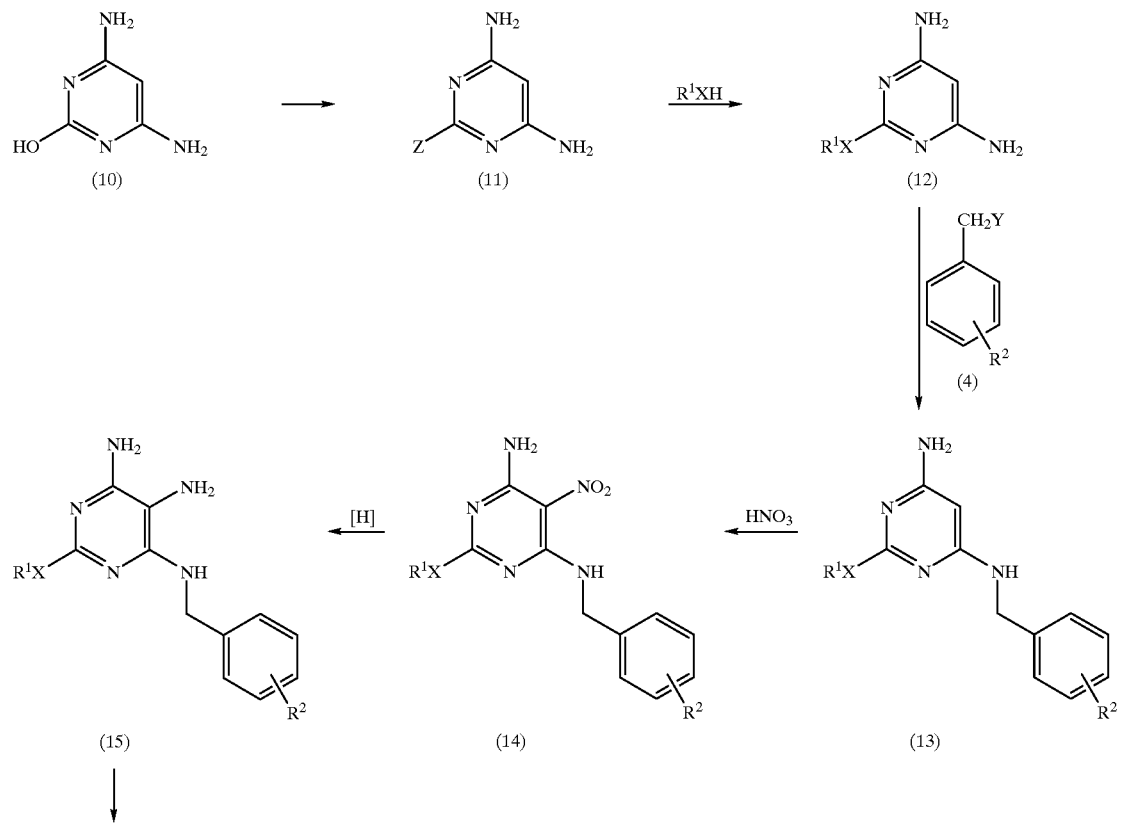

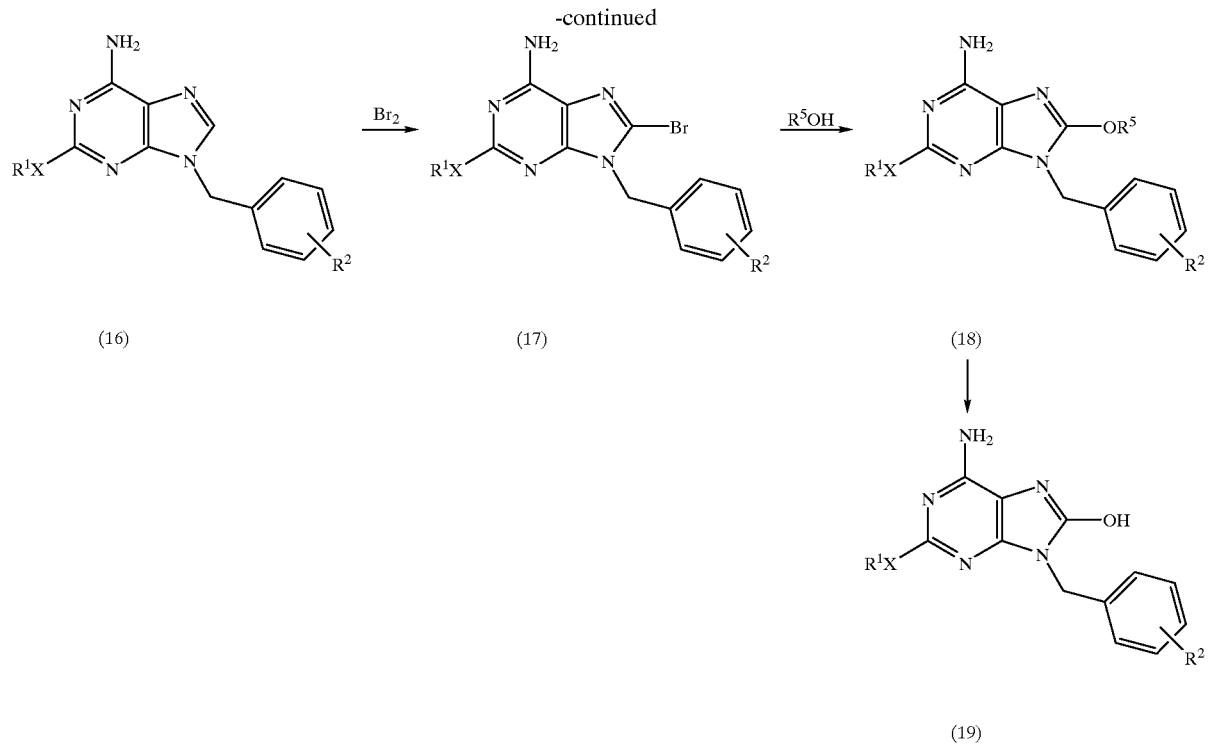

wherein R¹, X and R² are the same as definition in the formula (I), Z is halogen atom such as chlorine atom or bromine atom, or leaving group such as methanesulfonyloxy or p-toluenesulfonyloxy, and Y and R⁵ are the same as defined above.

Compound (11) is prepared by a method known by the skilled person. For instance, when Z is a chlorine atom, compound (11) is prepared by reacting compound (10) with phosphorousoxychloride.

The reaction temperature is selected from the range between room temperature and reflux temperature of the reaction solvent. When Z is methanesulfonyloxy, compound (11) is prepared by reacting compound (10) with methanesulfonyl chloride in the presence of a base in an organic solvent, and if necessary, NH₂ group on compound (10) is protected and then deprotected.

The bases are inorganic bases such as alkali metal carbonates (e.g. potassium carbonate), or organic bases, such as triethylamine, diisopropylethylamine, 4-dimethylaminopyridine or pyridine.

The organic solvents are halogenated hydrocarbons such as methylene chloride, ethers, such as diethyl ether or tetrahydrofuran, or aprotic solvents such as dimethylformamide, etc.

The reaction temperature is selected from the range between about 0° C. and around boiling point of the solvent.

Compound (12) is prepared by reacting compound (11) with R¹XH in an organic solvent.

When X is oxygen atom or sulfur atom, the reaction is preferably carried out in the presence of a base. The bases are alkali metals, such as sodium or potassium, alkali metal hydrides, such as sodium hydride or potassium hydride, or organometalic compounds, such as methyl lithium, butyl lithium or lithium diisopropylamide.

The organic solvents are aprotic solvents, such as dimethylformamide, acetonitrile or hexamethylphosphoroustriamide, or ethers, such as diethyl ether, tetrahydrofuran 1,4-dioxane or diglyme.

The reaction temperature is selected from the range between about room temperature and around the boiling point of the solvent.

Compound (13) is prepared by reacting compound (12) and compound (4) in the presence of a base in an organic solvent.

The bases are inorganic bases such as alkali metal carbonates (e.g. sodium carbonate, potassium carbonate), or organic bases, such as tertiary amines (e.g. triethylamine, diisopropylethylamine) or pyridines (e.g. dimethylaminopyridine, pyridine).

The organic solvents are halogenated hydrocarbons such as methylene chloride etc., ethers, such as diethyl ether or tetrahydrofuran, or aprotic solvents, such as dimethylformamide, dimethyl sulfoxide or acetonitrile.

The reaction temperature is selected from the range between about room temperature and around the boiling point of the solvent.

Compound (14) is prepared by nitrating compound (13) in an organic solvent, for example by adding nitric acid thereto in an organic solvent such as acetic acid.

The reaction temperature is selected from the range between about −20° C. and around the boiling point of the solvent.

Compound (15) is prepared by reducing nitro group on compound (14) in an organic solvent.

The reducing agents are hydrogen, sodium borohydride or lithium aluminum hydride.

The organic solvents are alcohols, such as methanol or ethanol, esters such as ethyl acetate, etc., or ethers, such as diethyl ether or tetrahydrofuran.

The reaction temperature is selected from the range between about 0° C. and around the boiling point of the solvent.

Compound (16) is prepared by reacting compound (15) with formic acid or trimethyl orthoformate in the presence of an acid.

The acids are inorganic acids such as hydrochloric acid, or organic acids, such as p-toluenesulfonic acid or camphor sulfonic acid.

The reaction temperature is selected from the range between about room temperature and around the boiling point of the solvent.

Compound (17) is prepared by reacting compound (16) and $Br_2$ in an organic solvent.

A reaction promoter such as sodium acetate may be added in this reaction.

The organic solvents are halogenated hydrocarbons, such as tetrachloromethane, methylene chloride or dichloroethane, ethers such as diethyl ether, acetic acid, or carbon disulfide.

The reaction temperature is selected from the range between about 0° C. and around the boiling point of the solvent.

Compound (18) is prepared by reacting compound (17) and $R^5OH$ in the presence of a base in an organic solvent.

The bases are alkali metals, such as sodium or potassium, alkali metal hydrides, such as sodium hydride or potassium hydride, or organometalic compounds, such as methyl lithium, butyl lithium or lithium diisopropylamide.

The organic solvents are ethers, such as diethyl ether or tetrahydrofuran, or aprotic solvents, such as dimethylformamide or acetonitrile. The alcohol used as the reagent, such as methanol, ethanol, propanol or butanol may be served as a solvent.

The reaction temperature is selected from the range between about room temperature and around the boiling point of the solvent.

Compound (19) is prepared by treating compound (18) with an acid in water or a mixture of water and an organic solvent.

The acids are inorganic acids, such as hydrochloric acid or hydrobromic acid, or organic acids such as trifluoroacetic acid, etc.

The organic solvents are ethers, such as diethyl ether or tetrahydrofuran, aprotic solvents, such as dimethylformamide or acetonitrile, alcohols, such as methanol, ethanol or propanol, or acetic acid.

The reaction temperature is selected from the range between about room temperature and around the boiling point of the solvent.

PROCESS 3

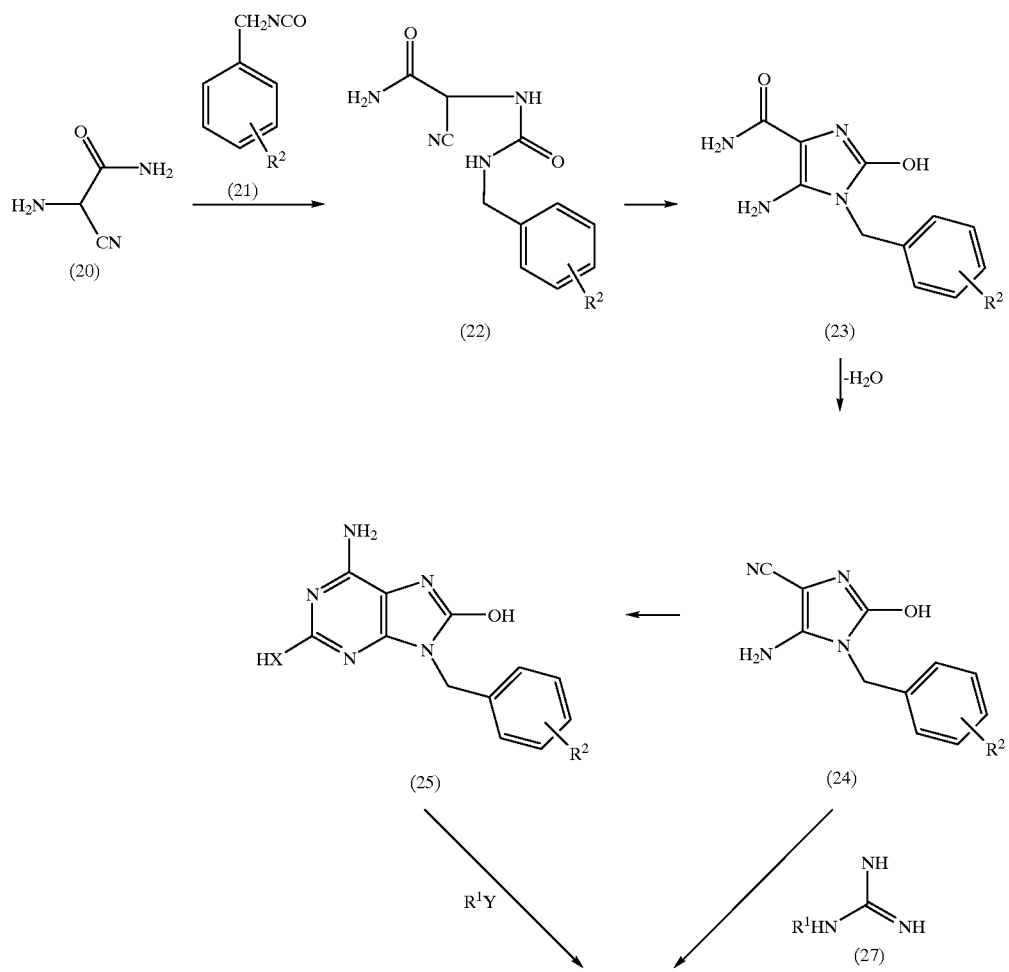

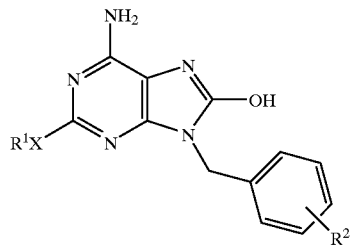

(26)

wherein $R^1$, X and $R^2$ are the same as definition in the formula (I), and Y is the same as defined above.

Compound (22) is prepared by reacting compound (20) and compound (21) in an organic solvent. The reaction can be carried out in the presence or absence of a solvent.

The bases are inorganic bases such as alkali metal carbonates (e.g. potassium carbonate), or organic bases, such as tertiary amines (e.g. triethylamine, diisopropylethylamine) or pyridines (e.g. 4-dimethylaminopyridine, pyridine).

The organic solvents are halogenated hydrocarbons such as methylene chloride, ethers, such as diethyl ether, tetrahydrofuran or 1,4-dioxane, or aprotic solvents, such as dimethylformamide, dimethyl sulfoxide or acetonitrile.

The reaction temperature is selected from the range between about 0° C. and around the boiling point of the solvent.

Compound (23) is prepared by cyclizing compound (22) in water, an organic solvent, or a mixture thereof. The reaction can be carried out in the presence or absence of a base.

The bases are inorganic bases, such as alkali metal hydroxide (e.g. sodium hydroxide, potassium hydroxide), alkali metal alkoxide (e.g. sodium methoxide) or alkali metal carbonates (e.g. potassium carbonate), or organic bases, such as tertiary amines (e.g. triethylamine or diisopropylethylamine) or pyridines (e.g. 4-dimethylaminopyridine, pyridine).

The organic solvents are halogenated hydrocarbons such as methylene chloride, ethers, such as diethyl ether, tetrahydrofuran or 1,4-dioxane, aprotic solvents, such as dimethylformamide or acetonitrile, or alcohols, such as methanol, ethanol or 2-propanol.

The reaction temperature is selected from the range between room temperature and around the boiling point of the solvent.

Compound (24) is prepared by dehydrating compound (23) in an organic solvent.

The dehydration agents are diphosphorus pentaoxide, dicyclohexyl carbodiimide, etc.

The organic solvents are halogenated hydrocarbons such as methylene chloride, or aprotic solvents, such as dimethylformamide or acetonitrile.

The reaction temperature is selected from the range between about room temperature and around the boiling point of the solvent.

When X is NH, compound (25) is prepared by reacting compound (24) and guanidine in the presence or absence of a base in an organic solvent or without any solvent.

The bases are inorganic bases, such as metal alkoxide (e.g. sodium methoxide), alkali metal hydroxide (e.g. sodium hydroxide), or alkali metal carbonates (e.g. potassium carbonate), or organic bases, such as tertiary amines (e.g. triethylamine, diisopropylethylamine) or pyridines (e.g. 4-dimethylaminopyridine, pyridine).

The organic solvents are for example, alcohols, such as ethanol or butanol, ethers, such as tetrahydrofuran or 1,4-dioxane, toluene, or aprotic solvents, such as dimethylformamide or dimethyl sulfoxide.

When X is oxygen atom, compound (25) is prepared by reacting compound (24) and urea in the presence or absence of a base in an organic solvent or without any solvent.

The bases are inorganic bases, such as metal alkoxide (e.g. sodium methoxide), alkali metal hydroxide (e.g. sodium hydroxide), or alkali metal carbonates (e.g. potassium carbonate), or organic bases such as tertiary amines (e.g. triethylamine) or pyridines (e.g. dimethylaminopyridine, pyridine).

The organic solvents are for example, alcohols, such as ethanol or butanol, ethers such as tetrahydrofuran or 1,4-dioxane, toluene, or aprotic solvents, such as dimethylformamide or dimethyl sulfoxide.

Compound (25) is also prepared by reacting compound (24) and benzoyl isocyanate in the presence or absence of a base in an organic solvent, and then by cyclizing the reactant in the presence of a base in water, an organic solvent, or a mixture thereof.

The bases used in the reaction with the isocyanate are alkali metal carbonates such as, potassium carbonate, or organic bases, such as tertiary amines (e.g. triethylamine, diisopropylethylamine) or pyridines (e.g. 4-dimethylaminopyridine, pyridine).

The organic solvents are for example, halogenated hydrocarbons such as methylene chloride, ethers, such as diethyl ether or tetrahydrofuran, or aprotic solvents, such as dimethylformamide or dimethyl sulfoxide.

The reaction temperature is selected from the range between about 0° C. and around the boiling point of the solvent.

The organic solvents used in the above cyclizing reaction are for example, alcohols, such as ethanol or 2-propanol, ethers such as tetrahydrofuran, or aprotic solvents, such as dimethylformamide or dimethyl sulfoxide.

The bases are for example, inorganic bases, such as alkali metal alkoxides (e.g. sodium methoxide), alkali metal hydroxide (e.g. sodium hydroxide) or ammonia, or organic bases, such as tertiary amines (e.g. triethylamine) or pyridines (e.g. 4-dimethylaminopyridine, pyridine).

The reaction temperature is selected from the range between around room temperature and around the boiling point of the solvent.

When X is sulfur atom, compound (25) is prepared by reacting compound (24) and thiourea in the presence or absence of a base in an organic solvent or without any solvent.

The bases are metal alkoxides (e.g. sodium methoxide), alkali metal hydroxides such as sodium hydroxide, alkali metal carbonates such as potassium carbonate, tertiary amines such as triethylamine, or pyridines such as 4-dimethylaminopyridine or pyridine.

The organic solvents are alcohols, such as ethanol or butanol, ethers, such as tetrahydrofuran or 1,4-dioxane, toluene, or aprotic solvents, such as dimethylformamide or dimethyl sulfoxide.

Compound (25) is also prepared by reacting compound (24) and benzoyl isothiocyanate in the presence or absence of a base in an organic solvent, and then by cyclizing the reactant in the presence of a base in water, an organic solvent, or a mixture thereof.

The bases used in the reaction with the isothiocyanate are alkali metal carbonates such potassium carbonate, tertiary amines, such as triethylamine or diisopropylethylamine, or pyridines, such as 4-dimethylaminopyridine or pyridine.

The organic solvents are halogenated hydrocarbons such as methylene chloride, ethers, such as diethyl ether or tetrahydrofuran, or aprotic solvents, such as dimethylformamide or dimethyl sulfoxide.

The reaction temperature is selected from the range between about 0° C. and around the boiling point of the solvent.

The organic solvents used in the above cyclizing reaction are for example, alcohols such as ethanol or 2-propanol, ethers such as tetrahydrofuran, or aprotic solvents, such as dimethylformamide or dimethyl sulfoxide.

The bases are inorganic bases such as metal alkoxides (e.g. sodium methoxide), alkali metal hydroxide (e.g. sodium hydroxide) or ammonia, or organic bases such as tertiary amines (e.g. triethylamine) or pyridines (e.g. 4-dimethylaminopyridine or pyridine).

The reaction temperature is selected from the range between around the room temperature and around boiling point of the solvent.

Compound (26) is prepared by reacting compound (25) with $R^1Y$ (wherein Y means leaving group such as halogen atom e.g. chlorine atom, bromine atom) in the presence of a base in an organic solvent. In this reaction $NH_2$ or OH group on compound (25) may be protected or deprotected, if necessary.

The bases are for example, alkali metal hydrogen carbonates such as sodium hydrogen carbonate, alkali metal carbonates such as sodium carbonate, tertiary amines such as triethylamine, or pyridines such as dimethylaminopyridine or pyridine.

The organic solvents are for example, halogenated hydrocarbon such as methylene chloride, ethers, such as diethyl ether or tetrahydrofuran, or aprotic solvents such as dimethylformamide.

The reaction temperature is selected from the range between about 0° C. and around the boiling point of the solvent.

When X is NH, compound (26) can be also prepared by reacting compound (24) and compound (27) in the presence or absence of a base in an organic solvent or without any solvent.

The bases are metal alkoxides such as sodium methoxide, alkali metal hydroxides, such as sodium hydroxide, alkali metal carbonates, such as sodium carbonate, tertiary amines such as triethylamine, or pyridines, such as 4-dimethylaminopyridine or pyridine.

The organic solvents are for example, alcohols, such as ethanol or butanol, ethers, such as tetrahydrofuran or dioxane, toluene, or aprotic solvents, such as dimethylformamide or dimethyl sulfoxide.

The compound (I) of the present invention and an intermediate for preparing it can be purified by the conventional method for example, column chromatography, recrystallization, etc.

The solvents for the recrystallization are for example, alcohols, such as methanol, ethanol or 2-propanol, ethers such as diethyl ether, esters such as ethyl acetate, aromatic hydrocarbon, such as benzene or toluene, ketones such as acetone, hydrocarbons such as hexane, or aprotic solvents, such as dimethylformamide or acetonitrile, or a mixture thereof.

Furthermore, on carrying the above reaction, the protection or deprotection techniques can be employed, if necessary. The protection or deprotection techniques are described in detail in "Protecting group in Organic Synthesis, by T. W. Greene and P. G. M. Wuts (1990)".

When the compound (I) of the present invention has an asymmetric carbon atom, optical isomers exist and therefore, a mixture thereof and an isolated optical isomer are included in the compound (I) of the present invention.

The compound (I) of the present invention can be orally or parenterally administered as an interferon inducer. A compound such that was metabolized in vivo into the compound (I) of the present invention, or its equivalent compound, so-called "pro-drug" should be included in the compound of the present invention.

The compound (I) of the present invention is generally administered in the form of a preparation together with a pharmaceutical carrier. Said pharmaceutical carriers are selected in accordance to the form of the preparation, but include for example, starch, lactose, hydroxypropylcellulose, hydroxypropylmethylcellulose, polyvinylpyrrolidone, aluminum stearate, magnesium stearate, etc.

In regards to oral administration, the preparation is administered in the conventional administration form, for example tablets, capsules, syrups, or suspensions.

In regard to parenteral administration, the compound is prepared into solutions, emulsions, suspensions etc., and administered in the form of injections, or in the form of suppositories, transdermal formulations or propellants.

Furthermore, the compound may be administered in the form of sustained release preparations.

Such preparations as mentioned above are prepared by admixing known carriers, fillers, binders or stabilizing agents with an active ingredient by a conventional method.

In case of preparing injections, buffer agents, solubilizing agents, tonicity agents, etc. may be added to them.

Dose and number of administration vary with a disease to be treated, situation of a patient in question, age, weight, sex, rout of administration and a kind of preparations. When the preparation is orally administered, an active ingredient is administered generally about 1–1000 mg per day, preferably about 10–500 mg, once or divided into several times. In case of injections, an active ingredient is administered generally about 0.1–500 mg per day, preferably about 3–100 mg, once or divided into several times.

The interferon inducer of the present invention can be used as therapeutic or prophylactic agents such as antivirus agents, anticancer agents or agents for anti immunologic disease. The route of administration is oral or parenteral as mentioned above.

EXAMPLE

The examples and reference examples are illustrated as follows. However, the scope of the present invention should not be limited to these examples.

Example 1

6-Amino-9-benzyl-8-hydroxy-2-methylthiopurine

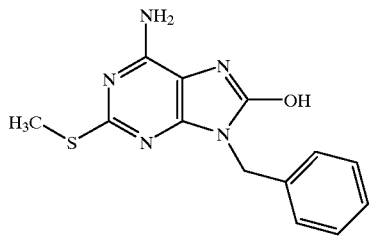

6-Amino-9-benzyl-8-bromo-2-methylthiopurine (10 mg, 0.026 mmol) in concentrated hydrochloric acid (10 ml) was refluxed for 4 hours under heating. The reaction mixture was made basic with 28% aqueous ammonia, and the resulting crystals were filtered, washed with water and dried to give the subject compound (8 mg, yield 96%).

$^1$H-NMR (DMSO-$d_6$) δ: 9.60 (1H, br s), 7.31 (5H, m), 6.53 (2H, br s), 4.88 (2H, s), 2.42 (3H, s).

Example 2

6-Amino-9-benzyl-2-ethylthio-8-hydroxypurine

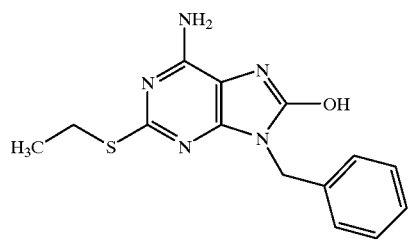

6-Amino-9-benzyl-8-bromo-2-ethylthiopurine (25 mg, 0.069 mmol) in concentrated hydrochloric acid (25 ml) was refluxed for 4 hours under heating. The reaction mixture was made basic with 28% aqueous ammonia, and the resulting crystals were filtered, washed with water and dried to give the subject compound (6 mg, yield 29%). $^1$H-NMR (DMSO-d6) δ: 10.09 (1H, br s), 7.31 (5H, m), 6.51 (2H, br s), 4.88 (2H, s), 2.97 (2H, q, J=7.3 Hz), 1.25 (3H, t, J=7.3 Hz).

Example 3

6-Amino-9-benzyl-8-hydroxy-2-(propylthio)purine

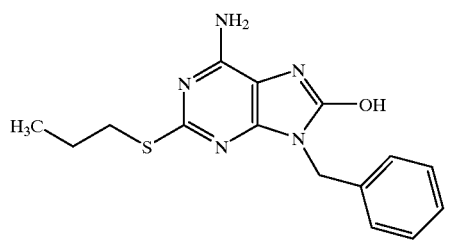

6-Amino-9-benzyl-8-bromo-2-(propylthio)purine (33 mg, 0.087 mmol) in concentrated hydrochloric acid (35 ml) was refluxed for 2 hours under heating. The reaction mixture was made basic with 28% aqueous ammonia, and the resulting crystals were filtered, washed with water and dried to give the subject compound (24 mg, yield 87%).

$^1$H-NMR (DMSO-$d_6$) δ: 10.19 (1H, br s), 7.31 (5H, m), 6.55 (2H, br s), 4.87 (2H, s), 2.98 (2H, t, J=6.9 Hz), 1.61 (2H, m), 0.94 (3H, t, J=7.2 Hz).

Example 4

6-Amino-9-benzyl-8-hydroxy-2-(isopropylthio) purine

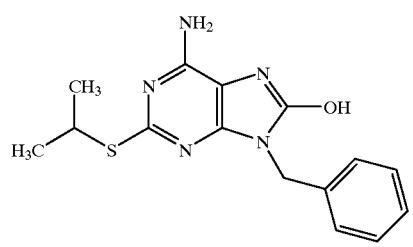

6-Amino-9-benzyl-8-bromo-2-(isopropylthio)purine (15 mg, 0.040 mmol) in concentrated hydrochloric acid (20 ml) was refluxed for 2 hours under heating. The reaction mixture was made basic with 28% aqueous ammonia, and the resulting crystals were filtered, washed with water and dried to give the subject compound (10 mg, yield 79%).

$^1$H-NMR (DMSO-$d_6$) δ: 10.09 (1H, s), 7.32 (5H, m), 6.50 (2H, br s), 4.87 (2H, s), 3.78 (1H, m), 1.30 (6H, d, J=6.9 Hz).

Example 5

6-Amino-9-benzyl-2-(butylthio)-8-hydroxypurine

6-Amino-9-benzyl-8-bromo-2-(butylthio)purine (23 mg, 0.059 mmol) in concentrated hydrochloric acid (10 ml) was refluxed for 5 hours under heating. The reaction mixture was made basic with 28% aqueous ammonia, and the resulting crystals were filtered, washed with water and dried to give the subject compound (14 mg, yield 99%).

$^1$H-NMR (DMSO-$d_6$) δ: 10.05 (1H, br s), 7.30 (5H, m), 6.50 (2H, br s), 4.88 (2H, s), 3.00 (2H, t, J=7.0 Hz), 1.58 (2H, m), 1.35 (2H, m), 0.86 (3H, t, J=7.2 Hz).

Example 6

6-Amino-9-benzyl-8-hydroxy-2-(isobutylthio)purine

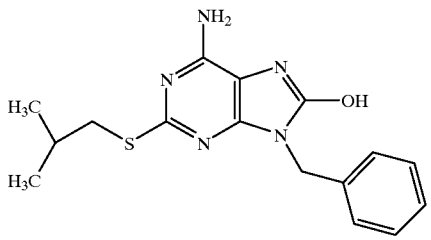

6-Amino-9-benzyl-8-bromo-2-(isobutylthio)purine (21 mg, 0.053 mmol) in concentrated hydrochloric acid (20 ml) was refluxed for 5 hours under heating. The reaction mixture was made basic with 28% aqueous ammonia, and the resulting crystals were filtered, washed with water and dried to give the subject compound (16 mg, yield 91%).

$^1$H-NMR (DMSO-$d_6$) δ: 10.10 (1H, s), 7.26–7.35 (5H, m), 6.51 (2H, br s), 4.87 (2H, s), 2.93 (2H, d, J=6.6 Hz), 1.83(1H, m), 0.93 (6H, d, J=6.6 Hz).

Example 7

6-Amino-9-benzyl-8-hydroxy-2-(sec-butylthio)purine

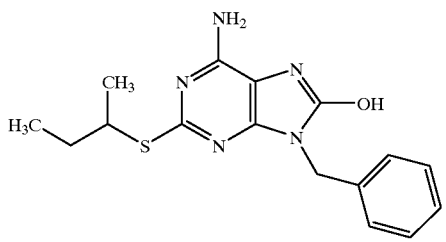

6-Amino-9-benzyl-8-bromo-2-(sec-butylthio)purine (39 mg, 0.092 mmol) in concentrated hydrochloric acid (20 ml) was refluxed for 2 hours under heating. The reaction mixture was made basic with 28% aqueous ammonia, and the resulting crystals were filtered, washed with water and dried to give the subject compound (12 mg, yield 40%).

$^1$H-NMR (DMSO-$d_6$) δ: 10.09 (1H, br s), 7.24–7.35 (5H, m), 6.50 (2H, br s), 4.87 (2H, s), 3.65 (1H, m), 1.61 (2H, m), 1.28 (3H, d, J=7.0 Hz), 0.93 (3H, t, J=7.3 Hz).

Example 8

6-Amino-9-benzyl-hydroxy-2-(pentylthio)purine

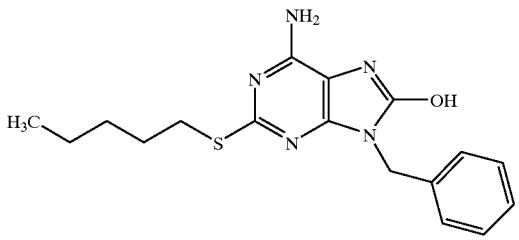

6-Amino-9-benzyl-8-bromo-2-(pentylthio)purine (39 mg, 0.096 mmol) in concentrated hydrochloric acid (35 ml) was refluxed for 2.5 hours under heating. The reaction mixture was made basic with 28% aqueous ammonia, and the resulting crystals were filtered, washed with water and dried to give the subject compound (30 mg, yield 91%).

$^1$H-NMR (DMSO-$d_6$) δ: 10.05 (1H, br s), 7.30 (5H, m), 6.50 (2H, br s), 4.88 (2H, s), 2.99 (2H, t, J=7.3 Hz), 1.59 (2H, m), 1.30 (4H, m), 0.84 (3H, t, J=7.3 Hz).

Example 9

6-Amino-9-benzyl-8-hydroxy-2-13-methylbutylthio)purine

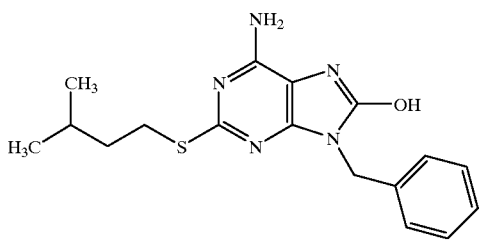

6-Amino-9-benzyl-8-bromo-2-(3-methylbutylthio)purine (11 mg, 0.027 mmol) in concentrated hydrochloric acid (20 ml) was refluxed for 3 hours under heating. The reaction mixture was made basic with 28% aqueous ammonia, and the resulting crystals were filtered, washed with water and dried to give the subject compound (7 mg, yield 75%).

$^1$H-NMR (DMSO-$d_6$) δ: 10.10 (1H, br s), 7.30 (5H, m), 6.50 (2H, br s), 4.88 (2H, s), 3.00 (2H, t, J=7.6 Hz) 1.63 (1H, m), 1.51 (2H, m), 0.86 (6H, t, J=6.2 Hz).

Example 10

6-Amino-9-benzyl-8-hydroxy-2-(2-methylbutylthio)purine

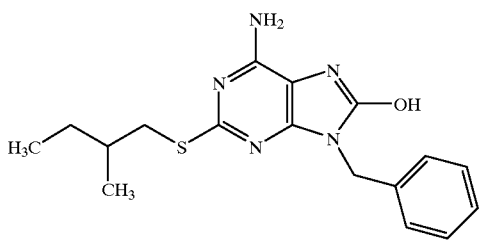

6-Amino-9-benzyl-8-bromo-2-(2-methylbutylthio)purine (29 mg, 0.071 mmol) in concentrated hydrochloric acid (20 ml) was refluxed for 3 hours under heating. The reaction mixture was made basic with 28% aqueous ammonia, and the resulting crystals were filtered, washed with water and dried to give the subject compound (6 mg, yield 25%).

$^1$H-NMR (DMSO-$d_6$) δ: 10.08 (1H, s), 7.30 (5H, m), 6.50 (2H, br s), 4.88 (2H, s), 3.08 (1H, q, J=6.6 Hz), 2.86 (1H, m), 1.62 (1H, m), 1.43 (1H, m), 1.15 (1H, m), 0.91 (3H, d, J=6.6 Hz), 0.86 (3H, t, J=6.2 Hz).

Example 11

6-Amino-9-benzyl-2-cyclohexylthio-8-hydroxypurine

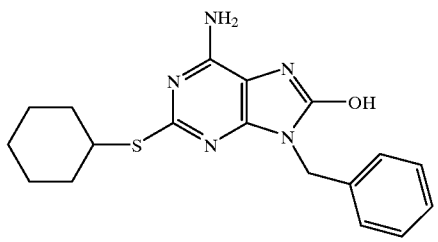

6-Amino-9-benzyl-8-bromo-2-cyclohexylthiopurine (20 mg, 0.048 mmol) in concentrated hydrochloric acid (10 ml) was refluxed for 6 hours under heating. The reaction mixture was made basic with 28% aqueous ammonia, and the resulting crystals were filtered, washed with water and dried to give the subject compound (12 mg, yield 70%).

$^1$H-NMR (DMSO-$d_6$) δ: 10.09 (1H, br s), 7.31 (5H, m), 6.49 (2H, br s), 4.87 (2H, s), 3.62 (1H, m), 2.00 (2H, m), 1.68 (2H, m), 1.62–1.56 (1H, m), 1.35 (5H, m).

Example 12

6-Amino-9-benzyl-8-hydroxy-2-phenylthiopurine

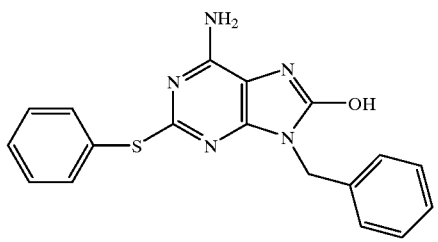

6-Amino-9-benzyl-8-bromo-2-phenylthiopurine (31 mg, 0.075 mmol) in concentrated hydrochloric acid (20 ml) was refluxed for 12 hours under heating. The reaction mixture was made basic with 28% aqueous ammonia, and the resulting crystals were filtered, washed with water and dried to give the subject compound (11 mg, yield 42%).

$^1$H-NMR (DMSO-$d_6$) δ: 9.50 (1H, br s), 7.55 (2H, m), 7.46 (3H, m), 7.28 (3H, m), 7.13 (2H, m), 6.55 (2H, br s), 4.67 (2H, s).

Example 13

6-Amino-9-benzyl-8-hydroxy-2-(p-tolylthio)purine

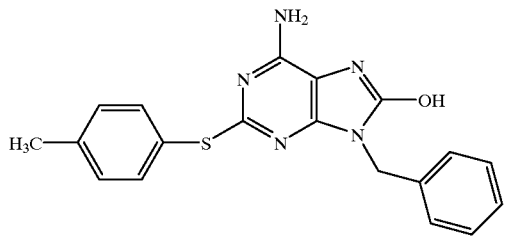

6-Amino-9-benzyl-8-bromo-2-(p-tolylthio)purine (15 mg, 0.035 mmol) in concentrated hydrochloric acid (20 ml) was refluxed for 7.5 hours under heating. The reaction mixture was made basic with 28% aqueous ammonia, and the resulting crystals were filtered, washed with water and dried to give the subject compound (5 mg, yield 39%).

$^1$H-NMR (DMSO-$d_6$) δ: 7.44 (2H, d, J=7.9 Hz), 7.27 (5H, m), 7.13 (2H, m), 6.51 (2H, br s), 4.67 (2H, s), 2.35 (3H, s).

Example 14

6-Amino-9-benzyl-8-hydroxy-2-(2-naphthylthio)purine

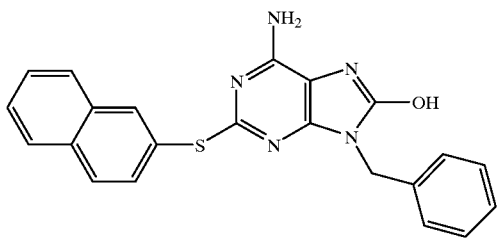

6-Amino-9-benzyl-8-bromo-2-(2-naphthylthio)purine (33 mg, 0.043 mmol) in a mixture of concentrated hydrochloric acid (20 ml) and dimethyl sulfoxide (7 ml) was refluxed for 6 hours under heating. The reaction mixture was made basic with 28% aqueous ammonia, and the resulting crystals were filtered, washed with water and the crude product was purified by thin-layer chromatography to give the subject compound (6 mg, yield 35%).

$^1$H-NMR (DMSO-$d_6$) δ: 10.14 (1H, br s), 8.30 (1H, d, J=8.6 Hz), 7.98–8.07 (2H, m), 7.67–7.77 (3H, m), 7.12–7.20 (3H, m), 6.69 (2H, d, J=6.9 Hz), 6.59 (2H, br s), 4.58 (2H, s).

Example 15

6-Amino-9-benzyl-2-benzylthio-8-hydroxypurine

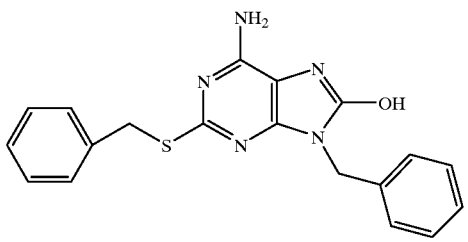

6-Amino-9-benzyl-2-benzylthio-8-bromopurine (18 mg, 0.042 mmol) in concentrated hydrochloric acid (10 ml) was refluxed for 9 hours under heating. The reaction mixture was made basic with 28% aqueous ammonia, and the resulting crystals were filtered, washed with water and dried to give the subject compound (8 mg, yield 52%).

$^1$H-NMR (DMSO-ds) δ: 10.12 (1H, br s), 7.19–7.34 (10H, m), 6.58 (2H, br s), 4.91 (2H, s), 4.29 (2H, s).

Example 16

6-Amino-9-benzyl-8-hydroxy-2-methoxypurine

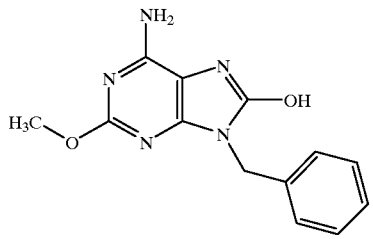

6-Amino-9-benzyl-2,8-dimethoxypurine (53 mg, 0.186 mmol) in concentrated hydrochloric acid (10 ml) was stirred for 3 hours at room temperature. The reaction mixture was made basic with 28% aqueous ammonia, and the resulting crystals were filtered and washed with water to give the subject compound (38 mg, yield 75%).

$^1$H-NMR (DMSO-$d_6$) δ: 9.95 (1H, br s), 7.35–7.22 (5H, m), 6.50 (2H, br s), 4.86 (2H, s), 3.76 (3H, s).

Example 17

6-Amino-9-benzyl-2-ethoxy-8-hydroxypurine

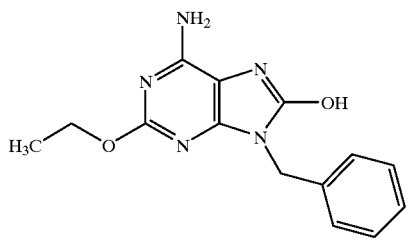

6-Amino-9-benzyl-2-ethoxy-8-methoxypurine (18 mg, 0.06 mmol) in concentrated hydrochloric acid (5 ml) was stirred for 3 hours at room temperature. The reaction mixture was made basic with 28% aqueous ammonia, and the resulting crystals were filtered and washed with water to give the subject compound (11 mg, yield 64%).

$^1$H-NMR (DMSO-$d_6$) δ: 9.96 (1H, br s), 7.35–7.23 (5H, m), 6.45 (2H, br s), 4.85 (2H, s), 4.19 (2H, q, J=7.1 Hz), 1.25 (3H, t, J=7.1 Hz).

Example 18

6-Amino-9-benzyl-8-hydroxy-2-propoxypurine

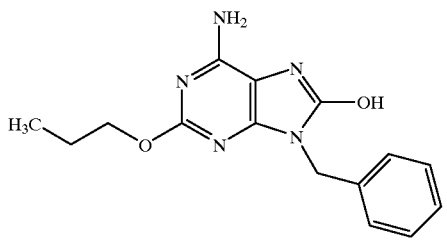

6-Amino-9-benzyl-8-methoxy-2-propoxypurine (75 mg, 0.24 mmol) in concentrated hydrochloric acid (15 ml) was stirred for 3 hours at room temperature. The reaction mixture was made basic with 28% aqueous ammonia, and the resulting crystals were filtered and washed with water to give the subject compound (59 mg, yield 83%).

$^1$H-NMR (DMSO-d) δ: 9.96 (1H, br s), 7.35–7.22 (5H, m), 6.45 (2H, br s), 4.86 (2H, s), 4.10 (2H, t, J=6.8 Hz), 1.65 (2H, m), 0.93 (3H, t, J=7.3 Hz).

Example 19

6-Amino-9-benzyl-2-butoxy-8-hydroxypurine

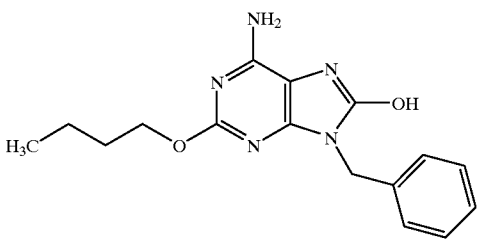

6-Amino-9-benzyl-2-butoxy-8-methoxypurine (20 mg, 0.061 mmol) in concentrated hydrochloric acid (5 ml) was stirred for 3 hours at room temperature. The reaction mixture was made basic with 28% aqueous ammonia. The resulting crystals were filtered, washed with water, and the crude product was purified by silica gel chromatography (3% methanol/chloroform) to give the subject compound (13 mg, yield 68%).

$^1$H-NMR (DMSO-$d_6$) δ: 9.95 (1H, br s), 7.35–7.23 (5H, m), 6.45 (2H, br s), 4.86 (2H, s), 4.13 (2H, t, J=6.4 Hz), 1.62 (2H, m), 1.37 (2H, m), 0.90 (3H, t, J=7.3 Hz).

Example 20

6-Amino-9-benzyl-8-hydroxy-2-pentoxypurine

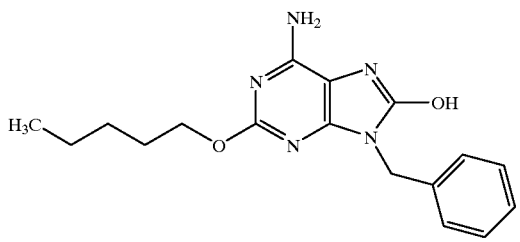

6-Amino-9-benzyl-8-methoxy-2-pentoxypurine (40 mg, 0.117 mmol) in concentrated hydrochloric acid (20 ml) was stirred for 12 hours at room temperature. The reaction mixture was made basic with 28% aqueous ammonia. The resulting crystals were filtered and washed with water to give the subject compound (33 mg, yield 86%).

$^1$H-NMR (DMSO-$d_6$) δ: 9.97 (1H, br s), 7.35–7.24 (5H, m), 6.44 (2H, br s), 4.85 (2H, s), 4.13 (2H, t, J=6.6 Hz), 1.62 (2H, m), 1.32 (4H, m), 0.88 (3H, t, J=6.4 Hz).

Example 21

6-Amino-9-benzyl-8-hydroxy-2-methylaminopurine

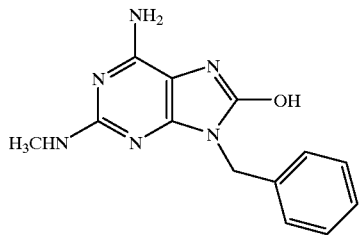

6-Amino-9-benzyl-8-bromo-2-methylaminopurine (55 mg, 0.17 mmol) in concentrated hydrochloric acid (30 ml) was refluxed for 5 hours under heating. The reaction mixture was made basic with 28% aqueous ammonia. The resulting crystals were filtered, washed with water and dried to give the subject compound (42 mg, yield 94%).

$^1$H-NMR (DMSO-$d_6$) δ: 9.67 (1H, br s), 7.31–7.24 (5H, m), 6.19 (1H, q, J=4.8 Hz), 6.06 (2H, br s), 4.81 (2H, s), 2.69 (3H, d, J=4.8 Hz).

Example 22

6-Amino-9-benzyl-2-ethylamino-8-hydroxypurine

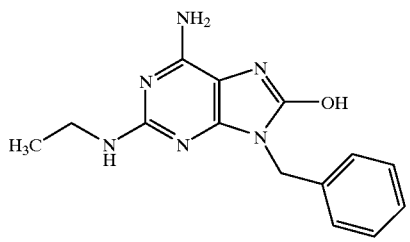

6-Amino-9-benzyl-8-bromo-2-ethylaminopurine (55 mg, 0.16 mmol) in concentrated hydrochloric acid (30 ml) was refluxed for 5 hours under heating. The reaction mixture was made basic with 28% aqueous ammonia. The resulting crystals were filtered, washed with water and dried to give the subject compound (45 mg yield: quantitatively).

$^1$H-NMR (DMSO-$d_6$) δ: 9.65 (1H, br s), 7.34–7.24 (5H, m), 6.18 (1H, t, J=5.55 Hz), 6.01 (2H, br s), 4.81 (2H, s), 3.19 (2H, m), 1.06 (3H, t, J=7.1 Hz).

Example 23

6-Amino-9-benzyl-8-hydroxy-2-propylaminopurine

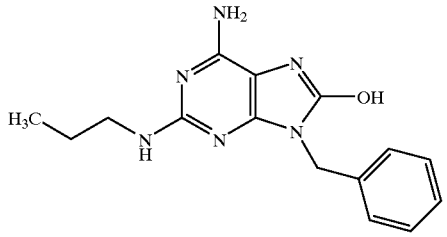

6-Amino-9-benzyl-8-bromo-2-propylaminopurine (86 mg, 0.24 mmol) in concentrated hydrochloric acid (30 ml) was refluxed for 5 hours under heating. The reaction mixture was made basic with 28% aqueous ammonia. The resulting crystals were filtered, washed with water and dried to give the subject compound (69 mg, yield 97%).

$^1$H-NMR (DMSO-$d_6$) δ: 9.64 (1H, br s), 7.34–7.24 (5H, m), 6.22 (1H, t, J=5.5 Hz), 6.00 (2H, br s), 4.80 (2H, s), 3.12 (2H, m), 1.46 (2H, m), 0.85 (3H, t, J=7.5 Hz).

Example 24

6-Amino-9-benzyl-2-butylamino-8-hydroxypurine

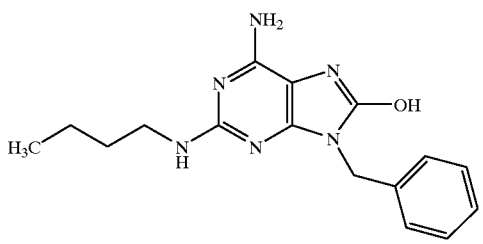

6-Amino-9-benzyl-8-bromo-2-butylaminopurine (78 mg, 0.21 mmol) in concentrated hydrochloric acid (30 ml) was refluxed for 5 hours under heating. The reaction mixture was made basic with 28% aqueous ammonia. The resulting crystals were filtered, washed with water and dried to give the subject compound (54 mg, yield 83%).

$^1$H-NMR (DMSO-$d_6$) δ: 9.64 (1H, br s), 7.29–7.24 (5H, m), 6.19 (1H, t, J=6.2 Hz), 6.00 (2H, br s), 4.80 (2H, s), 3.15 (2H, m), 1.43 (2H, m), 1.28 (2H, m), 0.87 (3H, t, J=7.3 Hz).

Example 25

6-Amino-9-benzyl-8-hydroxy-2-pentylaminopurine

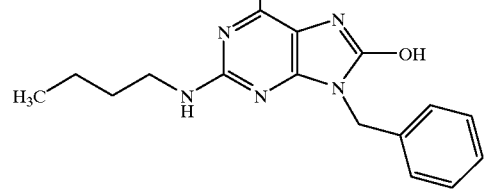

6-Amino-9-benzyl-8-bromo-2-pentylaminopurine (74 mg, 0.19 mmol) in concentrated hydrochloric acid (20 ml) was refluxed for 5 hours under heating. The reaction mixture was made basic with 28% aqueous ammonia. The resulting crystals were filtered, washed with water and dried to give the subject compound (36 mg, yield 58%).

$^1$H-NMR (DMSO-$d_5$) δ: 9.63 (1H, br s), 7.30–7.24 (5H, m), 6.19 (1H, t, J=5.3 Hz), 5.99 (2H, br s), 4.80 (2H, s), 3.19–3.11 (2H, m), 1.48–1.43 (2H, m), 1.27–1.24 (4H, m), 0.85 (3H, t, J=7.0 Hz).

Example 26

6-Amino-9-benzyl-8-hydroxy-2-(isopropylamino)
purine

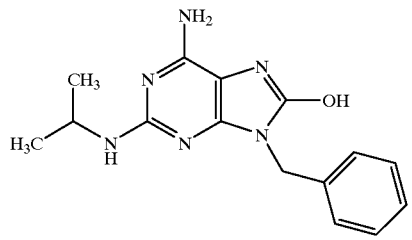

6-Amino-9-benzyl-8-bromo-2-(isopropylamino)purine (68 mg, 0.19 mmol) in concentrated hydrochloric acid (20 ml) was refluxed for 5 hours under heating. The reaction mixture was made basic with 28% aqueous ammonia. The resulting crystals were filtered, washed with water and dried to give the subject compound (50 mg, yield 89%).

$^1$H-NMR (DMSO-d$_6$) δ: 9.64 (1H, br s), 7.34–7.21 (5H, m), 5.99 (2H, br s), 5.98 (1H, d, J=8.2 Hz), 4.80 (2H, s), 4.00–3.90 (1H, m), 1.08 (6H, d, J=6.4 Hz).

Example 27

6-Amino-9-benzyl-8-hydroxy-2-(isobutylamino)
purine

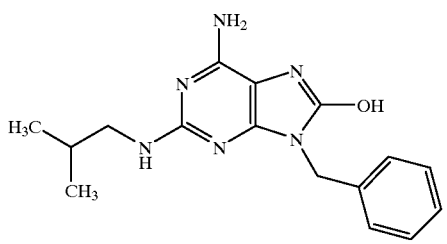

6-Amino-9-benzyl-8-bromo-2-(isobutylamino)purine (55 mg, 0.19 mmol) in concentrated hydrochloric acid (20 ml) was refluxed for 5 hours under heating. The reaction mixture was made basic with 28% aqueous ammonia. The resulting crystals were filtered, washed with water and dried to give the subject compound (30 mg, yield 52%).

$^1$H-NMR (DMSO-d$_6$) δ: 9.63 (1H, br s), 7.30–7.22 (5H, m), 6.24 (1H, t, J=6.0 Hz), 5.99 (2H, br s), 4.80 (2H, s), 2.99 (2H, dd, J=6.0, 6.0 Hz), 1.84–1.75 (1H, m), 0.84 (6H, d, J=6.8 Hz).

Example 28

6-Amino-9-benzyl-8-hydroxy-2-(sec-butylamino)
purine

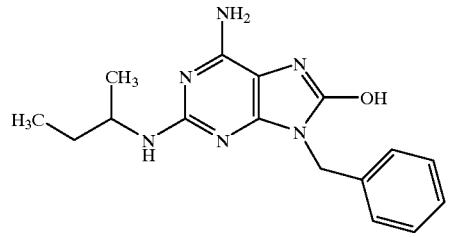

6-Amino-9-benzyl-8-bromo-2-(sec-butylamino)purine (50 mg, 0.13 mmol) in concentrated hydrochloric acid (20 ml) was refluxed for 5 hours under heating. The reaction mixture was made basic with 28% aqueous ammonia. The resulting crystals were filtered, washed with water and dried to give the subject compound (23 mg, yield 55%).

$^1$H-NMR (DMSO-d$_6$) δ: 9.63 (1H, br s), 7.31–7.24 (5H, m), 5.97 (2H, br s), 5.95 (1H, d, J=8.6 Hz), 4.80 (2H, s), 3.82–3.74 (1H, m), 1.51–1.34 (2H, m), 1.04 (3H, d, J=6.4 Hz), 0.83 (3H, t, J=7.3 Hz).

Example 29

6-Amino-9-benzyl-2-(2,2-dimethylpropyl)amino-8-
hydroxypurine

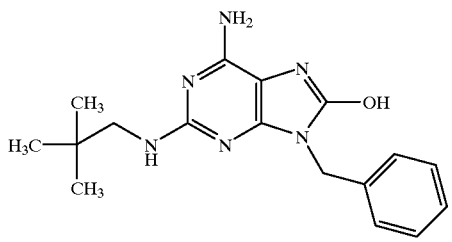

6-Amino-9-benzyl-8-bromo-2-(2,2-dimethylpropyl)aminopurine (70 mg, 0.18 mmol) in concentrated hydrochloric acid (20 ml) was refluxed for 5 hours under heating. The reaction mixture was made basic with 28% aqueous ammonia. The resulting crystals were filtered, washed with water and dried to give the subject compound (23 mg, yield 39%).

$^1$H-NMR (DMSO-d$_6$) δ: 9.63 (1H, br s), 7.28–7.21 (5H, m), 6.04 (1H, t, J=6.2 Hz), 5.97 (2H, br s), 4.79 (2H, s), 3.06 (2H, d, J=6.4 Hz), 0.83 (9H, s).

Example 30

6-Amino-9-benzyl-2-benzylamino-8-hydroxypurine

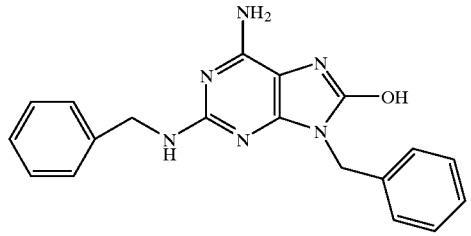

6-Amino-9-benzyl-2-benzylamino-8-bromopurine (37 mg, 0.09 mmol) in concentrated hydrochloric acid (50 ml) was refluxed for 5 hours under heating. The reaction mixture was made basic with 28% aqueous ammonia. The resulting crystals were filtered, washed with water and dried to give the subject compound (7 mg, yield 23%).

$^1$H-NMR (DMSO-d$_6$) δ: 9.75 (1H, br s), 7.31–7.15 (10H, m), 6.83 (1H, t, J=6.4 Hz), 6.10 (2H, br s), 4.78 (2H, s), 4.40 (2H, d, J=6.4 Hz).

Example 31

6-Amino-9-benzyl-2-cyclohexylamino-8-hydroxypurine

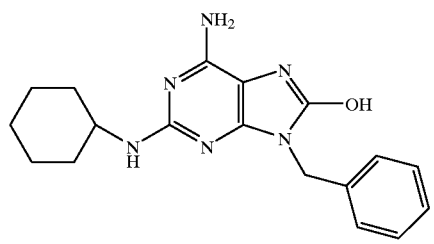

6-Amino-9-benzyl-8-bromo-2-cyclohexylaminopurine (82 mg, 0.20 mmol) in concentrated hydrochloric acid (30 ml) and methanol (20 ml) were refluxed for 5 hours under heating. After removal of methanol, the reaction mixture was made basic with 28% aqueous ammonia. The resulting crystals were filtered, washed with water and dried to give the subject compound (7 mg, yield 23%).

$^1$H-NMR (DMSO-d$_6$) δ: 9.62 (1H, br s), 7.28 (5H, m), 5.96 (3H, br s), 4.78 (2H, s), 3.58 (1H, m), 1.80 (2H, m), 1.65 (2H, m), 1.56 (1H, m), 1.27–1.06 (5H, m).

Example 32

6-Amino-2-anilino-9-benzyl-8-hydroxypurine

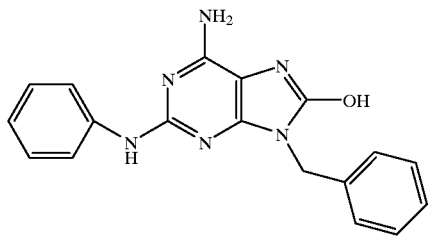

6-Amino-2-anilino-9-benzyl-8-bromopurine (80 mg, 0.20 mmol) in concentrated hydrochloric acid (200 ml) and methanol (50 ml) were refluxed for 5 hours under heating. The reaction mixture was condensed in vacuo, 28% aqueous ammonia was added to the residue. The resulting solid was filtered, washed with water and dried to give the subject compound (67 mg yield: quantitatively).

$^1$H-NMR (DMSO-d$_6$) δ: 10.00 (1H, Br s), 8.22 (1H, d, J=8.8 Hz), 7.80 (1H, d, J=2.2 Hz), 7.54 (1H, s), 7.47 (1H, dd, J=8.8, 2.2 Hz), 7.35–7.26 (7H, m), 6.45 (2H, br s), 4.89 (2H, s).

Example 33

6-Amino-9-benzyl-2-dimethylamino-8-hydroxypurine

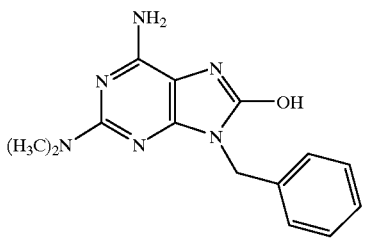

6-Amino-9-benzyl-2-dimethylamino-8-bromopurine (51 mg, 0.15 mmol) in concentrated hydrochloric acid (30 ml) and methanol (10 ml) were refluxed for 5 hours under heating. After removal of methanol, the reaction mixture was made basic with 28% aqueous ammonia. The resulting crystals were filtered, washed with water and dried to give the subject compound (38 mg, yield 91%).

$^1$H-NMR (DMSO-d$_6$) δ: 9.67 (1H, br s), 7.36–7.24 (5H, m), 6.08 (2H, br s), 4.82 (2H, s), 3.01 (6H, s).

Example 34

6-Amino-9-benzyl-2-benzylmethylamino-8-hydroxypurine

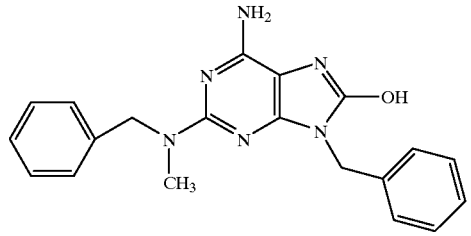

6-Amino-9-benzyl-2-benzylmethylamino-8-bromopurine (85 mg, 0.20 mmol) in concentrated hydrochloric acid (30 ml) and methanol (20 ml) were refluxed for 5 hours under heating. The reaction mixture was made basic with 28% aqueous ammonia, and the resulting crystals were filtered, washed with water and dried to give the subject compound (56 mg, yield 77%).

$^1$H-NMR (DMSO-$d_6$) δ: 9.70 (1H, br s), 7.29–7.19 (10H, m), 6.12 (2H, br s), 4.81 (2H, s), 4.77 (2H, s), 2.99 (3H, s).

Example 35

6-Amino-9-benzyl-8-hydroxy-2-(2-phthalimidoethyl)thiopurine

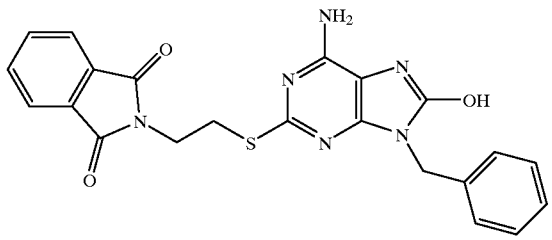

6-Amino-9-benzyl-8-hydroxy-2-mercaptopurine (120 mg, 0.44 mmol) was suspended in dimethylformamide (10 ml). To the suspension were added potassium carbonate (60 mg, 0.43 mmol) and 2-phthalimidoethyl bromide (112 mg, 0.44 mmol) in order. The mixture was stirred at room temperature for 2 hours. The solvent was removed in vacuo and to the residue was added saturated brine. The mixture was extracted with ethyl acetate, the organic layer was dried on magnesium sulfate, and the solvent was removed in vacuo. Methanol was added to the residue, and the resulting crystals were taken by filtration to give the subject compound (107 mg, yield 54%).

$^1$H-NMR (DMSO-$d_6$) δ: 10.19 (1H, br s), 7.83 (4H, m), 7.34 (5H, m), 6.52 (2H, br s), 4.96 (2H, s), 3.95 (2H, t, J=6.6 Hz), 3.32 (2H, t, J=6.6 Hz).

Example 36

6-Amino-9-benzyl-8-hydroxy-2-(3-phthalimidopropylthio)purine

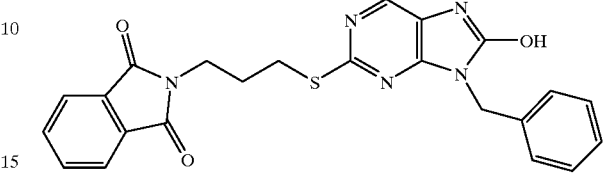

6-Amino-9-benzyl-8-hydroxy-2-mercaptopurine (110 mg, 0.40 mmol) was suspended in dimethylformamide (10 ml). To the suspension were added potassium carbonate (50 mg, 0.40 mmol) and 2-phthalimidoethyl bromide (108 mg, 0.40 mmol) in order. The mixture was stirred at room temperature for 2 hours. The solvent was removed in vacuo, water and methanol were added to the residue, and the resulting crystals were taken by filtration to give the subject compound (138 mg, yield 75%).

$^1$H-NMR (DMSO-$d_6$) δ: 10.09 (1H, s), 7.82 (4H, m), 7.24 (5H, m), 6.50 (2H, br s), 4.82 (2H, s), 3.67 (2H, t, J=6.2 Hz), 3.03 (2H, t, J=6.2 Hz), 1.96 (2H, m).

Example 37

6-Amino-9-benzyl-8-hydroxy-2-(4-phthalimidobutylthio)purine

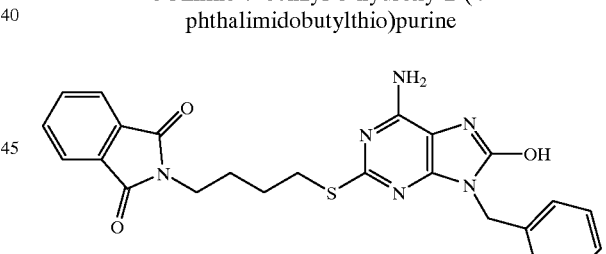

6-Amino-9-benzyl-8-hydroxy-2-mercaptopurine (120 mg, 0.44 mmol) was suspended in dimethylformamide (10 ml). To the suspension were added potassium carbonate (60 mg, 0.43 mmol) and 4-phthalimidobutyl bromide (113 mg, 0.40 mmol) in order. The mixture was stirred at room temperature for 2 hours. The solvent was removed in vacuo, and water and methanol were added to the residue, and the resulting crystals were taken by filtration to give the subject compound (141 mg, yield 74%).

$^1$H-NMR (DMSO-$d_6$) δ: 10.09 (1H, br s), 7.84 (4H, m), 7.29 (5H, m), 6.51 (2H, br s), 4.83 (2H, s), 3.56 (2H, t, J=6.3 Hz), 3.03 (2H, t, J=6.9 Hz), 1.67 (4H, m).

Example 38

3-[(6-Amino-9-benzyl-8-hydroxy-2-purinyl)thio]propanol

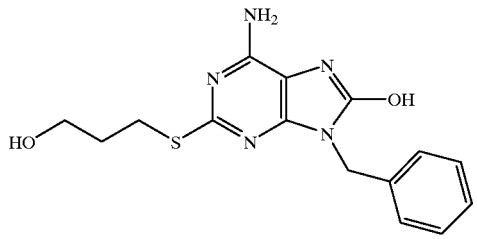

Crude 6-amino-9-benzyl-8-hydroxy-2-mercaptopurine (200 mg, 0.73 mmol) was suspended in dimethylformamide (100 ml). To the suspension were added potassium carbonate (150 mg, 1.1 mmol) and 3-bromo-1-propanol (0.1 ml, 1 mmol) in order. The mixture was stirred at room temperature for 4 hours. The solvent was removed in vacuo, and the residue was purified by silica gel chromatography (1% methanol/chloroform) to give the subject compound (149 mg, yield 62%).

$^1$H-NMR (DMSO-d$_6$) δ: 10.09 (1H, s), 7.31 (5H, m), 6.50 (2H, br s), 4.90 (2H, s), 4.50 (1H, t, J=5.6 Hz), 3.49 (2H, m), 3.07 (2H, t, J=6.6 Hz), 1.75 (2H, m).

Example 39

6-Amino-9-henzyl-8-hydroxy-2-(methoxycarbonylmethylthio)purine

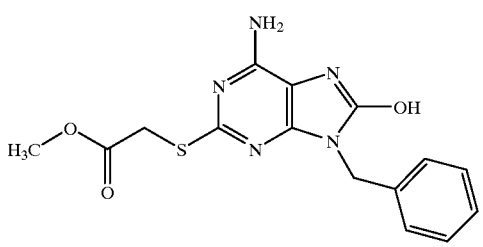

Crude 6-amino-9-benzyl-8-hydroxy-2-mercaptopurine (200 mg, 0.73 mmol) was suspended in dimethylformamide (80 ml). To the suspension were added potassium carbonate (150 mg, 1.1 mmol) and methyl bromoacetate (0.1 ml, 1.1 mmol) in order. The mixture was stirred at room temperature for 2 hours. The solvent was removed in vacuo, and the residue was purified by silica gel chromatography (3% methanol/chloroform) to give the subject compound (173 mg, yield 69%).

$^1$H-NMR (DMSO-d$_6$) δ: 10.12 (1H, s), 7.30 (5H, m), 6.57 (2H, br s), 4.84 (2H, s), 3.91 (2H, m), 3.56 (2H, s).

Example 40

6-Amino-9-benzyl-8-hydroxy-2-[2-(methoxycarbonyl)ethyl]thiopurine

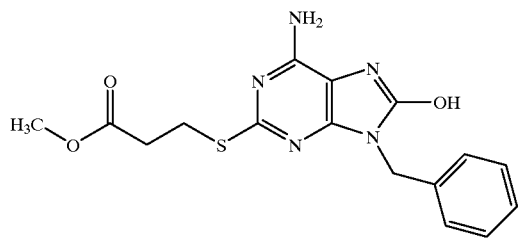

Crude 6-amino-9-benzyl-8-hydroxy-2-mercaptopurine (200 mg, 0.73 mmol) was suspended in dimethylformamide (80 ml). To the suspension were added potassium carbonate (150 mg, 1.1 mmol) and methyl 3-bromopropionate (0.12 ml, 1.1 mmol) in order. The mixture was stirred at room temperature for 2 hours. The solvent was removed in vacuo, and the residue was purified by silica gel chromatography (3% methanol/chloroform) to give the subject compound (146 mg, yield 56%).

$^1$H-NMR (DMSO-d$_6$) δ: 10.12 (1H, s), 7.30 (5H, m), 6.57 (2H, br s), 4.84 (2H, s), 3.91 (2H, s), 3.56 (2H, s).

Exanple 41

6-Amino-9-benzyl-8-hydroxy-2-(carboxymethylthio)purine

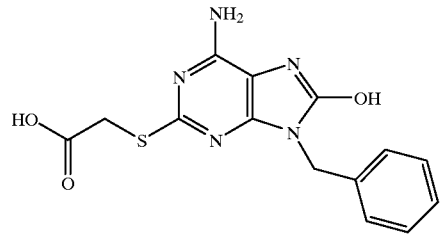

To a methanol solution (5 ml) containing 500 mg of sodium hydroxide was added 6-amino-9-benzyl-8-hydroxy-2-(methoxycarbonylmethyl)thiopurine (64 mg, 0.19 mmol). The solution was refluxed under heating, neutralized with 2N hydrochloric acid, filtered and washed with water to give the subject compound (32 mg, yield 52%).

$^1$H-NMR (DMSO-d$_6$) δ: 10.44 (1H, s), 7.34 (5H, m), 6.64 (2H, br s), 4.85 (2H, s), 3.82 (2H, s).

Example 42

6-Amino-9-benzyl-8-hydroxy-2-(methoxymethylthio)purine

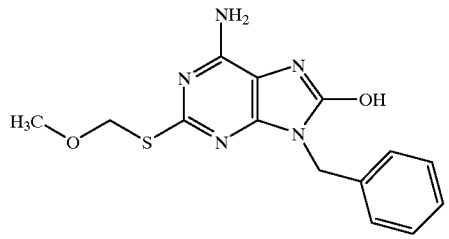

Crude 6-amino-9-benzyl-8-hydroxy-2-mercaptopurine (134 mg, 0.49 mmol) was suspended in dimethylformamide (65 ml). To the suspension were added potassium carbonate (100 mg, 0.72 mmol) and chloromethyl methyl ether (0.056 ml, 0.73 mmol) in order. The mixture was stirred at room temperature for 2 hours. The solvent was removed in vacuo, and the residue was purified by silica gel chromatography (2% methanol/chloroform) to give the subject compound (107 mg, yield 69%).

$^1$H-NMR (DMSO-$d_6$) δ: 10.15 (1H, s), 7.31 (5H, m), 6.59 (2H, br s), 5.29 (2H, s), 4.89 (2H, s), 3.21 (3H, s).

Example 43

6-Amino-9-benzyl-8-hydroxy-2-(2-ethoxyethyl)thiopurine

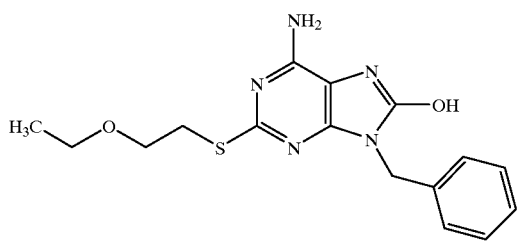

Crude 6-amino-9-benzyl-8-hydroxy-2-mercaptopurine (134 mg, 0.49 mmol) was suspended in dimethylformamide (65 ml). To the suspension were added potassium carbonate (100 mg, 0.72 mmol) and 2-chloroethyl ethyl ether (0.056 ml, 0.73 mmol) in order. The mixture was stirred at room temperature for 3 hours. The solvent was removed in vacuo, and the residue was purified by silica gel chromatography (1% methanol/chloroform) to give the subject compound (19 mg, yield 11%).

$^1$H-NMR (DMSO-$d_6$) δ: 10.11 (1H, s), 7.30 (5H, m), 6.54 (2H, br s), 4.88 (2H, s), 3.54 (2H, t, J=6.9 Hz), 3.43 (2H, q, J=7.0 Hz), 3.18 (2H, t, J=6.6 Hz), 1.08 (3H, t, J=6.9 Hz).

Example 44

6-Amino-9-benzyl-8-hydroxy-2-[(2-hydroxyethyl)thio]purine

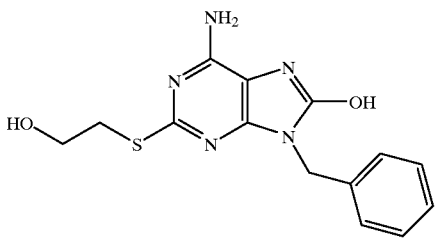

Crude 6-amino-9-benzyl-8-hydroxy-2-mercaptopurine (134 mg, 0.49 mmol) was suspended in dimethylformamide (65 ml). To the suspension were added potassium carbonate (100 mg, 0.72 mmol) and 2-bromoethanol (0.052 ml, 0.73 mmol) in order. The mixture was stirred at room temperature for 5 hours. The solvent was removed in vacuo, and the residue was purified by silica gel chromatography (2% methanol/chloroform) to give the subject compound (72 mg, yield 46%).

$^1$H-NMR (DMSO-$d_6$) δ: 10.09 (1H, s), 7.32 (5H, m), 6.52 (2H, br s), 4.87 (3H, s), 3.59 (2H, q, J=5.9 Hz), 3.12 (2H, t, J=6.6 Hz).

Example 45

[(6-Amino-9-benzyl-8-hydroxy-2-purinyl)thio]acetamide

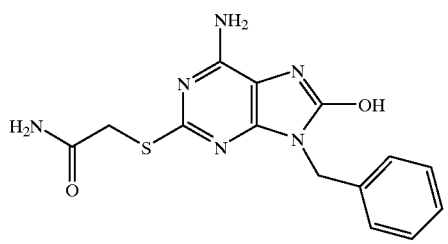

A 28% ammonia/methanol solution was added to 6-amino-9-benzyl-8-hydroxy-2-(methoxycarbonylmethyl)thiopurine (75 mg, 0.22 mmol). The solution was heated in autoclave for 6 hours and then the solvent was removed in vacuo. To the residue was added methanol and the resulting crystals were filtered to give the subject compound (64 mg, yield 89%).

$^1$H-NMR (DMSO-$d_6$) δ: 10.12 (1H, s), 7.42 (1H, br s), 7.34 (5H, m), 7.07 (1H, br s), 6.57 (2H, br s), 4.87 (2H, s), 3.70 (2H, s).

Example 46

6-Amino-9-benzyl-2-[(1,3-dioxolan-2-yl)-methyl]thio-8-hydroxypurine

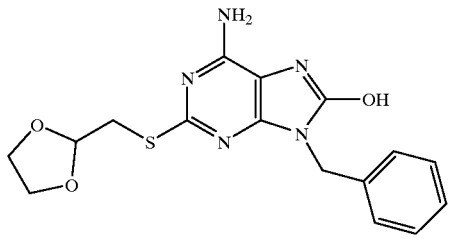

Crude 6-amino-9-benzyl-8-hydroxy-2-mercaptopurine (200 mg, 0.73 mmol) was suspended in dimethylformamide (80 ml). To the suspension were added potassium carbonate (150 mg, 1.1 mmol) and 2-bromomethyl-1,3-dioxolane (0.11 ml, 1.1 mmol) in order. The mixture was stirred at room temperature for 3 hours. The solvent was removed in vacuo, and the residue was purified by silica gel chromatography (3% methanol/chloroform) to give the subject compound (73 mg, yield 28%).

$^1$H-NMR (DMSO-$d_6$) δ: 10.12 (1H, s), 7.31 (5H, m), 6.57 (2H, br s), 5.03 (1H, t, J=4.6 Hz), 4.87 (2H, s), 3.92 (2H, m), 3.78 (2H, m), 3.28 (2H, d, J=5.0 Hz).

Example 47

6-Amino-9-benzyl-8-hydroxy-2-[2-(dimethylamino)ethyl)thiopurine

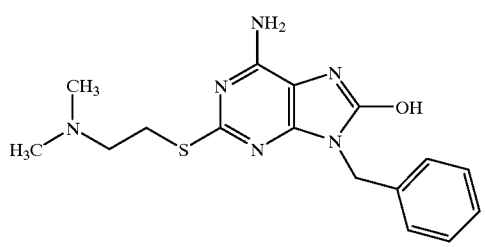

Crude 6-amino-9-benzyl-8-hydroxy-2-mercaptopurine (200 mg, 0.73 mmol) was suspended in dimethylformamide (80 ml). To the suspension were added potassium carbonate (300 mg, 2.2 mmol) and 2-dimethylaminoethylchloride (160 mg, 1.1 mmol) in order. The mixture was stirred at room temperature for 11 hours. The solvent was removed in vacuo, and the residue was purified by silica gel chromatography (10% methanol/chloroform) to give the subject compound (9 mg, yield 4%).

$^1$H-NMR (DMSO-$d_6$) δ: 10.11 (1H, s), 7.29 (5H, m), 6.53 (2H, br s), 4.88 (2H, s), 3.11 (2H, t, J=7.6 Hz), 2.14 (6H, s).

Example 48

6-Amino-9-benzyl-8-hydroxy-2-[(2-methoxyethyl)thio]purine

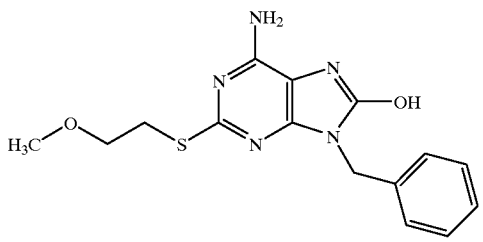

Crude 6-amino-9-benzyl-8-hydroxy-2-mercaptopurine (134 mg, 0.49 mmol) was suspended in dimethylformamide (65 ml). To the suspension were added potassium carbonate (100 mg, 0.72 mmol) and 2-chloroethyl methyl ether (0.067 ml, 0.73 mmol) in order. The mixture was stirred at room temperature for 8 hours. The solvent was removed in vacuo, and the residue was purified by silica gel chromatography (3% methanol/chloroform) to give the subject compound (20 mg, yield 12%).

$^1$H-NMR (DMSO-$d_6$) δ: 10.11 (1H, s), 7.30 (5H, m), 6.55 (2H, br s), 4.87 (2H, s), 3.50 (2H, t, J=6.6 Hz), 3.22 (3H, m), 3.21 (2H, t, J=6.6 Hz).

Example 49

6-Amino-9-benzyl-8-hydroxy-2-(formylmethylthio)purine

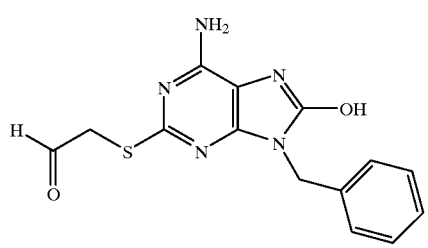

6-Amino-9-benzyl-2-(1,3-dioxolan-2-yl-methyl)thio-8-hydroxypurine (44 mg, 0.12 mmol) was dissolved in a mixture of 3.3N hydrochloric acid (1 ml) and tetrahydrofuran (4 ml). The solution was stirred at 70° C. for 7 hours and then neutralized with aqueous sodium hydrogen carbonate. After removal of tetrahydrofuran in vacuo, the resulting crystals were filtered, washed with water and repulped in methanol to give the subject compound (17 mg, yield 44%).

$^1$H-NMR (DMSO-$d_6$) δ: 10.14 (1H, br s), 9.52 (1H, s), 7.31 (5H, m), 6.60 (2H, br s), 3.81 (2H, s).

Example 50

6-Amino-9-benzyl-8-hydroxy-2-(2-morpholinoethyl)thiopurine

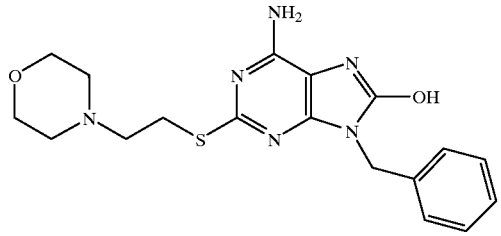

Crude 6-amino-9-benzyl-8-hydroxy-2-mercaptopurine (134 mg, 0.49 mmol) was suspended in dimethylformamide (65 ml). To the suspension were added potassium carbonate (100 mg, 0.72 mmol) and 4-(2-chloroethyl)morpholine (136 mg, 0.73 mmol) in order. The mixture was stirred at room temperature for 8 hours. The solvent was removed in vacuo, and the residue was purified by silica gel chromatography (8% methanol/chloroform) to give the subject compound (34 mg, yield 18%).

$^1$H-NMR (DMSO-d$_6$) δ: 10.12 (1H, s), 7.28 (511, m), 6.53 (2H, br s), 3.51 (4H, m), 3.11 (2H, t, J=7.6 Hz), 2.34 (4H, m).

Example 51

6-Amino-9-benzyl-2-[2-(1,3-dioxolan-2-yl)ethylthio)-8-hydroxypurine

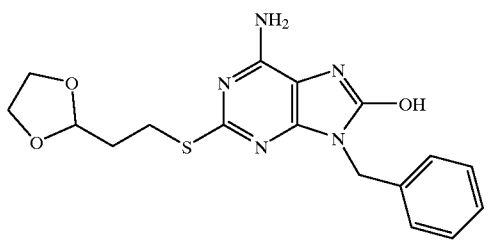

Crude 6-amino-9-benzyl-8-hydroxy-2-mercaptopurine (200 mg, 0.73 mmol) was suspended in dimethylformamide (80 ml). To the suspension were added potassium carbonate (150 mg, 1.1 mmol) and 2-(2-bromoethyl)-1,3-dioxolane (0.14 ml, 1.1 mmol) in order. The mixture was stirred at room temperature for 3 hours. The solvent was removed in vacuo, and the residue was purified by silica gel chromatography (3% methanol/chloroform) to give the subject compound (163 mg, yield 60%).

$^1$H-NMR (DMSO-d$_6$) δ: 10.10 (1H, s), 7.34 (5H, m), 6.52 (2H, br s), 4.89 (1H, t, J=4.3 Hz), 4.87 (2H, s), 3.89 (2H, m), 3.77 (2H, m), 3.05 (2H, t, J=6.9 Hz), 1.96 (2H, m).

Example 52

6-Amino-9-benzyl-2-(2-formylethylthio)-8-hydroxypurine

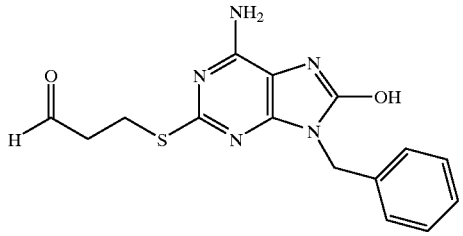

6-Amino-9-benzyl-2-[2-(1,3-dioxolan-2-yl)ethyl)thio-8-hydroxypurine (74 mg, 0.20 mmol) was dissolved in a mixture of 3.3N hydrochloric acid (1 ml) and tetrahydrofuran (4 ml). The solution was stirred at 70° C. for 7 hours and then neutralized with aqueous sodium hydrogen carbonate. After removal of tetrahydrofuran in vacuo, the resulting crystals were filtered, purified by silica gel chromatography (5% methanol/chloroform) to give the subject compound (17 mg, yield 44%).

$^1$H-NMR (DMSO-d$_6$) δ: 10.12 (1H, s), 9.64 (1H, s), 7.30 (5H, m), 6.55 (2H, br s), 4.86 (2H, s), 3.02 (2H, t, J=6.9 Hz), 2.82 (2H, t, J=7.0 Hz).

Example 53

6-Amino-9-benzyl-8-hydroxy-2-[(2-carboxyethyllthio]purine Acid

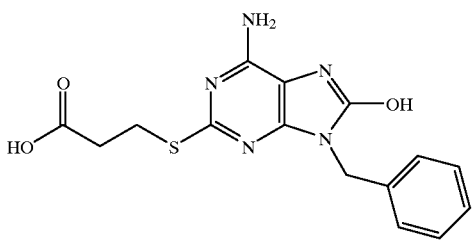

Crude 6-amino-9-benzyl-8-hydroxy-2-mercaptopurine (200 mg, 0.73 mmol) was suspended in dimethylformamide (60 ml). To the suspension were added potassium carbonate (300 mg, 2.2 mmol) and 3-iodopropionic acid (220 mg, 1.1 mmol) in order. The mixture was stirred at room temperature for 3 hours. The solvent was removed in vacuo, and the residue was purified by silica gel chromatography (20% methanol/chloroform) to give the subject compound (38 mg, yield 15%).

$^1$H-NMR (DMSO-d$_6$) δ: 12.27 (1H, s), 10.12 (5H, m), 7.31 (5H, m), 6.55 (2H, br s), 4.87 (2H, s), 3.17 (2H, t, J=6.6 Hz), 2.62 (2H, t, J=6.6 Hz).

Example 54

6-Amino-9-benzyl-8-hydroxy-2-[(2,2,2-trifluoroethyl)thio]purine

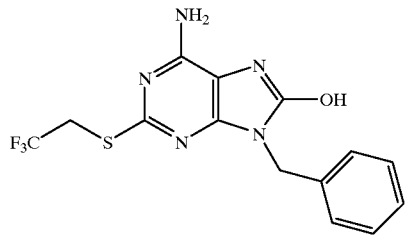

Crude 6-amino-9-benzyl-8-hydroxy-2-mercaptopurine (134 mg, 0.49 mmol) was suspended in dimethylformamide (65 ml). To the suspension were added potassium carbonate (100 mg, 0.7 mmol) and 2-iodo-1,1,1-trifluoroethane (0.07 ml, 0.73 mmol) in order. The mixture was stirred at room temperature for 8 hours. The solvent was removed in vacuo, and the residue was purified by silica gel chromatography (3% methanol/chloroform) to give the subject compound (20 mg, yield 12%).

$^1$H-NMR (DMSO-$d_6$) δ: 10.19 (1H, s), 7.31 (5H, m), 6.70 (2H, br s), 4.90 (2H, s), 4.16 (2H, q, J=10.5 Hz).

Example 55

6-Amino-9-benzyl-2-[(2-fluoroethyl)thio]-8-hydroxypurine

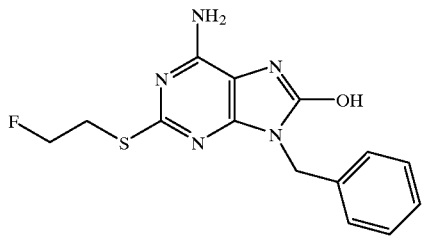

Crude 6-amino-9-benzyl-8-hydroxy-2-mercaptopurine (134 mg, 0.49 mmol) was suspended in dimethylformamide (65 ml). To the suspension were added potassium carbonate (100 mg, 0.72 mmol) and 1-bromo-2-fluoroethane (0.05 ml, 0.7 mmol) in order. The mixture was stirred at room temperature for 4 hours. The solvent was removed in vacuo, and the residue was purified by silica gel chromatography (3% methanol/chloroform) to give the subject compound (100 mg, yield 64%).

$^1$H-NMR (DMSO-$d_6$) δ: 10.14 (1H, s), 7.31 (5H, m), 6.59 (br s), 4.88 (2H, s), 4.63 (1H, t, J=6.6 Hz), 4.46 (1H, t, J=6.6 Hz), 3.31 (4H, m).

Example 56

6-Amino-9-benzyl-2-[(4-chlorobenzyl)thio]-8-hydroxypurine

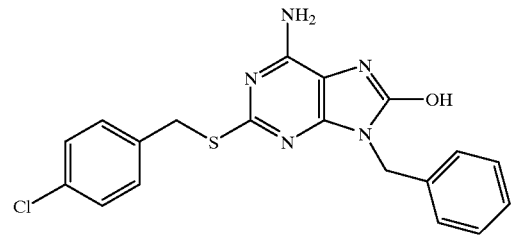

Crude 6-amino-9-benzyl-8-hydroxy-2-mercaptopurine (134 mg, 0.49 mmol) was suspended in dimethylformamide (65 ml). To the suspension were added potassium carbonate (100 mg, 0.72 mmol) and 4-chlorobenzyl chloride (130 mg, 0.81 mmol) in order. The mixture was stirred at room temperature for 8 hours. The solvent was removed in vacuo, and the residue was purified by silica gel chromatography (5% methanol/chloroform) to give the subject compound (74 mg, yield 38%).

$^1$H-NMR (DMSO-$d_6$) δ: 10.13 (1H, s), 7.29 (9H, m), 6.59 (2H, br s), 4.91 (2H, s), 4.26 (s, 2H).

Example 57

6-Amino-9-benzyl-8-hydroxy-2-[(3-methoxybenzyl)thio]purine

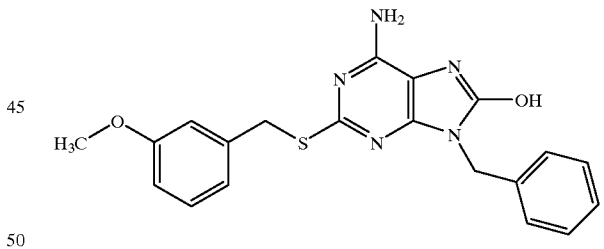

Crude 6-amino-9-benzyl-8-hydroxy-2-mercaptopurine (134 mg, 0.49 mmol) was suspended in dimethylformamide (60 ml). To the suspension were added potassium carbonate (100 mg, 0.72 mmol) and 3-methoxybenzyl chloride (0.1 ml, 0.7 mmol) in order. The mixture was stirred at room temperature for 2 hours. The solvent was removed in vacuo, and the residue was purified by silica gel chromatography (5% methanol/chloroform) to give the subject compound (94 mg, yield 49%).

$^1$H-NMR (DMSO-$d_6$) δ: 10.13 (1H, s), 7.28 (5H, m), 7.15 (1H, m), 6.96 (2H, m), 6.79 (1H, m), 6.59 (2H, br s), 4.89 (2H, s), 4.27 (2H, s), 3.68 (3H, s).

Example 58

6-Amino-9-benzyl-2-cyclohexylmethylthio-8-hydroxypurine

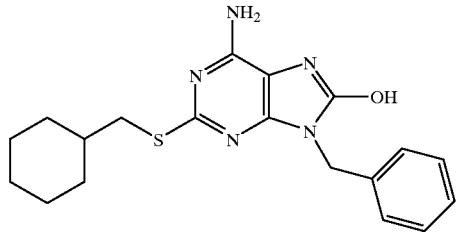

Crude 6-amino-9-benzyl-8-hydroxy-2-mercaptopurine (134 mg, 0.49 mmol) was suspended in dimethylformamide (60 ml). To the suspension were added potassium carbonate (100 mg, 0.72 mmol) and cyclohexylmethyl bromide (0.1 ml, 0.7 mmol) in order. The mixture was stirred at room temperature for 9 hours. The solvent was removed in vacuo, and the residue was purified by silica gel chromatography (3% methanol/chloroform) to give the subject compound (93 mg, yield 51%).

$^1$H-NMR (DMSO-d$_6$) δ: 10.09 (1H, s), 7.30 (5H, m), 6.50 (2H, br s), 4.87 (2H, s), 2.93 (2H, d, J=6.6 Hz), 1.78–0.88 (11H, m).

Example 59

6-Amino-9-benzyl-2-[(3-dimethylaminopropyl)thio]purine

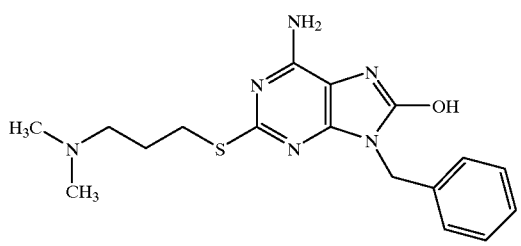

Crude 6-amino-9-benzyl-8-hydroxy-2-mercaptopurine (134 mg, 0.49 mmol) was suspended in dimethylformamide (60 ml). To the suspension were added potassium carbonate (200 mg, 1.44 mmol) and 3-dimethylaminopropyl chloride hydrochloride (114 mg, 0.72 mmol) in order. The mixture was stirred at room temperature for 9 hours. The solvent was removed in vacuo, and the residue was purified by silica gel chromatography (14% methanol/chloroform) to give the subject compound (13 mg, yield 7%).

$^1$H-NMR (DMSO-d$_6$) δ: 10.10 (1H, s), 7.30 (5H, m), 6.50 (2H, br s), 4.87 (2H, s), 3.00 (2H, t, J=7.6 Hz), 2.26 (2H, t, J=7.3 Hz), 2.08 (6H, S), 1.72 (2H, m).

Example 60

3-(6-Amino-9-benzyl-8-hydroxy-2-purinyl)thio-1-propanol

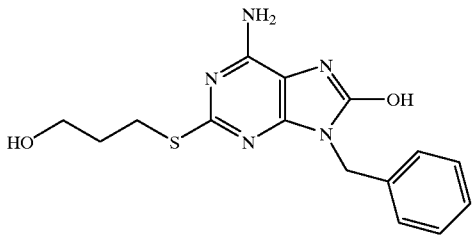

Crude 6-amino-9-benzyl-8-hydroxy-2-mercaptopurine (134 mg, 0.49 mmol) was suspended in dimethylformamide (60 ml). To the suspension were added potassium carbonate (100 mg, 0.72 mmol) and 3-bromo-1-propanol (0.07 ml, 0.7 mmol) in order. The mixture was stirred at room temperature for 3 hours. The solvent was removed in vacuo, and the residue was purified by silica gel chromatography (4% methanol/chloroform) to give the subject compound (64 mg, yield 39%).

$^1$H-NMR (DMSO-d$_6$) δ: 10.09 (1H, s), 7.31 (5H, m), 6.51 (2H, br s), 4.87 (2H, s), 4.51 (1H, t, J=5.3 Hz), 3.48 (2H, q, J=5.6 Hz), 3.05 (2H, t, J=6.9 Hz), 1.75 (2H, m).

Example 61

6-Amino-9-benzyl-2-(3-chlorobenzyl)thio-8-hydroxypurine

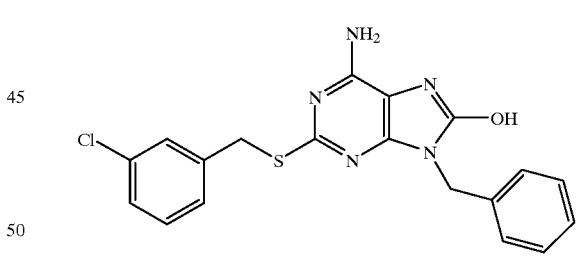

Crude 6-amino-9-benzyl-8-hydroxy-2-mercaptopurine (134 mg, 0.49 mmol) was suspended in dimethylformamide (60 ml). To the suspension were added potassium carbonate (100 mg, 0.72 mmol) and 3-chlorobenzyl chloride (0.09 ml, 0.7 mmol) in order. The mixture was stirred at room temperature for 5 hours. The solvent was removed in vacuo, and the residue was purified by silica gel chromatography (3% methanol/chloroform) to give the subject compound (92 mg, yield 47%).

$^1$H-NMR (DMSO-d$_6$) δ: 10.14 (1H, s), 7.45 (1H, m), 7.27 (5H, m), 6.61 (2H, br s), 4.90 (2H, s), 4.30 (2H, s).

Example 62

6-Amino-9-benzyl-8-hydroxy-2-[3-(methoxycarbonyl)propyl]-thiopurine

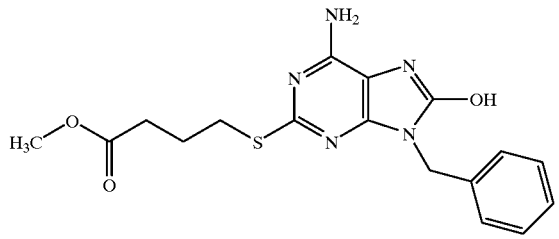

Crude 6-amino-9-benzyl-8-hydroxy-2-mercaptopurine (200 mg, 0.73 mmol) was suspended in dimethylformamide (60 ml). To the suspension were added potassium carbonate (150 mg, 1.1 mmol) and methyl 4-chlorobutylate (0.13 ml, 1.1 mmol) in order. The mixture was stirred at room temperature for 3 hours. The solvent was removed in vacuo, and the residue was purified by silica gel chromatography (2% methanol/chloroform) to give the subject compound (97 mg, yield 36%).

$^1$H-NMR (DMSO-$d_6$) δ: 10.11 (1H, s), 7.30 (5H, m), 6.53 (2H, br s), 4.88 (2H, s), 3.57 (3H, s), 3.03 (2H, t, J=7.2 Hz), 2.39 (2H, t, J=7.2 Hz), 1.86 (2H, m).

Example 63

6-Amino-9-benzyl-8-hydroxy-2-[(2-phenylethyl)thio]purine

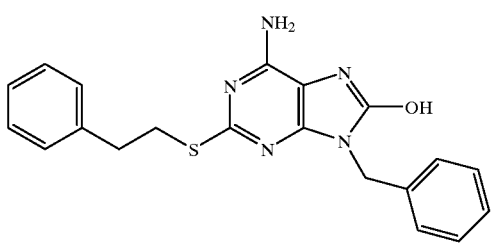

Crude 6-amino-9-benzyl-8-hydroxy-2-mercaptopurine (134 mg, 0.49 mmol) was suspended in dimethylformamide (60 ml). To the suspension were added potassium carbonate (100 mg, 0.72 mmol) and 2-bromoethylbenzene (0.10 ml, 0.73 mmol) in order. The mixture was stirred at room temperature for 4 hours. The solvent was removed in vacuo, and the residue was purified by silica gel chromatography (3% methanol/chloroform) to give the subject compound (117 mg, yield 63%).

$^1$H-NMR (DMSO-$d_6$) δ: 10.13 (1H, s), 7.28 (5H, m), 6.56 (2H, br s), 4.92 (2H, s), 3.22 (2H, m), 2.89 (2H, t, J=6.6 Hz).

Example 64

4-(6-Amino-9-benzyl-8-hydroxy-2-purinyl)thiobutyric Acid

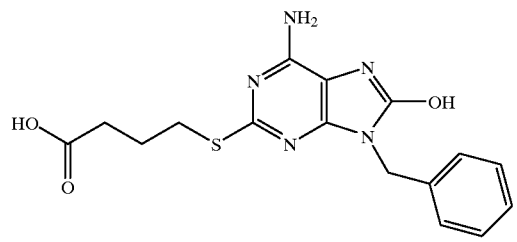

To a methanol solution (5 ml) containing 500 mg of sodium hydroxide was added 6-amino-9-benzyl-8-hydroxy-2-[(methoxycarbonylpropyl)]thiopurine (60 mg, 0.16 mmol). The solution was refluxed under heating for 5 hours, and neutralized with 2N hydrochloric acid and then aqueous sodium hydrogen carbonate. After removal of the solvent in vacuo, the resulting crystals were filtered and washed with water to give the subject compound (5 mg, yield 9%).

$^1$H-NMR (DMSO-$d_6$) δ: 7.31 (5H, m), 6.90 (2H, br s), 3.02 (2H, m), 2.09 (2H, m), 1.79 (2H, m).

Example 65

6-Amino-9-benzyl-8-hydroxy-2-[(4-methoxybenzyl)thio]purine

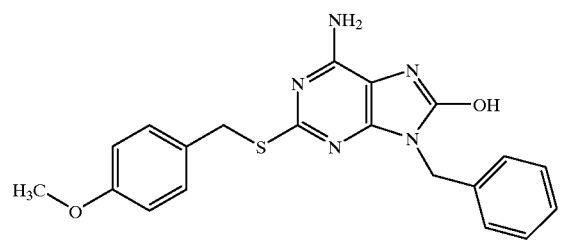

Crude 6-amino-9-benzyl-8-hydroxy-2-mercaptopurine (134 mg, 0.49 mmol) was suspended in dimethylformamide (60 ml). To the suspension were added potassium carbonate (100 mg, 0.72 mmol) and 4-methoxybenzyl chloride (0.098 ml, 0.72 mmol) in order. The mixture was stirred at room temperature for 3 hours. The solvent was removed in vacuo, and the residue was purified by silica gel chromatography (3% methanol/chloroform) to give the subject compound (80 mg, yield 41%).

$^1$H-NMR (DMSO-$d_6$) δ: 10.13 (1H, s), 7.28 (5H, m), 6.73 (2H, t, J=8.9 Hz), 6.57 (2H, br s), 4.92 (2H, s), 4.22 (2H, s), 3.69 (3H, s).

Example 66

6-Amino-9-benzyl-2-(2-cyanoethyl)thio-8-hydroxypurine

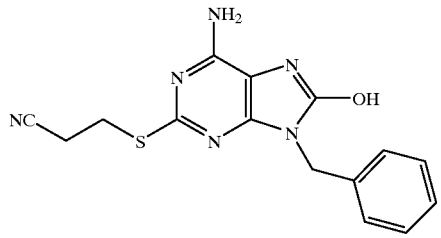

Crude 6-amino-9-benzyl-8-hydroxy-2-mercaptopurine (134 mg, 0.49 mmol) was suspended in dimethylformamide (60 ml). To the suspension were added potassium carbonate (100 mg, 0.72 mmol) and 3-chloropropionitrile (65 mg, 0.73 mmol) in order. The mixture was stirred at room temperature for 3 hours. The solvent was removed in vacuo, and to the residue was added water. The mixture was extracted with chloroform and the organic layer was dried on sodium sulfate. After removal of the solvent in vacuo, the residue was purified by silica gel chromatography (5% methanol/chloroform) to give the subject compound (72 mg, yield 45%).

$^1$H-NMR (DMSO-$d_6$) δ: 10.17 (1H, br s), 7.36–7.25 (5H, m), 6.63 (2H, br s), 4.90 (2H, s), 3.24 (2H, t, J=6.0 Hz), 2.88 (2H, t, J=6.0 Hz).

Example 67

6-Amino-9-benzyl-2-cyanomethylthio-8-hydroxypurine

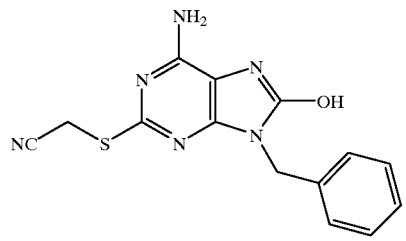

Crude 6-amino-9-benzyl-8-hydroxy-2-mercaptopurine (150 mg, 0.55 mmol) was suspended in dimethylformamide (10 ml). To the suspension were added potassium carbonate (81 mg, 0.59 mmol) and chloroacetonitrile (44 mg, 0.59 mmol) in order. The mixture was stirred at room temperature for 3 hours. The solvent was removed in vacuo, and to the residue was added water. The mixture was extracted with chloroform and the organic layer was dried on sodium sulfate. After removal of the solvent in vacuo, the residue was purified by silica gel chromatography (1% ammonia, 5% methanol/chloroform) to give the subject compound (58 mg, yield 25%).

$^1$H-NMR (DMSO-$d_6$) δ: 10.21 (1H, br s), 7.41–7.24 (5H, m), 6.71 (2H, br s), 4.91 (2H, s), 4.15 (2H, s).

Example 68

6-Amino-9-benzyl-2-(3-cyanopropyl)thio-8-hydroxypurine

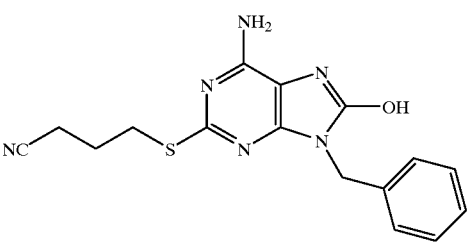

Crude 6-amino-9-benzyl-8-hydroxy-2-mercaptopurine (150 mg, 0.55 mmol) was suspended in dimethylformamide (10 ml). To the suspension were added potassium carbonate (202 mg, 1.46 mmol) and 4-chlorobutyronitrile (152 mg, 1.46 mmol) in order. The mixture was stirred at room temperature for 3 hours. The solvent was removed in vacuo, and to the residue was added water. The mixture was extracted with chloroform and the organic layer was dried on sodium sulfate. After removal of the solvent in vacuo, the residue was purified by silica gel chromatography (5% methanol/chloroform) to give the subject compound (71 mg, yield 29%).

$^1$H-NMR (DMSO-$d_6$) δ: 10.13 (1H, br s), 7.36–7.22 (5H, m), 6.55 (2H, br s), 4.91 (2H, s), 3.08 (2H, t, J=7.0 Hz), 2.56 (2H, t, J=7.0 Hz), 1.91 (2H, m).

Example 69

6-Amino-9-benzyl-8-hydroxy-2-(4-methylthiomethyl)thiopurine

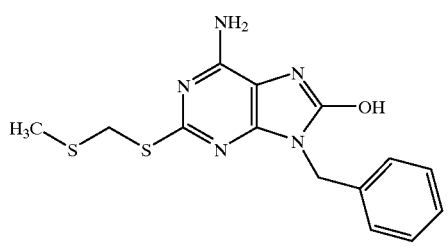

Crude 6-amino-9-benzyl-8-hydroxy-2-mercaptopurine (134 mg, 0.49 mmol) was suspended in dimethylformamide (60 ml). To the suspension were added potassium carbonate (100 mg, 0.72 mmol) and chloromethyl methyl sulfide (0.06 ml, 0.72 mmol) in order. The mixture was stirred at room temperature for 4 hours. The solvent was removed in vacuo, and the residue was purified by silica gel chromatography (3% methanol/chloroform) to give the subject compound (83 mg, yield 51%).

$^1$H-NMR (DMSO-$d_6$) δ: 10.14 (1H, s), 7.33 (5H, m), 6.59 (2H, br s), 4.88 (2H, s), 4.30 (2H, s), 2.11 (3H, s).

Example 70

6-Amino-9-benzyl-2-(benzyloxymethyl)thio-8-hydroxypurine

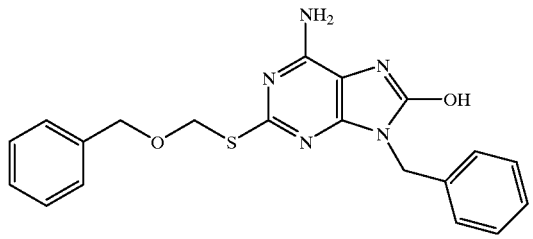

Crude 6-amino-9-benzyl-8-hydroxy-2-mercaptopurine (134 mg, 0.49 mmol) was suspended in dimethylformamide (60 ml). To the suspension were added potassium carbonate (100 mg, 0.72 mmol) and benzyloxymethyl chloride (0.1 ml, 0.7 mmol) in order. The mixture was stirred at room temperature for 4 hours. The solvent was removed in vacuo, and the residue was purified by silica gel chromatography (3% methanol/chloroform) to give the subject compound (90 mg, yield 47%).

$^1$H-NMR (DMSO-$d_6$) δ: 10.15 (1H, s), 7.30 (10H, m), 6.61 (2H, br s), 4.88 (2H, s), 4.52 (2H, s).

Example 71

6-Amino-9-benzyl-8-hydroxy-2-[3-(1-piperazinyl)propyl]thiopurine

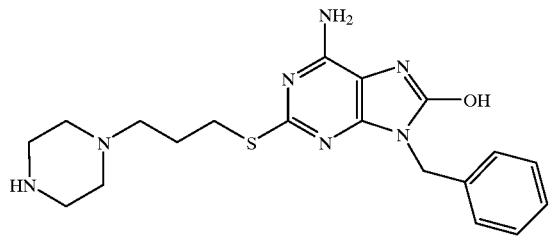

Crude 6-amino-9-benzyl-8-hydroxy-2-mercaptopurine (134 mg, 0.49 mmol) was suspended in dimethylformamide (60 ml). To the suspension were added potassium carbonate (100 mg, 0.72 mmol) and 1-(3-chloropropyl)piperazine (179 mg, 0.73 mmol) in order. The mixture was stirred at room temperature for 2 hours. The solvent was removed in vacuo, and the residue was purified by silica gel chromatography (20% methanol/chloroform) to give the subject compound (10 mg, yield 5%).

$^1$H-NMR (DMSO-$d_6$) δ: 7.31 (5H, m), 6.62 (2H, br s), 4.87 (2H, s), 3.04–2.94 (6H, m), 2.43–2.37 (6H, m), 1.76 (2H, m).

Example 72

6-Amino-9-benzyl-8-hydroxy-2-[2-(methylthio)ethyl]thiopurine

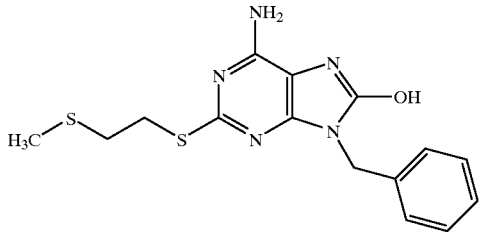

Crude 6-amino-9-benzyl-8-hydroxy-2-mercaptopurine (134 mg, 0.49 mmol) was suspended in dimethylformamide (60 ml). To the suspension were added potassium carbonate (100 mg, 0.72 mmol) and chloromethyl ethyl sulfide (0.08 ml, 0.7 mmol) in order. The mixture was stirred at room temperature for 2 hours. The solvent was removed in vacuo, and the residue was purified by silica gel chromatography (3% methanol/chloroform) to give the subject compound (28 mg, yield 16%).

$^1$H-NMR (DMSO-$d_6$) δ: 10.11 (1H, s), 7.31 (5H, m), 6.54 (2H, br s), 4.88 (2H, s), 3.21 (2H, m), 2.73 (2H, m), 2.07 (3H, s).

Example 73

4-[(6-Amino-9-henzyl-8-hydroxy-2-purinyl)thio]butanol

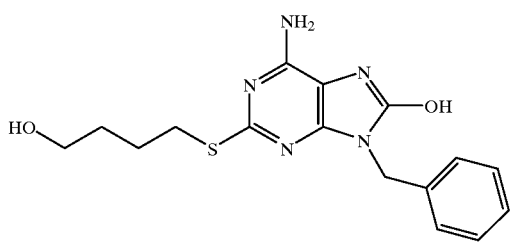

Crude 6-amino-9-benzyl-8-hydroxy-2-mercaptopurine (470 mg, 1.7 mmol) was suspended in dimethylformamide (80 ml). To the suspension were added potassium carbonate (350 mg, 2.5 mmol) and 4-chlorobutanol (0.25 ml, 2.5 mmol) in order. The mixture was stirred at room temperature for 4 hours. The solvent was removed in vacuo, and the residue was purified by silica gel chromatography (7% methanol/chloroform) to give the subject compound (29 mg, yield 5%).

$^1$H-NMR (DMSO-$d_6$) δ: 10.09 (1H, s), 7.31 (5H, m), 6.50 (2H, br s), 4.87 (2H, s), 4.40 (1H, t, J=5.3 Hz), 3.39 (2H, q, J=5.3 Hz), 3.02 (2H, t, J=6.9 Hz), 1.67–1.48 (4H, m).

Example 74

6-Amino-9-benzyl-8-hydroxy-2-{2-(2-methoxyethoxy)ethyl]thio}purine

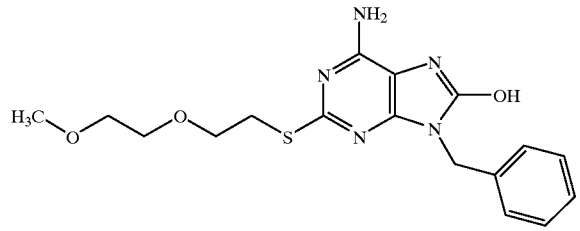

Crude 6-amino-9-benzyl-8-hydroxy-2-mercaptopurine (350 mg, 1.7 mmol) was suspended in dimethylformamide (100 ml). To the suspension were added potassium carbonate (350 mg, 2.5 mmol) and 1-(2-chloroethoxy)-2-methoxyethane (1.04 g, 2.6 mmol) in order. The mixture was stirred at room temperature for 2 hours. The solvent was removed in vacuo, and the residue was purified by silica gel chromatography (7% methanol/chloroform) to give the subject compound (69 mg, yield 11%).

$^1$H-NMR (DMSO-d$_6$) δ: 10.11 (1H, s), 7.30 (5H, m), 6.54 (2H, br s), 4.88 (2H, s), 3.58 (2H, t, J=6.6 Hz), 3.49 (2H, t, J=2.6 Hz), 3.40 (2H, t, J=5.9 Hz), 3.22 (3H, s), 3.18 (2H, t, J=6.6 Hz).

Example 75

6-Amino-9-benzyl-8-hydroxy-2-{[2-(2-hydroxyethoxy)ethyl]thio}purine

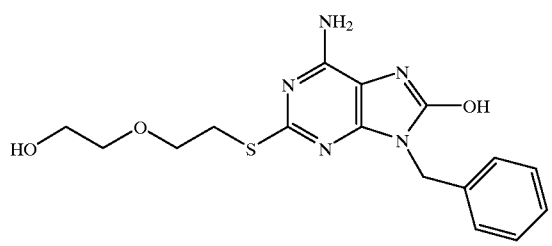

Crude 6-amino-9-benzyl-8-hydroxy-2-mercaptopurine (470 mg, 1.7 mmol) was suspended in dimethylformamide (100 ml). To the suspension were added potassium carbonate (350 mg, 2.5 mmol) and 2-(2-chloroethoxy)ethanol (0.27 ml, 2.6 mmol) in order. The mixture was stirred at room temperature for 4 hours. The solvent was removed in vacuo and the residue was purified by silica gel chromatography (7% methanol/chloroform) to give the subject compound (159 mg, yield 27%).

$^1$H-NMR (DMSO-d$_6$) δ: 10.11 (1H, s), 7.31 (5H, m), 6.54 (2H, br s), 4.88 (2H, s), 4.59 (1H, t, J=5.6 Hz), 3.48–3.39 (4H, m), 3.19 (2H, t, J=6.6 Hz).

Example 76

6-Amino-9-benzyl-8-hydroxy-2-{[2-(2-ethoxyethoxy)ethyl]thio}purine

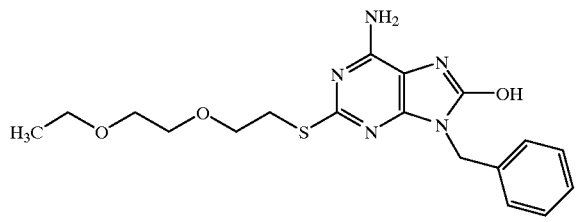

Crude 6-amino-9-benzyl-8-hydroxy-2-mercaptopurine (470 mg, 1.7 mmol) was suspended in dimethylformamide (100 ml). To the suspension were added potassium carbonate (350 mg, 2.5 mmol) and 1-ethoxy-2-(2-bromoethoxy)ethane (505 mg, 2.6 mmol) in order. The mixture was stirred at room temperature for 2 hours. The solvent was removed in vacuo, and the residue was purified by silica gel chromatography (1% methanol/chloroform) to give the subject compound (147 mg, yield 22%).

$^1$H-NMR (DMSO-d$_6$) δ: 10.11 (1H, s), 7.31 (5H, m), 6.54 (2H, br s), 4.88 (2H, s), 3.58 (2H, t, J=6.9 Hz), 3.51–3.36 (6H, m), 3.18 (2H, t, J=6.9 Hz), 1.07 (3H, t, J=6.9 Hz).

Example 77

6-Amino-9-benzyl-8-hydroxy-2-(3-ethoxypropyl)thiopurine

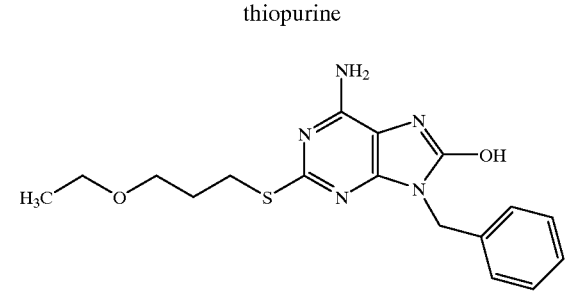

Crude 6-amino-9-benzyl-8-hydroxy-2-mercaptopurine (80 mg, 0.65 mmol) was suspended in dimethylformamide (60 ml). To the suspension were added potassium carbonate (150 mg, 1.1 mmol) and 2-ethoxypropyl p-toluenesulfonate (280 mg, 1.1 mmol) in order. The mixture was stirred at room temperature for 4 hours. The solvent was removed in vacuo, and the residue was purified by silica gel chromatography (5% methanol/chloroform) to give the subject compound (69 mg, yield 30%).

$^1$H-NMR (DMSO-d$_6$) δ: 10.09 (1H, s), 7.31 (5H, m), 6.51 (2H, br s), 4.87 (2H, s), 3.44–3.34 (4H, m), 3.03 (2H, t, J=8.9 Hz), 1.83 (2H, m), 1.08 (3H, t, J=6.9 Hz).

Example 78

6-Amino-9-benzyl-8-hydroxy-2-{[2-(2-hydroxyethylthio)ethyl]thio}purine

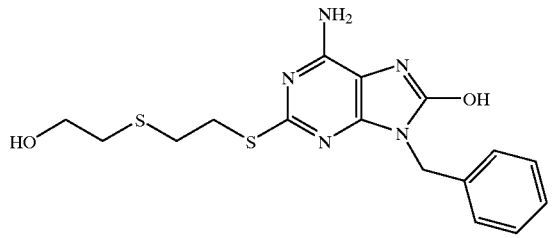

Crude 6-amino-9-benzyl-8-hydroxy-2-mercaptopurine (134 mg, 0.49 mmol) was suspended in dimethylformamide (50 ml). To the suspension were added potassium carbonate (100 mg, 0.73 mmol) and 2-(2-chloroethyl)thioethanol (170 mg, 1.2 mmol) in order. The mixture was stirred at room temperature for 24 hours. To the reaction mixture were added 2N hydrochloric acid and then 28% aqueous ammonia. The mixture was extracted with chloroform, the organic layer was dried on magnesium sulfate and then the solvent was removed in vacuo. The residue was purified by silica gel chromatography (5% methanol/chloroform) to give the subject compound (17 mg, yield 6%).

$^1$H-NMR (DMSO-d$_6$) δ: 10.12 (1H, s), 7.31 (5H, m), 6.53 (2H, br s), 4.87 (2H, s), 4.82 (1H, t, J=5.6 Hz), 3.53 (2H, t, J=6.6 Hz), 3.18 (2H, m), 2.77 (2H, t, J=8.2 Hz), 2.63 (2H, t, J=6.6 Hz).

Example 79

6-Amino-9-benzyl-8-hydroxy-2-(2-methoxyethyl)aminopurine

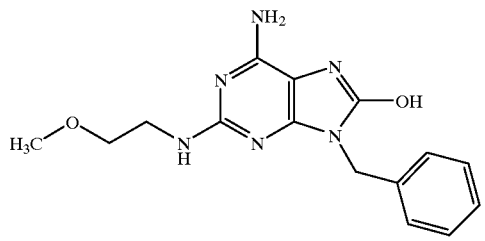

6-Amino-9-benzyl-8-methoxy-2-(2-methoxyethyl)aminopurine (26 mg, 0.079 mmol) in concentrated hydrochloric acid (20 ml) was stirred at room temperature for 7 hours. The reaction mixture was made basic with 28% aqueous ammonia. The resulting crystals were filtered to give the subject compound (18 mg, yield 73%).

$^1$H-NMR (DMSO-d$_6$) δ: 9.66 (1H, br s), 7.34–7.26 (5H, m), 6.14 (1H, t, J=4.8 Hz), 6.05 (2H, br s), 4.80 (2H, s), 3.39–3.34 (4H, m), 3.22 (3H, s).

Example 80

6-Amino-9-benzyl-2-(2-ethoxyethoxy)-8-hydroxypurine

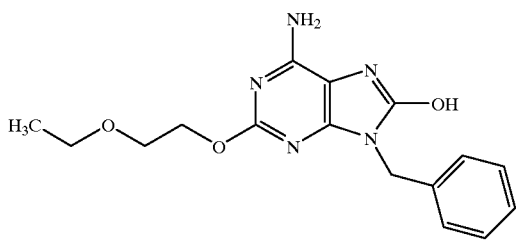

6-Amino-9-benzyl-2-(2-ethoxyethoxy)-8-methoxypurine (110 mg, 0.32 mmol) in concentrated hydrochloric acid (20 ml) was stirred at room temperature for 12 hours. The reaction mixture was evaporated in vacuo to dryness and then 28% aqueous ammonia was added thereto. The resulting crystals were filtered to give the subject compound (88 mg, yield 84%).

$^1$H-NMR (DMSO-d$_6$) δ: 9.98(1H, br s), 7.35–7.23(5H, m), 6.48(2H, br s), 4.86(2H, s), 4.25(2H, t, J=4.6 Hz), 3.62(2H, t, J=4.6 Hz), 3.45(2H, q, J=7.0 Hz), 1.11(3H, t, J=7.0 Hz).

Example 81

6-Amino-9-(4-fluorobenzyl)-8-hydroxy-2-(2-methoxyethoxy)purine

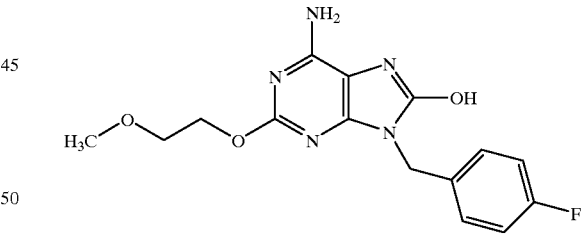

6-Amino-9-(4-fluorobenzyl)-8-methoxy-2-(2-methoxyethoxy)purine (49 mg, 0.14 mmol) in concentrated hydrochloric acid (20 ml) was stirred for 12 hours. The reaction mixture was evaporated in vacuo to dryness and then 28% aqueous ammonia was added thereto. The resulting crystals were filtered to give the subject compound (36 mg, yield 77%).

$^1$H-NMR(DMSO-d$_6$) δ: 9.97(1H, br s), 7.35(2H, m), 7.14(2H, m), 6.48(2H, br s), 4.84(2H, s), 4.27(2H, t, J=4.6 Hz), 3.59(2H, t, J=4.6 Hz), 3.28(3H, s).

Example 82

6-Amino-9-(4-fluorobenzyl)-8-hydroxy-2-methylthiopurine

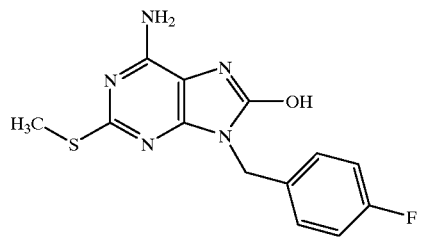

6-amino-9-(4-fluorobenzyl)-8-hydroxy-2-mercaptopurine (200 mg, 0.687 mmol) was suspended in methanol (20 ml). To the suspension were added potassium carbonate (190 mg, 1.37 mmol) and methyl iodide (975 mg, 6.87 mmol) in order. The mixture was stirred at room temperature for 30 minutes. The reaction mixture were evaporated in vacuo to dryness and extracted with chloroform. The organic layer was dried on sodium sulfate. After removal of the solvent in vacuo, the residue was purified by silica gel chromatography (3% methanol/chloroform) to give the subject compound (63 mg, yield 30%).

$^1$H-NMR (DMSO-$d_6$) δ: 10.11(1H, br s), 7.37(2H, m), 7.15(2H, m), 6.53(2H, br s), 4.87(2H, s), 2.43(3H, s).

Example 83

6-Amino-9-benzyl-2-(3-hydroxypropoxy)-8-hydroxypurine

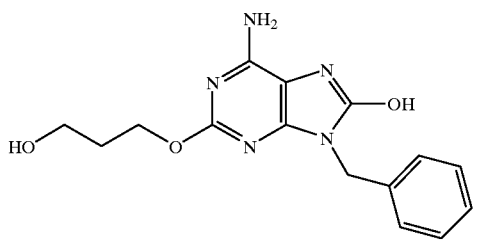

6-Amino-9-benzyl-2-(3-hydroxypropoxy)-8-methoxypurine (83 mg, 0.25 mmol) in concentrated hydrochloric acid (5 ml) was stirred at room temperature for 4 hours. The reaction mixture was neutralized with 28% aqueous ammonia and the resulting crystals were filtered and washed with water to give the subject compound (40 mg, yield 51%).

$^1$H-NMR(DMSO-$d_6$) δ: 9.95(1H, br s), 7.30(5H, m), 6.45(2H, br s), 4.85(2H, s), 4.50(1H, t, J=5.0 Hz), 4.20(2H, t, J=6.0 Hz), 3.51(2H, q, J=5.0 Hz), 1.79(2H, m).

Example 84

6-Amino-9-benzyl-8-hydroxy-2-(3-ethoxypropoxy)npurine

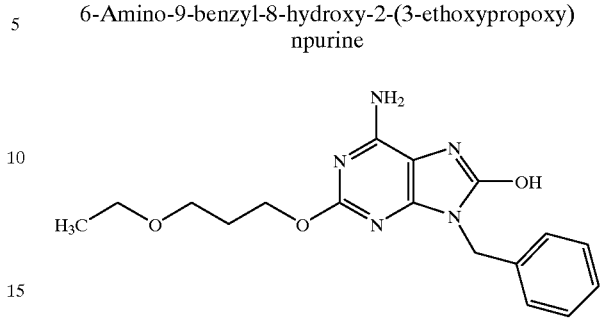

6-Amino-9-benzyl-2-(3-ethoxypropoxy)-8-methoxypurine (149 mg, 0.417 mmol) in concentrated hydrochloric acid (20 ml) was stirred at room temperature for 12 hours. The reaction mixture was evaporated in vacuo to dryness and neutralized with 28% aqueous ammonia. The resulting crystals were filtered to give the subject compound (112 mg, yield 78%).

$^1$H-NMR(DMSO-$d_6$) δ: 9.97(1H, br s), 7.31–7.23(5H, m), 6.45(2H, br s), 4.84(2H, s), 4.17(2H, t, J=6.6 Hz), 3.44(2H, t, J=6.6 Hz), 3.38(2H, q, J=7.0 Hz), 1.85(2H, m), 1.08(3H, t, J=7.0 Hz).

Example 85

6-Amino-9-benzyl-8-hydroxy-2-(4-hydroxybutoxy)purine

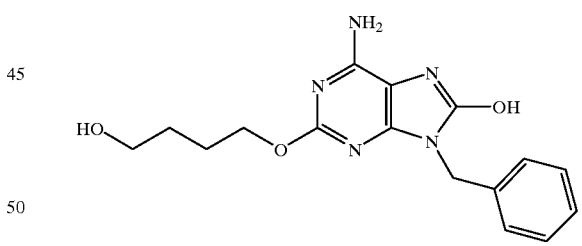

6-Amino-9-benzyl-2-(4-hydroxybutoxy)-8-methoxypurine (114 mg, 0.332 mmol) in concentrated hydrochloric acid (20 ml) was stirred at room temperature for 12 hours. The reaction mixture was evaporated in vacuo to dryness and to the residue was added aqueous ammonia. The resulting crystals were filtered to give the subject compound (80 mg, yield 73%).

$^1$H-NMR(DMSO-$d_6$) δ: 9.95(1H, br s), 7.33–7.24(5H, m), 6.45(2H, br s), 4.85(2H, s), 4.43(1H, t, J=5.1 Hz), 4.14(2H, t, J=6.6 Hz), 3.42(2H, m), 1.67(2H, m), 1.50(2H, m).

Example 86

6-Amino-9-benzyl-8-hydroxy-2-(2-methylthioethoxy)purine

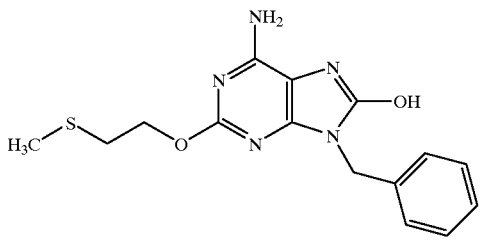

6-amino-9-benzyl-2-chloro-8-methoxypurine (190 mg, 0.56 mmol) was added to 2-methylthioethanol (3 ml) containing sodium (110 mg, 4.78 mmol). The mixture was heated for 2 hours. Thereto were added 2N hydrochloric acid and 28% aqueous ammonia in order. The mixture was extracted with 3% methanol/chloroform and the organic layer was dried on sodium sulfate. After removal of the solvent in vacuo, the residue was purified by silica gel chromatography (3% methanol/chloroform) to give the subject compound (59 mg, yield 27%).

$^1$H-NMR(DMSO-$d_6$) δ: 9.97(1H, s), 7.30(5H, m), 6.49 (2H, br s), 4.85(2H, s), 4.30(2H, t, J=7.0 Hz), 2.76(2H, t, J=6.9 Hz), 2.10(3H, 5).

Example 87

6-Amino-9-benzyl-8-hydroxy-2-(2-hydroxyethoxy)purine

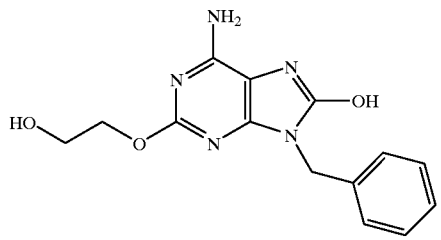

6-Amino-9-benzyl-2-(2-hydroxyethoxy)-8-methoxypurine (70 mg, 0.22 mmol) in concentrated hydrochloric acid (5 ml) was stirred at room temperature for 5 hours. The reaction mixture was neutralized with 28% aqueous ammonia and the resulting crystals were filtered and washed with water to give the subject compound (38 mg, yield 57%).

$^1$H-NMR(DMSO-$d_6$) δ: 9.89(1H, br s), 7.30(5H, m), 6.46(2H, br s), 4.85(2H, s), 4.79(1H, t, J=5.6 Hz), 4.15(2H, t, J=4.9 Hz), 3.65(2H, m).

Example 88

6-Amino-9-benzyl-8-hydroxy-2-(2-methoxyethoxy)purine

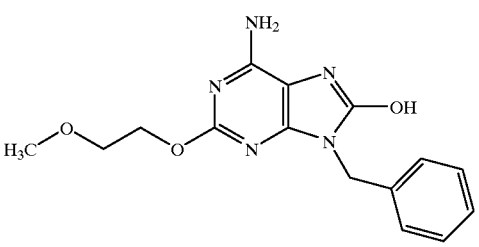

6-Amino-9-benzyl-8-methoxy-2-(2-methoxyethoxy)purine (21 mg, 0.064 mmol) in concentrated hydrochloric acid (20 ml) was stirred at room temperature for 5 hours. The reaction mixture was evaporated in vacuo to dryness and 28% aqueous ammonia was added to the residue. The resulting crystals were filtered and washed with water to give the subject compound (17 mg, yield 84%).

$^1$H-NMR(DMSO-$d_6$) δ: 9.97(1H, br s), 7.35–7.23(5H, m), 6.48(2H, br s), 4.86(2H, s), 4.26(2H, t, J 4.6 Hz), 3.58(2H, t, J=4.6 Hz), 3.27(3H, s).

Example 89

6-Amino-2-(2-aminoethylthio)-9-benzyl-8-hydroxypurine

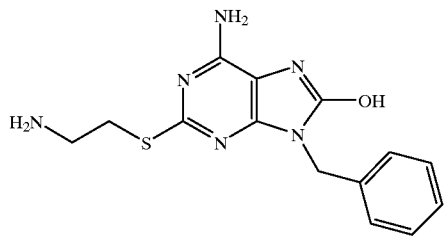

6-Amino-9-benzyl-8-hydroxy-2-(2-phthalimidoethylthio)purine (78 mg, 0.18 mmol) was suspended in 1M hydrazine monohydrate (10 ml). The suspension was stirred at room temperature for 9 hours. The reaction mixture was evaporated in vacuo to dryness and to the residue was added 2N hydrochloric acid. Insoluble materials were filtered off and the filtrate was neutralized with 28% aqueous ammonia and extracted with ethyl acetate. The organic layer was dried on magnesium sulfate and evaporated in vacuo to dryness to give the subject compound (4 mg, yield 7%).

$^1$H-NMR(DMSO-$d_6$) δ: 7.31(7H, m), 6.53(2H, br s), 4.88(2H, s), 3.05(2H, t, J=6.3 Hz), 2.76(2H, t, J=6.6 Hz).

Example 90

6-Amino-2-butylthio-9-(4-fluorobenzyl)-8-hydroxypurine

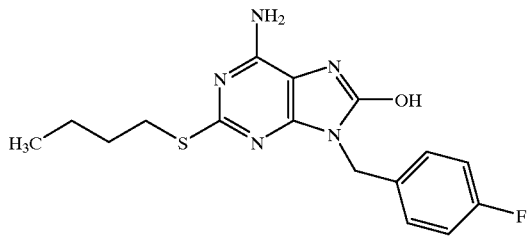

6-Amino-9-(4-fluorobenzyl)-8-hydroxy-2-thiopurine (200 mg, 0.687 mmol) and potassium carbonate (190 mg, 1.37 mmol) were dissolved in dimethylformamide (10 ml). Butyl bromide (941 mg, 6.87 mnmol) was added thereto and the mixture was stirred at room temperature for 4 hours. The reaction mixture was evaporated in vacuo to dryness. Water was added to the residue and the solution was extracted with chloroform. The organic layer was dried on magnesium sulfate and evaporated in vacuo to dryness. The residue was purified by silica gel chromatography (2% methanol/chloroform) to give the subject compound (38 mg, yield 16%).

$^1$H-NMR(DMSO-d$_6$) δ: 10.10(1H, br s), 7.35(2H, m), 7.14(2H, m), 6.51(2H, br s), 4.87(2H, s), 3.00(2H, t, J=7.1 Hz), 1.56(2H, m), 1.36(2H, m), 0.86(3H, t, J=7.3 Hz).

Example 91

6-Amino-9-(4-fluorobenzyl)-8-hydroxy-2-(2-methoxyethylthio)purine

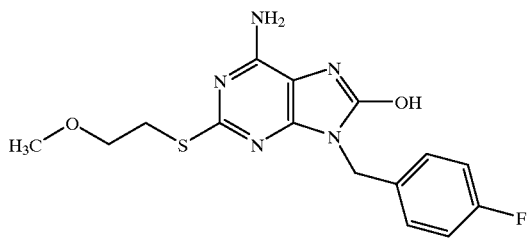

6-Amino-9-(4-fluorobenzyl)-8-hydroxy-2-thiopurine (200 mg, 0.687 mmol) and potassium carbonate (190 mg, 1.37 mmol) were dissolved in dimethylformamide (10 ml). 2-Methoxyethyl chloride (649 mg, 6.87 mmol) was added thereto and the mixture was stirred at room temperature for 2 hours. The reaction mixture was evaporated in vacuo to dryness. Water was added to the residue and the solution was extracted with chloroform. The organic layer was dried on magnesium sulfate and evaporated in vacuo to dryness. The residue was purified by silica gel chromatography (2% methanol/chloroform) to give the subject compound (50 mg, yield 21%).

$^1$H-NMR(DMSO-d$_6$) δ: 10.12(1H, br s), 7.34(2H, m), 7.15(2H, m), 6.56(2H, br s), 4.87(2H, s), 3.51(2H, t, J=6.8 Hz), 3.24(3H, s), 3.20(2H, t, J=6.8 Hz).

Example 92

Inducing Activity for Biosynthesis of Interferon

Experimental Method

1) Animals

C3H/HeJ male mice (5–8 weeks) were purchased from Clea Japan Inc.

2) Reagents

MEM (Osaka University, Microbial Research Center), FCS (GIBCO Co. or Filtron Pty Ltd.), DMSO (Nacalai Tesque Inc.)

3) Test Compounds

About 1 mg of each test compound was accurately weighed and was dissolved in dimethyl sulfoxide (DMSO) to prepare 1 mM or 10 mM solution of the test compound. The solution was further diluted 500 times with a culture medium (MEM+10%FCS) and the obtained solution was used as the sample solution in the following tests.

4) Preparation of Spleen Cells and Supernatant of the Cell Culture Medium

After pre-feeding for a week, spleens of 2 or 3 mice were removed. The spleen was put in PBS(−) solution and a homogenous cell suspension was prepared by pipetting cells from the spleen. The cell suspension was centrifuged (1200 rpm, 5 min., 4° C.) to remove the supernatant. Thereto was quickly added 0.2% ice cold NaCl solution (4 ml) under ice cooling to make a suspension. After 30 seconds 1.6% (4 ml) ice-cold NaCl solution was added to the suspension and the mixture was centrifuged to remove the supernatant. The residue was suspended in PBS(−) solution (10 ml) and the suspension was centrifuged to remove the supernatant. The residue was suspended in 10 ml of the culture medium (MEM+10%FCS) and the suspension was further centrifuged to remove the supernatant.

Then, the residue was suspended in 5 ml of the culture medium to control the viable cell number ($2 \times 10^6$ cells/ml by trypan blue-staining). Thus obtained controlled cell suspension was poured into a 24-well plate (0.5 ml/well) and the sample solution (0.5 ml) was added to each well (0.5 ml/well) and the plate was incubated (37° C., 5% CO$_2$) for 24 hours. After filtration (0.22 μm) of the supernatant of the culture medium, the filtrate was kept at −20° C. as a bioassay sample.

5) Quantitative Assay of Interferon α in the Supernatant of the Culture Medium

Immediately after L cells (Dainippon Pharm. Co.) cultured in monolayer culture were treated with trypsin, the cells were added to the culture medium and the cell suspension ($4 \times 10^5$ cell/ml) was prepared by pipetting. Each 100 μl of the cell suspension was poured into all wells of a 96-well plate (Sumitomo Bakelite Co.) and the plate was incubated (37° C., 5% CO$_2$) for about 6 hours.

Standard mouse interferon (prepared by Lee Bio Molec. Res Co.) which was diluted by serial dilution method with a dilution plate and the above bioassay sample were poured into an assay plate (each of 50 μl). On the other hand only the culture medium (50 μl) was added to the uninfected cell control group and to the virus infected cell control group, respectively.

After incubation for 18 hours, the culture medium in the assay plate was removed. A solution containing bovine vesicular stomatitis virus [after cloning virus ($3.7 \times 10^8$ PFU/ml) distributed by Domestic Animal Research Institute with BHK cell, the original solution was diluted 300 times] was poured into all of wells (100 μl/well) except the virus uninfected control group. On the other hand, only the culture medium (100 μl) was added to the virus uninfected control group.

After incubation for about 48 hours, the virus solution on the assay plate was removed by suction. A dye solution (neutral red) was poured into all wells (50 μl/well). After incubation for 45 minutes, the dye solution was removed by suction and the wells were washed with PBS(−) solution.

After removal of the PBS(−) solution, UV was irradiated for 10 hours to inactivate the virus. A mixture (100 μl) of 0.1M $NaH_2PO_4$ and 99.5% ethanol (1:1) was poured into each well and the plate was stirred by a mixer for about 5 minutes. After that, the absorption at 540 nm was measured with a plate reader.

6) Result of Measurement

The result was shown in Table 1. The compounds of the present invention have inducing activity for biosynthesis of interferon. The drug concentration in the Table means final concentration.

TABLE 1

INDUCING ACTIVITY FOR BIOSYNTHESIS OF INTERFERON

| | Inducing activity for biosynthesis of interferon (IU/ml) | |
|---|---|---|
| Example No. | (0.1 μM) | (1 μM) |
| 1 | 93 | 46 |
| 16 | 111 | 26 |
| 24 | 3 | 34 |
| 25 | 92 | 50 |
| 30 | 80 | 19 |
| 42 | 21 | 13 |
| 43 | 18 | 17 |
| 44 | 33 | 14 |
| 48 | 28 | 14 |
| 54 | 47 | 18 |
| 60 | 31 | 12 |
| 66 | 40 | 23 |
| 67 | 36 | 20 |
| 79 | 7 | 18 |
| 80 | 25 | 18 |
| 81 | 21 | 18 |
| 82 | 29 | 18 |
| 88 | 47 | 26 |

Example 93

Activity on Cytokine Production from Mouse Lymph Node Cells

Experimental Method

1) Animals

BALB/c female mice were purchased from Japan Charlse River (Yokohama) and female mice (8 weeks) were used.

2) Culture Medium

RPMI1640 medium "DAIGO" (Nippon Seiyaku (Tokyo)) supplemented with 10% heat-inactivated (56° C., 30 min.) Fetal Bovine Serum (characterized Code No. A-1115-L, HyClone Lab., Logan, Utah) and 50 mM 2-mercaptoethanol (Sigma, St. Louis, Mo., Code No. M-6250) were used for the assay.

3) Test Compounds

Each test compound dissolved in DMSO (Nacalai Tesque (Kyoto) code No. 11J) at a concentration of 100 mM was diluted to final concentration with the medium.

4) Sensitization and Preparation of Lymph Node Cells

KLM (0.2 mg) was subcutaneously administered to mouse foot with Freund's complete adjuvant (Difco Lab., Detroit, Mich., Code No. 3113-60-5). Ten days later popliteal lymph node was picked up and its cell suspension was prepared.

5) Production of Cytokine by Stimulation with an Antigen

KLH (0.1 mg/ml) and the drug were added to lymph node cells ($5 \times 10^6$ cells/ml) and the mixture was incubated at 37° C. under 5% $CO_2$ for 4 days (Corning 25850, 0.15 ml/well). Then amount of cytokine produced in the supernatant was measured by ELISA specific to cytokine.

Amounts of interleukin 4 (IL-4) and interleukin 5 (IL-5) as a typical Th2 type cytokine, and interferon γ (IFN-γ) as a typical Th1 type cytokine were measured.

6) Method of Measurement (ELISA)

Amount of IL-4 was measured by ELISA as mentioned below. A rat anti-mouse IL-4 antibody (Pharmingen, San Diego, Calif., Code No. 18031D, 0.5 mg/ml) as a primary antibody was diluted 250 times with hydrogen carbonate buffer, and it was seeded to the 96-well plate (Falcon 3912, Becton Dickinson and Company, Franklin Lakes, N.J.) (50 ml/well) and each well was coated at 4° C. overnight. Then the plate was blocked with PBS (−) solution containing 3% BSA (200 ml/well). After rinsing and drying the plate, the plate was stored at −20° C. until beginning to use. The supernatant of the culture medium was added to the wells (50 ml/well) and the plate was incubated at room temperature for 4 hours. Recombinant mouse IL-4 (Pharmingen, Code No. 19231W) was used for preparing a calibration curve.

After rinsing the plate, a rat anti-mouse IL-4 antibody labeled by biotin (Pharmingen, Code No. 18042D, 0.5 mg/ml) as a secondary antibody, which was diluted 500 times with PBS (−) solution containing 0.1% BSA, was poured into wells (100 ml/well). The plate was incubated at room temperature. The secondary antibody bound to the plate was detected with streptoabidin alkaliphosphatase (Kirkegaad & Perry Lab., Gaithersburg, Md., Code No. 15-30-00)(0.25 mg/ml, 10 ml/well). After incubation at 37° C. for 1 hour and rinsing of the plate, the coloring was done by adding p-nitrophenyl disodium phosphate substrate (Nacalai Tesque)(1 mg/ml, 100 ml/well). The absorption at 415 nm was measured by a microplate reader (MTP-120 Microplatereader, Corona Electric Co.)

Measurement of amounts of IFN-γ was carried out in the same method as mentioned above by using a rat anti-mouse IFN-γ antibody (Pharmingen, San Diego, Calif., Code No. 18181D, 0.5 mg/ml) as a primary antibody and a rat anti-mouse IFN-γ antibody labeled by biotin (Pharmingen, Code No. 18112D, 0.5 mg/ml) as a secondary antibody. Recombinant mouse IFN-γ (Pharmingen, Code No. 19301U) was used for preparing a calibration curve.

Measurement of amounts of IL-5 was carried out in the same method as mentioned above by using a rat anti-mouse, IL-5 antibody (Pharmingen, San Diego, Calif., Code No. 18051D, 0.5 mg/ml) as a primary antibody and a rat anti-mouse IL-5 antibody labeled by biotin (Pharmingen, Code No. 18062D, 0.5 mg/ml) as a secondary antibody. Recombinant mouse IL-5 (Pharmingen, Code No. 19241W) was used for preparing a calibration curve. The test was carried out three times and their average was calculated.

The test result on IL-4 was shown in the following Table 2.

TABLE 2

Activity on inhibition for production of IL-4

| Example No. | Residual amount of IL-4 | | Inhibition |
|---|---|---|---|
| (Concentration of Drug 10 μM) | (ng/nl) | (residual rate %) | activity (%) |
| 1 | 2.67 | 31.1 | 68.9 |
| 2 | 3.81 | 41.3 | 58.7 |
| 3 | 1.63 | 11.7 | 88.3 |
| 4 | 3.81 | 39.1 | 60.9 |
| 5 | 5.98 | 69.1 | 30.9 |
| 7 | 5.24 | 53.8 | 46.2 |
| 8 | 4.98 | 53.9 | 46.1 |

TABLE 2-continued

Activity on inhibition for production of IL-4

| Example No. (Concentration of Drug 10 μM) | Residual amount of IL-4 (ng/nl) | (residual rate %) | Inhibition activity (%) |
|---|---|---|---|
| 11 | 5.84 | 68.1 | 21.9 |
| 12 | 3.89 | 45.4 | 54.6 |
| 15 | 3.44 | 40.1 | 59.9 |
| 16 | 4.75 | 51.4 | 48.6 |
| 17 | 5.25 | 56.9 | 43.1 |
| 18 | 6.47 | 70.1 | 29.9 |
| 19 | 1.73 | 12.7 | 87.3 |
| 20 | 3.38 | 32.1 | 67.9 |
| 21 | 3.86 | 28.4 | 71.6 |
| 22 | 2.22 | 16.3 | 83.7 |
| 23 | 2.56 | 18.8 | 81.2 |
| 26 | 6.64 | 68.0 | 32.0 |
| 32 | 6.78 | 25.4 | 74.6 |
| 36 | 5.22 | 49.6 | 50.4 |
| 42 | 2.12 | 7.9 | 92.1 |
| 48 | 1.89 | 7.7 | 96.3 |
| 81 | 1.50 | 6.1 | 93.9 |
| 88 | 2.84 | 10.7 | 89.3 |
| 89 | 3.00 | 28.5 | 71.5 |

Example 94

Activity of the Compound on Mouse Contact Hypersensitivity Reaction Induced by TNCB Test Method 1) Animals BALB/c female mice (6 weeks old) were purchased from Nippon Charles River Co. (Kanagawa) and they were used after previously feeding for 7 days.

2) Sensitization and Induction Method

Hair on mouse abdomen was cut and thereon was spread 7% 2,4,6-trinitrochlorobenzen (TNCB) (Tokyo Kasei (Tokyo)) in acetone (0.1 ml/mouse) to sensitize (day 0). 6 Days later 1% TNCB in acetone (10 ml) was spread on both sides of left auricula for induction.

3) Administration Method

After dissolving or homogeneously suspending in acetone, a test compound (10 ml) was spread on both sides of left auricula, respectively. The compound was applied once one hour before induction. As a positive control an adrenocortical hormone (Betamethasone, Wako Chemical Co. (Osaka)) was used.

4) Method of Measurement of Thickness of Auricula

Right before and 24 hours after spreading hapten (TNCB), thickness of left and right auriculae of each mouse was measured under diethyl ether anesthesia by dial thickness gauge (Mitutoyo, Tokyo).

Value of thickness of auricula was calculated by following equation: (Value of thickness of auricula)=(thickness of spread left auricula)−(thickness of unspread right auricula).

Inhibition rate of thickness was calculated by following equation:

Inhibition rate of thickness={1-[(value of thickness of auricula for 24 hours after drug application in drug-applied group)−(value of thickness of auricula before drug application in drug-applied group)]/[(value of thickness of auricula 24 hours after acetone application in acetone-applied group)−(value of thickness of auricula before drug application in acetone-applied group)]×100.

Result

The result was shown in Table 3.

It was observed that inhibition of thickness of auricula skin 24 hours after induction in the group of application of the drug was superior in comparing with the group of application of acetone substrate.

Mouse contact hypersensitivity reaction induced by TNCB is considered as a typical model for human contact dermatitis Therefore, the result shows that the compounds of the present invention have therapeutic and prophylactic activity for human contact dermatitis.

TABLE 3

| Example No. | Dose of drug | Inhibition rate (%) | Standard error (%) |
|---|---|---|---|
| 1 | 0.4 mg/ear | 79.0 | 3.7 |
| 20 | 0.4 mg/ear | 74.7 | 8.1 |
| 30 | 0.4 mg/ear | 37.3 | 8.6 |
| 32 | 0.4 mg/ear | 45.1 | 16.2 |
| 42 | 0.4 mg/ear | 59.7 | 7.5 |
| 44 | 0.4 mg/ear | 71.2 | 2.4 |
| 54 | 0.4 mg/ear | 63.1 | 1.6 |
| 58 | 0.4 mg/ear | 64.4 | 10.4 |
| 60 | 0.4 mg/ear | 85.0 | 7.6 |
| 81 | 0.4 mg/ear | 79.0 | 5.2 |
| 88 | 0.4 mg/ear | 39.1 | 10.4 |
| 90 | 0.4 mg/ear | 80.3 | 3.2 |
| Betamethasone | 0.001 mg/ear | 91.0 | 2.2 |
| Acetone substrate | | 0.0 | 9.8 |

Example 95

Activity of the Compound on Mouse Contact Hypersensitivity Reaction Induced by TNCB Test Method The test on compound of Example 79 was carried out in the same method as in Example 94.

Result

The result was shown in Table 4.

It was observed that inhibition of thickness of auricula skin 24 hours after induction in the group of application of compound of Example 79 was superior in comparing with the group of application of acetone substrate.

Mouse contact hypersensitivity reaction induced by the TNCB is considered as a typical model for human contact dermatitis Therefore, the result shows that compound of Example 79 has therapeutic and prophylactic activity for human contact dermatitis.

TABLE 4

| Example No. | Dose of drug | Inhibition rate (%) | Standard error (%) |
|---|---|---|---|
| 79 | 0.4 mg/ear | 68.9 | 2.3 |
| Betamethasone | 0.001 mg/ear | 64.4 | 5.3 |
| Acetone substrate | | 0.0 | 4.5 |

Example 96

Activity Against Ear Edema Reaction Induced by Arachidonic Acid

Test Method

1) Animal

1) Animals

BALB/c female mice (6 weeks) was purchased from Nippon Charles River Co. (Kanagawa) and they were used after previously feeding until 7 weeks old.

2) Administration Method

After weighing compound of Example 44 it was suspended in acetone (Kanto Kagaku Co.) (20 mg/ml). The suspension (10 µl) was spread on both sides of left auricula of mouse under anesthesia with diethyl ether, respectively. As a control acetone (10 µl) was spread on both sides of left auricula of another mouse, respectively.

2) Spread of Arachidonic Acid

Two hours after spread of compound of Example 44 or acetone, 10% arachidonic acid (CAYMAN CHEMICAL, Michigan) (10 µl) was spread on both sides of left auricula, respectively.

3) Measurement of Interdermal Reaction

One hour after spreading 10% arachidonic acid, thickness of both left and right auriculae was measured under anesthesia with diethyl ether by Dial thickness gauge (Mitutoyo, Tokyo).

Value of thickness of the auricula was calculated by following equation:

(Value of thickness of auricula)=(thickness of spread left auricula)−(thickness of unspread right auricula).

Inhibition rate of the thickness was calculated by following equation:

Inhibition rate of thickness={1−[(value of thickness of auricula 1 hour after drug application in drug-applied group)−(value of thickness of auricula before drug application in drug-applied group)]/[(value of thickness of auricula 1 hour after acetone application in acetone-applied group)−(value of thickness of auricula 1 hour before acetone application in acetone-applied group)]×100.

Result

The result was shown in Table 5.

It was observed that inhibition of thickness of auricular skin 1 hour after induction in the group of application of compound of Example 44 was superior in comparing with the group of application of acetone substrate.

The result indicates that the compounds of the present invention inhibit dermal inflammatory induced by arachidonic acid.

It is suggested that inflammatory mediators, that is, arachidonic acid metabolites, such as prostaglandins, leucotrienes and hydroxyeicosatetraenoic acids participate in dermal inflammatory disease such as psoriasis, UV dermatitis, mastocytosis and dermal cancer.

It was suggested that the compounds of the present invention are useful as therapeutic agents for diseases related to arachidonic acid metabolites.

TABLE 5

| Example No. | Dose of drug | Inhibition rate (%) | Standard error (%) |
|---|---|---|---|
| 44 | 0.4 mg/ear | 94.03 | 5.97 |
| Acetone substrate | | 0.0 | 25.37 |

Reference Example 1

6-Amino-2-chloropurine

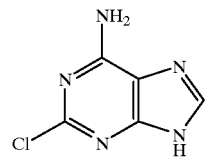

A solution of 2,6-dichloropurine 0.5 g (2.7 mmol) in 30% ammonia-methanol solution was heated at 100° C. in autoclave for 12 hours. The solution was condensed to give the subject compound. The compound may be used in next reaction without further purification.

$^1$H-NMR(DMSO-d$_6$) δ: 8.13(1H, s), 7.66(2H, br s).

Reference Example 2

6-Amino-9-benzyl-2-chloropurine

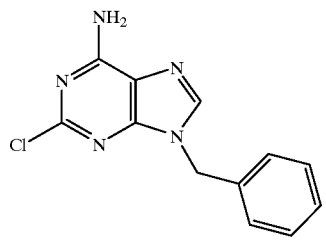

6-Amino-2-chloropurine (295 mg) and potassium carbonate (0.55 g, 4.0 mmol) were suspended in DMF (10 ml). Benzyl bromide (0.17 ml, 1.4 mmol) was added thereto and the mixture was stirred at room temperature for 4 hours. After condensing the suspension in vacuo, to the residue was added brine and the mixture was extracted with chloroform. The organic layer was washed the mixture was with brine, dried on magnesium sulfate, filtered and the solvent in the filtrate was evaporated in vacuo. The residue was purified with silica gel chromatography (5% methanol/chloroform) and recrystallized from ethanol to give the subject compound (200 mg, yield 58%). m.p. 216–218° C.

UVλ$_{max}$ (EtOH): 265.7 nm; $^1$H-NMR(DMSO-d$_6$) δ: 8.26 (1H, s), 7.81(2H, br s), 7.31(5H, m), 5.34(2H, s).

Reference Example 3

6-Amino-9-benzyl-2-methylthiopurine

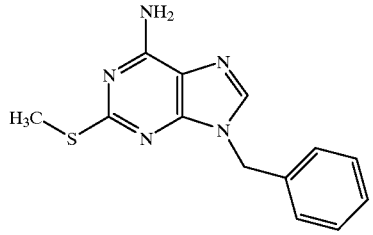

6-Amino-9-benzyl-2-chloropurine (100 mg, 0.39 mmol) and sodium methylthiolate (270 mg, 3.9 mmol) were mixed in DMF (10 ml) and then the mixture was stirred at 10° C. for 3.5 hours. To the reaction mixture was added brine and the mixture was extracted with ethyl acetate. The organic layer was dried on magnesium sulfate, filtered and the solvent in the filtrate was evaporated in vacuo. The residue was purified with silica gel chromatography (1% methanol/chloroform) to give the subject compound (64 mg, yield 61%).

$^1$H-NMR(CDCl$_3$) δ: 7.63(1H, s), 7.34(5H, m), 5.45(2H, br s), 5.31(2H, s), 2.58(3H, s).

Reference Example 4

6-Amino-9-benzyl-2-ethylthiopurine

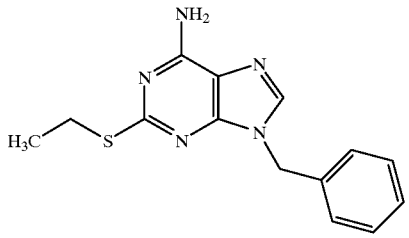

To DMF suspension (10 ml) containing sodium hydride (300 mg, 7.5 mmol, 60% in mineral oil) were added ethanethiol (2 ml, 27 mmol) and 6-amino-9-benzyl-2-chloropurine (100 mg, 0.39 mmol) in order. The mixture was stirred under heating at 110° C. for 3.5 hours. Brine was added thereto and the mixture was extracted with ethyl acetate. The organic layer was dried on magnesium sulfate, filtered and the solvent in the filtrate was evaporated. The residue was purified with silica gel chromatography (1% methanol/chloroform) to give the subject compound (90 mg, yield 82%).

$^1$H-NMR(CDCl$_3$) δ: 7.64(1H, s), 7.33(5H, m), 5.91(2H, br s), 5.29(2H, s), 3.17(2H, q, J=7.3 Hz), 1.39(3H, t, J=7.3 Hz).

Reference Example 5

6-Amino-9-benzyl-2-propylthiopurine

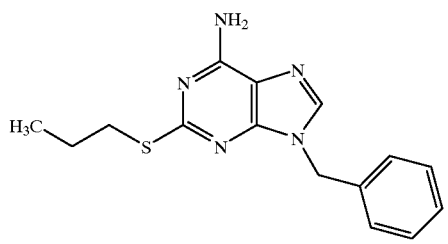

To DMF suspension (50 ml) containing sodium hydride (917 mg, 23 mmol, 60% in mineral oil) were added propanethiol (5.0 ml, 55 mmol) and 6-amino-9-benzyl-2-chloropurine (500 mg, 1.9 mmol) in order. The mixture was stirred under heating at 110° C. for 2.5 hours. Brine was added thereto and the mixture was extracted with ethyl acetate. The organic layer was dried on magnesium sulfate, filtered and the solvent in the filtrate was evaporated. The residue was purified with silica gel chromatography (1% methanol/chloroform) to give the subject compound (505 mg, yield 87%).

$^1$H-NMR(CDCl$_3$) δ: 7.64(1H, s), 7.32(5H, m), 6.09(2H, br s), 5.28(2H, s), 3.14(2H, t, J=7.3 Hz), 1.76(2H, m), 1.03(3H, t, J=7.3 Hz).

Reference Example 6

6-Amino-9-benzyl-2-(isopropylthio)purine

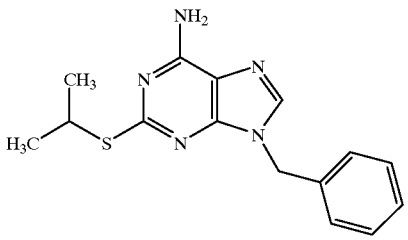

To DMF suspension (10 ml) containing sodium hydride (300 mg, 7.5 mmol 60% in mineral oil) were added 2-propanethiol (1.0 ml, 11 mmol) and 6-amino-9-benzyl-2-chloropurine (160 mg, 0.62 mmol) in order. The mixture was stirred under heating at 100° C. for 2.5 hours. Brine was added thereto and the mixture was extracted with chloroform. The organic layer was dried on magnesium sulfate, filtered and the solvent in the filtrate was evaporated in vacuo. The residue was purified with silica gel chromatography (1% methanol/chloroform) to give the subject compound (112 mg, yield 61%).

$^1$H-NMR(CDCl$_3$) δ: 7.64(1H, s), 7.32(5H, m), 5.49(2H, br s), 5.29(2H, s), 3.98(1H, m), 1.43(6H, d, J=6.6 Hz).

Reference Example 7

6-Amino-9-benzyl-2-butylthiopurine

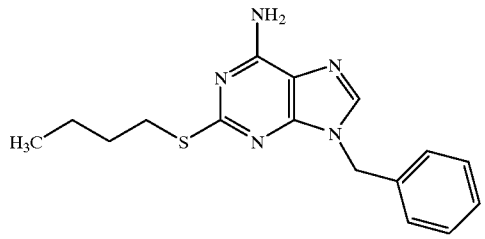

6-Amino-9-benzyl-2-chloropurine (310 mg, 1.2 mmol) and sodium butylthiolate (670 mg, 6.0 mmol) were mixed in DMF (30 ml) and then the mixture was stirred under heating at 100° C. for 4.5 hours. To the reaction mixture was added brine and the mixture was extracted with ethyl acetate. The organic layer was dried on magnesium sulfate, filtered and the solvent in the filtrate was evaporated in vacuo. The residue was purified with silica gel chromatography (0.5% methanol/chloroform) to give the subject compound (194 mg, yield 52%).

$^1$H-NMR(CDCl$_3$) δ: 7.63(1H, s), 7.35(5H, m), 5.54(2H, br s), 5.29(2H, s), 3.17(2H, t, J=7.3 Hz), 1.72(2H, m), 1.48(2H, m), 0.93(3H, t, J=7.6 Hz).

Reference Example 8

6-Amino-9-benzyl-2-(isobutylthio)purine

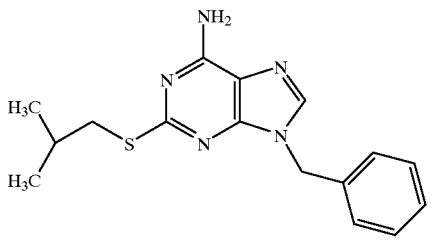

To DMF suspension (10 ml) containing sodium hydride (300 mg, 7.5 mmol, 60% in mineral oil) were added 2-methylpropane-1-thiol (1 ml, 11 mmol) and 6-amino-9-benzyl-2-chloropurine (200 mg, 0.77 mmol) in order. The mixture was stirred under heating at 100° C. for 5 hours. Brine was added thereto and the mixture was extracted with chloroform. The organic layer was dried on magnesium sulfate, filtered and the solvent in the filtrate was evaporated in vacuo. The residue was purified with silica gel chromatography (1% methanol/chloroform) to give the subject compound (76 mg, yield 31%).

$^1$H-NMR(CDCl$_3$) δ: 7.63(1H, s), 7.32(5H, m), 5.46(2H, br s), 5.29(2H, s), 3.08(d, 2H, J=6.9 Hz), 2.00(1H, m), 1.04(6H, d, J=6.6 Hz).

Reference Example 9

6-Amino-9-benzyl-2-(sec-butylthio)purine

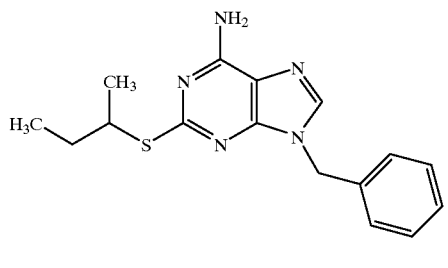

To DMF suspension (10 ml) containing sodium hydrate (300 mg, 7.5 mmol, 60% in mineral oil) were added 2-butanethiol (1 ml, 11 mmol) and 6-amino-9-benzyl-2-chloropurine (200 mg, 0.77 mmol) in order. The mixture was stirred under heating at 100° C. for 5 hours. Brine was added thereto and the mixture was extracted with chloroform. The organic layer was dried on magnesium sulfate, filtered and the solvent in the filtrate was evaporated in vacuo. The residue was purified with silica gel chromatography (1% methanol/chloroform) to give the subject compound (85 mg, yield 35%).

$^1$H-NMR(CDCl$_3$) δ: 7.63(1H, s), 7.32(5H, m), 5.46(2H, br s), 5.29(2H, s), 3.85(1H, m), 1.75(2H, m), 1.42(3H, d, J=6.9 Hz), 1.03(3H, t, J=7.6 Hz).

Reference Example 10

6-Amino-9-benzyl-2-pentylthiopurine

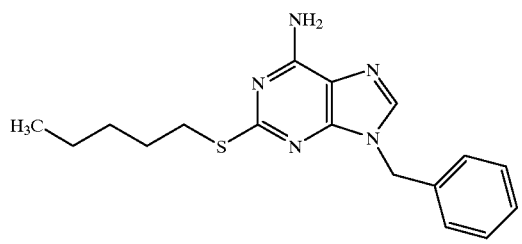

To DMF suspension (10 ml) containing sodium hydride (277 mg, 6.9 mmol, 60% in mineral oil) were added 1-pentanethiol (2 ml, 16 mmol) and 6-amino-9-benzyl-2-chloropurine (100 mg, 0.39 mmol) in order. The mixture was stirred under heating at 110° C. for 4 hours. Brine was added thereto and the mixture was extracted with ethyl acetate. The organic layer was dried on magnesium sulfate, filtered and the solvent in the filtrate was evaporated in vacuo. The residue was purified with silica gel chromatography (1% methanol/chloroform) to give the subject compound (102 mg, yield 81%).

$^1$H-NMR(CDCl$_3$) δ: 7.64(1H, s), 7.33(5H, m), 5.77(2H, br s), 5.29(2H, s), 3.16(2H, t, J=7.3 Hz), 1.75(2H, m), 1.33–1.46(4H, m), 0.89(3H, t, J=7.3 Hz).

Reference Example 11

6-Amino-9-benzyl-2-(3-methylbutyl)thiopurine

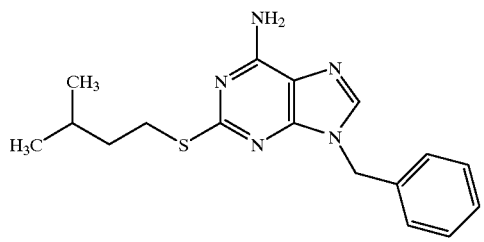

To DMF suspension (10 ml) containing sodium hydride (300 mg, 7.5 mmol, 60% in mineral oil) were added 3-methylbutane-1-thiol (1 ml, 8.0 mmol) and 6-amino-9-benzyl-2-chloropurine (200 mg, 0.77 mmol) in order. The mixture was stirred under heating at 100° C. for 2.5 hours. Brine was added thereto and the mixture was extracted with chloroform. The organic layer was dried on magnesium sulfate, filtered and the solvent in the filtrate was evaporated in vacuo. The residue was purified with silica gel chromatography (1% methanol/chloroform) to give the subject compound (120 mg, yield 48%).

$^1$H-NMR(CDCl$_3$) δ: 7.63(1H, s), 7.32(5H, m), 5.44(2H, br s), 5.29(2H, s), 3.17(2H, t, J=7.9 Hz), 1.64(3H, m), 0.94(6H, d, J=6.6 Hz).

Reference Example 12

6-Amino-9-benzyl-2-(2-methylbutyl)thiopurine

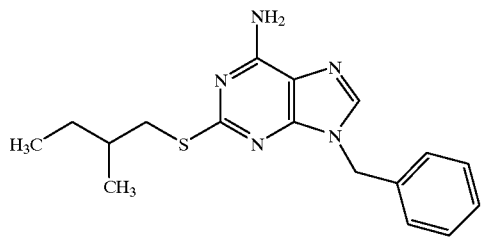

To DMF suspension (10 ml) containing sodium hydride (300 mg, 7.5 mmol, 60% in mineral oil) were added 2-methylbutane-1-thiol (1 ml, 8.0 mmol) and 6-amino-9-benzyl-2-chloropurine (200 mg, 0.77 mmol) in order. The mixture was stirred under heating at 100° C. for 4.5 hours. Brine was added thereto and the mixture was extracted with chloroform. The organic layer was dried on magnesium sulfate, filtered and the solvent in the filtrate was evaporated in vacuo. The residue was purified with silica gel chromatography (1% methanol/chloroform) to give the subject compound (80 mg, yield 32%).

$^1$H-NMR(CDCl$_3$) δ: 7.63(1H, s), 7.32(5H, m), 5.50(2H, br s), 5.30(2H, s), 3.26(1H, q, J=5.9 Hz), 2.99(1H, q, J=7.6 Hz), 1.78(1H, m), 1.55(1H, m), 1.28(1H, m), 1.02(3H, d, J=11.9 Hz), 0.92(3H, t, J=11.8 Hz).

Reference Example 13

6-Amino-9-benzyl-2-cyclohexylthiopurine

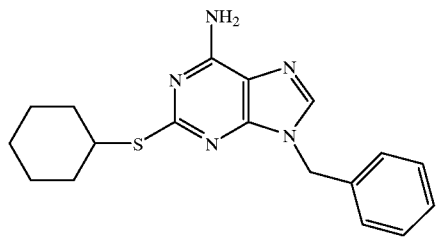

To DMF suspension (10 ml) containing sodium hydride (256 mg, 6.4 mmol, 60% in mineral oil) were added cyclohexanethiol (2 ml, 16 mmol) and 6-amino-9-benzyl-2-chloropurine (100 mg, 0.39 mmol) in order. The mixture was heated at 100° C. for 3.5 hours. Brine was added thereto and the mixture was extracted with ethyl acetate. The organic layer was dried on magnesium sulfate, filtrated and the solvent in the filtrate was evaporated in vacuo. The residue was purified with silica gel chromatography (1% methanol/chloroform) to give the subject compound (112 mg, yield 86%).

$^1$H-NMR(CDCl$_3$) δ: 7.65(1H, s), 7.33(5H, m), 5.86(2H, br s), 5.28(2H, m), 3.75–3.87(1H, m), 2.11–2.17(2H, m), 1.25–1.67(8H, m).

Reference Example 14

6-Amino-9-benzyl-2-phenylthiopurine

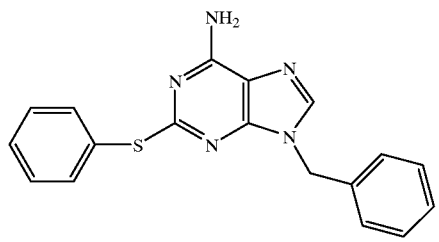

6-Amino-9-benzyl-2-chloropurine (200 mg, 0.77 mmol) and sodium thiophenolate (2 g, 15 mmol) were mixed in DMF (12 ml) and then the mixture was stirred under heating at 100° C. for 7.5 hours. To the reaction mixture was added brine and the mixture was extracted with ethyl acetate. The organic layer was dried on magnesium sulfate, filtered and the solvent in the filtrate was evaporated in vacuo. The residue was purified with silica gel chromatography (0.5% methanol/chloroform) to give the subject compound (228 mg, yield 89%).

$^1$H-NMR(CDCl$_3$) δ: 7.65–7.70(3H, m), 7.41–7.45(3H, m), 7.28–7.33(3H, m), 7.15–7.20(2H, m), 5.54(2H, br s), 5.09(2H, s).

Reference Example 15

6-Amino-9-benzyl-2-(p-tolylthio)purine

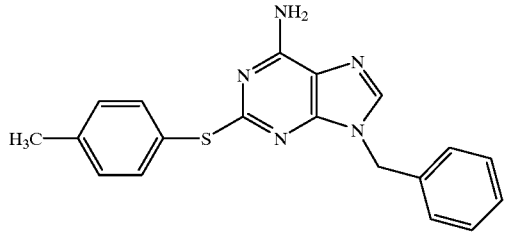

To DMF suspension (10 ml) containing sodium hydride (300 mg, 7.5 mmol, 60% in mineral oil) were added p-toluenethiol (1.9 g, 15 mmol) and 6-amino-9-benzyl-2-chloropurine (100 mg, 0.39 mmol) in order. The mixture was stirred under heating at 100° C. for 3 hours. Brine was added thereto and the mixture was extracted with chloroform. The organic layer was dried on magnesium sulfate, filtrated and the solvent in the filtrate was evaporated in vacuo. The residue was purified with silica gel chromatography (1% methanol/chloroform) to give the subject compound (124 mg, yield 93%).

$^1$H-NMR(CDCl$_3$) δ: 7.62(1H, s), 7.55(2H, d, J=8.2 Hz), 7.15–7.31(7H, m), 5.61(2H, br s), 5.10(2H, s), 2.40(3H, s).

Reference Example 16

6-Amino-9-benzyl-2-(2-naphthylthio)purine

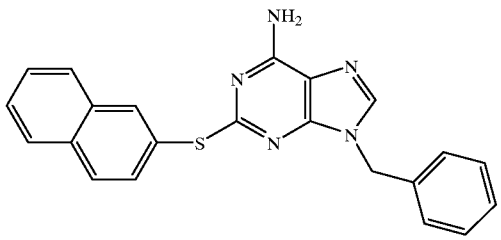

To DMF suspension (20 ml) containing sodium hydride (800 mg, 20 mmol, 60% in mineral oil) were added 2-naphthalenethiol (3.8 g, 24 mmol) and 6-amino-9-benzyl-2-chloropurine (200 mg, 0.77 mmol) in order. The mixture was stirred under heating at 100° C. for 10.5 hours. Brine was added thereto and the mixture was extracted with chloroform. The organic layer was dried on magnesium sulfate, filtrated and the solvent in the filtrate was evaporated in vacuo. The residue was purified with silica gel chromatography (0.5% methanol/chloroform) to give the subject compound (244 mg, yield 83%).

$^1$H-NMR(CDCl$_3$) δ: 8.17(1H, s), 7.52–7.92(7H, m), 7.06–7.30(5H, m), 5.63(2H, br s), 5.04(2H, s).

Reference Example 17

6-Amino-9-benzyl-2-benzylthiopurine

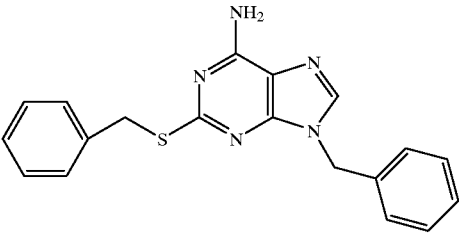

To DMF suspension (10 ml) containing sodium hydride (410 mg, 10 mmol, 60% in mineral oil) were added α-toluenethiol (1.7 ml, 14 mmol) and 6-amino-9-benzyl-2-chloropurine (100 mg, 0.39 mmol) in order. The mixture was stirred under heating at 100° C. for 4.5 hours. Brine was added thereto and the mixture was extracted with ethyl acetate. The organic layer was dried on magnesium sulfate, filtrated and the solvent in the filtrate was evaporated in vacuo. The residue was purified with silica gel chromatography (0.5% methanol/chloroform) to give the subject compound (97 mg, yield 73%).

$^1$H-NMR(CDCl$_3$) δ: 7.64(1H, s), 7.22–7.45(10H, m), 5.48(2H, br s), 5.31(2H, s), 4.43(2H, s).

Reference Example 18

6-Amino-9-benzyl-8-bromo-2-methylthiopurine

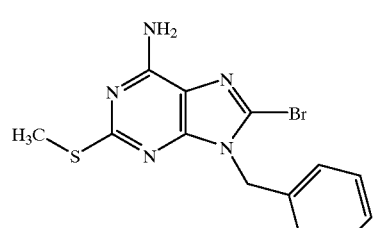

6-Amino-9-benzyl-2-methylthiopurine (100 mg, 0.37 mmol) and bromine (0.5 ml) were dissolved in 100 ml of methylene chloride and the solution was stirred at room temperature for 3 hours. Aqueous sodium thiosulfate was added to the reaction mixture. The organic layer was separated, dried on magnesium sulfate and filtered. The solvent in the filtrate was evaporated in vacuo. The residue was purified with silica gel chromatography (0.5% methanol/chloroform) to give the subject compound (10 mg, yield 8%).

$^1$H-NMR(CDCl$_3$) δ: 7.34(5H, m), 5.64(2H, br s), 5.33(2H, s), 2.57(3H, s).

Reference Example 19

6-Amino-9-benzyl-8-bromo-2-ethylthiopurine

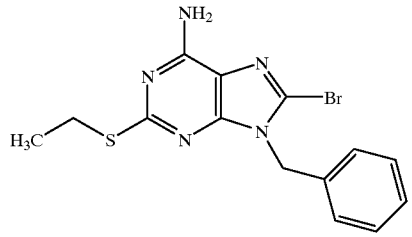

6-Amino-9-benzyl-2-ethylthiopurine (214 mg, 0.75 mmol) and bromine (0.5 ml) were dissolved in 100 ml of methylene chloride and the solution was stirred at room temperature for 7 hours. Aqueous sodium thiosulfate was added to the reaction mixture. The organic layer was separated, dried on magnesium sulfate and filtered. The solvent in the filtrate was evaporated in vacuo. The residue was purified with silica gel chromatography (1% methanol/chloroform) to give the subject compound (43 mg, yield 16%).

$^1$H-NMR(CDCl$_3$) δ: 7.32(5H, m), 5.82(2H, br s), 5.32 (2H, s), 3.16(2H, q, J=7.3 Hz), 1.39(3H, t, J=7.3 Hz).

Reference Example 20

6-Amino-9-benzyl-8-bromo-2-propylthiopurine

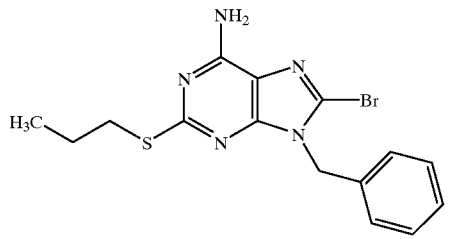

6-Amino-9-benzyl-2-propylthiopurine (290 mg, 0.97 mmol) and bromine (0.7 ml) were dissolved in 160 ml of methylene chloride and the solution was stirred at room temperature for 4.5 hours. Aqueous sodium thiosulfate was added to the reaction mixture. The organic layer was separated, dried on magnesium sulfate and filtered. The solvent in the filtrate was evaporated in vacuo. The residue was purified with silica gel chromatography (1% methanol/chloroform) to give the subject compound (58 mg, yield 16%).

$^1$H-NMR(CDCl$_3$) δ: 7.35(5H, m), 5.70(2H, br s), 5.32 (2H, s), 3.13(2H, t, J=7.6 Hz), 1.76(2H, m), 1.04(3H, t, J=7.6 Hz).

Reference Example 21

6-Amino-9-benzyl-8-bromo-2-(isopropylthio)purine

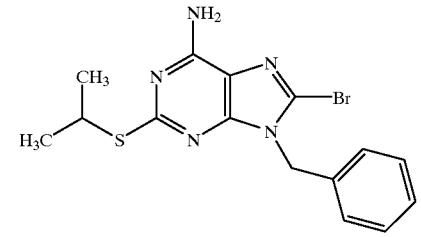

6-Amino-9-benzyl-2-(isopropylthio)purine (60 mg, 0.20 mmol) and bromine (0.4 ml) were dissolved in 85 ml of methylene chloride and the solution was stirred at room temperature for 2 hours. Aqueous sodium thiosulfate was added to the reaction mixture. The organic layer was separated, dried on magnesium sulfate and filtered. The solvent in the filtrate was evaporated in vacuo. The residue was purified with silica gel chromatography (1% methanol/chloroform) to give the subject compound (20 mg, yield 26%).

$^1$H-NMR(CDCl$_3$) δ: 7.34(5H, m), 5.72(2H, br s), 5.32 (2H, s), 3.96(1H, m), 1.42(6H, d, J=7.0 Hz).

Reference Example 22

6-Amino-9-benzyl-8-bromo-2-butylthiopurine

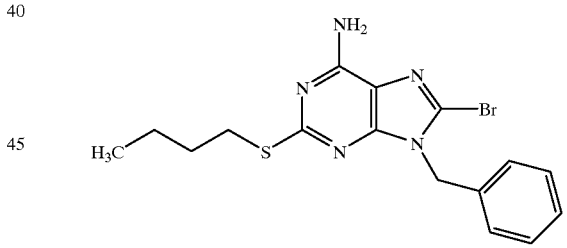

6-Amino-9-benzyl-2-butylthiopurine (163 mg, 0.52 mmol) and bromine (0.6 ml) were dissolved in 180 ml of methylene chloride and the solution was stirred at room temperature for 4.5 hours. Aqueous sodium thiosulfate was added to the reaction mixture. The organic layer was separated, dried on magnesium sulfate and filtered. The solvent in the filtrate was evaporated in vacuo. The residue was purified with silica gel chromatography (1% methanol/chloroform) to give the subject compound (35 mg, yield 17%).

$^1$H-NMR(CDCl$_3$) δ: 7.34(5H, m), 5.81(2H, br s), 5.32 (2H, s), 3.15(2H, t, J=7.3 Hz), 1.72(2H, m), 1.45(2H, m), 0.92(3H, t, J=7.6 Hz).

Reference Example 23

6-Amino-9-benzyl-8-bromo-2-(isobutylthio)purine

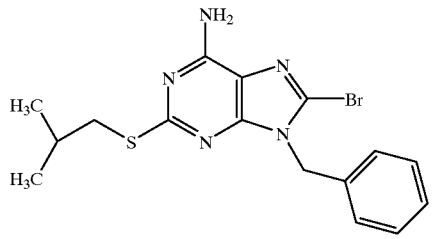

6-Amino-9-benzyl-2-(isobutylthio)purine (60 mg, 0.19 mmol) and bromine (0.4 ml) were dissolved in 85 ml of methylene chloride and the solution was stirred at room temperature for 2 hours. Aqueous sodium thiosulfate was added to the reaction mixture. The organic layer was separated, dried on magnesium sulfate and filtered. The solvent in the filtrate was evaporated in vacuo. The residue was purified with silica gel chromatography (chloroform) to give the subject compound (20 mg, yield 27%).

$^1$H-NMR(CDCl$_3$) δ: 7.34(5H, m), 5.59(2H, br s), 5.32 (2H, s), 3.07(2H, t, J=6.6 Hz), 1.96(1H, m), 1.04(6H, d, J=6.6 Hz).

Reference Example 24

6-Amino-9-benzyl-8-bromo-2-(sec-butylthio)purine

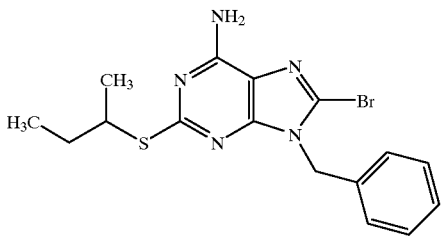

6-Amino-9-benzyl-2-(sec-butylthio)purine (60 mg, 0.19 inmol) and bromine (0.4 ml) were dissolved in 85 ml of methylene chloride and the solution was stirred at room temperature for 2 hours. Aqueous sodium thiosulfate was added to the reaction mixture. The organic layer was separated, dried on magnesium sulfate and filtered. The solvent in the filtrate was evaporated in vacuo. The residue was purified with silica gel chromatography (chloroform) to give the subject compound (53 mg, yield 71%).

$^1$H-NMR(CDCl$_3$) δ: 7.34(5H, m), 5.45(2H, br s), 5.32 (2H, s), 3.83(1H, m), 1.63(2H, m), 1.42(3H, d, J=7.0 Hz), 1.03(3H, t, J=7.3 Hz).

Reference Example 25

6-Amino-9-benzyl-8-bromo-2-pentylthiopurine

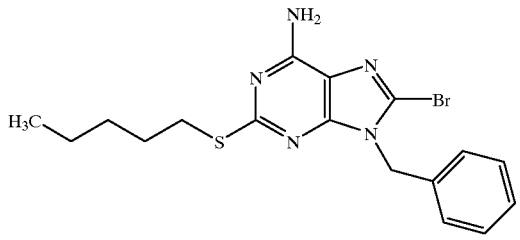

6-Amino-9-benzyl-2-pentylthiopurine (260 mg, 0.79 mmol) and bromine (0.5 ml) were dissolved in 100 ml of methylene chloride and the solution was stirred at room temperature for 7 hours. Aqueous sodium thiosulfate was added to the reaction mixture. The organic layer was separated, dried on magnesium sulfate and filtered. The solvent of the filtrate was evaporated in vacuo. The residue was purified with silica gel chromatography (1% methanol/chloroform) to give the subject compound (49 mg, yield 15%).

$^1$H-NMR(CDCl$_3$) δ: 7.33(5H, m), 5.95(2H, br s), 5.31 (2H, s), 3.14(2H, t, J=7.3 Hz), 1.74(2H, m), 1.27–1.47(4H, m), 0.88(3H, t, J=7.3 Hz).

Reference Example 26

6-Amino-9-benzyl-8-bromo-2-(3-methylbutyl)thiopurine

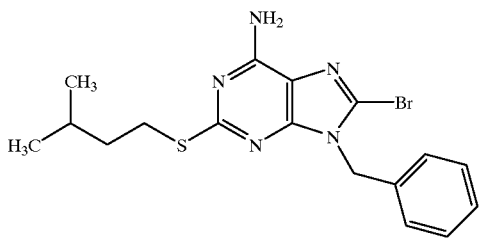

6-Amino-9-benzyl-2-(3-methylbutyl)thiopurine (260 mg, 0.79 mmol) and bromine (0.5 ml) were dissolved in 100 ml of methylene chloride and the solution was stirred at room temperature for 7 hours. Aqueous sodium thiosulfate was added to the reaction mixture. The organic layer was separated, dried on magnesium sulfate and filtered. The solvent in the filtrate was evaporated in vacuo. The residue was purified with silica gel chromatography (1% methanol/chloroform) to give the subject compound (49 mg, yield 15%).

$^1$H-NMR(CDCl$_3$) δ: 7.33(5H, m), 5.52(2H, br s), 5.30 (2H, s), 3.15(2H, t, J=7.9 Hz), 1.61–1.76(3H, m), 0.92(6H, t, J=6.2 Hz).

Reference Example 27

6-Amino-9-benzyl-8-bromo-2-(2-methylbutyl)thiopurine

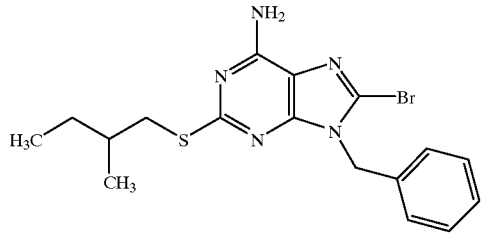

6-Amino-9-benzyl-2-(2-methylbutyl)thiopurine (60 mg, 0.18 mmol) and bromine (0.4 ml) were dissolved in 90 ml of methylene chloride and the solution was stirred at room temperature for 7 hours. Aqueous sodium thiosulfate was added to the reaction mixture. The organic layer was separated, dried on magnesium sulfate and filtered. The solvent in the filtrate was evaporated in vacuo. The residue was purified with silica gel chromatography (1% methanol/chloroform) to give the subject compound (39 mg, yield 53%).

$^1$H-NMR(CDCl$_3$) δ: 7.33(5H, m), 5.44(2H, br s), 5.32 (2H, s), 3.24(1H, q, J=7.9 Hz), 2.98(1H, q, J=7.3 Hz), 1.75(1H, m), 1.52(1H, m), 1.28(1H, m), 1.01(3H, d, J=6.6 Hz), 0.91(3H, t, J=7.3 Hz).

Reference Example 28

6-Amino-9-benzyl-8-bromo-2-cyclohaxylthiopurine

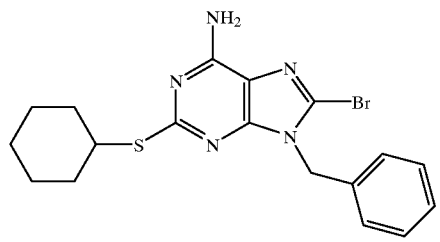

6-Amino-9-benzyl-2-cyclohexylthiopurine (178 mg, 0.52 mmol) and bromine (0.4 ml) were dissolved in 90 ml of methylene chloride and the solution was stirred at room temperature for 7 hours. Aqueous sodium thiosulfate was added to the reaction mixture. The organic layer was separated, dried on magnesium sulfate and filtered. The solvent in the filtrate was evaporated in vacuo. The residue was purified with silica gel chromatography (0.5% methanol/chloroform) to give the subject compound (86 mg, yield 40%).

$^1$H-NMR(CDCl$_3$) δ: 7.30–7.45(5H, m), 5.69(2H, br s), 5.31(2H, s), 3.80(1H, m), 2.10(2H, m), 1.25–1.78(8H, m).

Reference Example 29

6-Amino-9-benzyl-8-bromo-2-phenylthiopurine

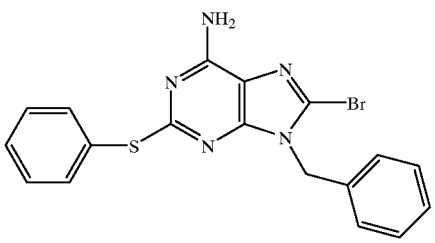

6-Amino-9-benzyl-2-phenylthiopurine (95 mg, 0.28 mmol) and bromine (0.4 ml) were dissolved in 150 ml of methylene chloride and the solution was stirred at room temperature for 4.5 hours. Aqueous sodium thiosulfate was added to the reaction mixture. The organic layer was separated, dried on magnesium sulfate and filtered. The solvent in the filtered was evaporated in vacuo. The residue was purified with silica gel chromatography (0.5% methanol/chloroform) to give the subject compound (25 mg, yield 22%).

$^1$H-NMR(CDCl$_3$) δ: 7.65–7.68(2H, m), 7.42–7.44(3H, m), 7.20–7.28(5H, m), 5.49(2H, br s), 5.09(2H, s).

Reference Example 30

6-Amino-9-benzyl-8-bromo-2-(p-tolylthio)purine

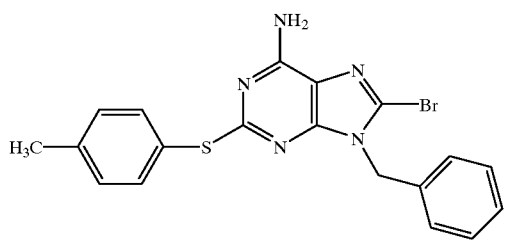

6-Amino-9-benzyl-2-(p-tolylthio)purine (86 mg, 0.37 mmol) and bromine (0.4 ml) were dissolved in 120 ml of methylene chloride and the solution was stirred at room temperature for 4 hours. Aqueous sodium thiosulfate was added to the reaction mixture. The organic layer was separated, dried on magnesium sulfate and filtered. The solvent in the filtrate was evaporated in vacuo. The residue was purified with silica gel chromatography (0.5% methanol/chloroform) to give the subject compound (20 mg, yield 19%).

$^1$H-NMR(CDCl$_3$) δ: 7.55(2H, d, J=7.9 Hz), 7.20–7.28 (7H, m), 5.40(2H, br s), 5.10(2H, s), 2.41(3H, s).

Reference Example 31

6-Amino-9-benzyl-8-bromo-2-(2-naphthylthio)purine

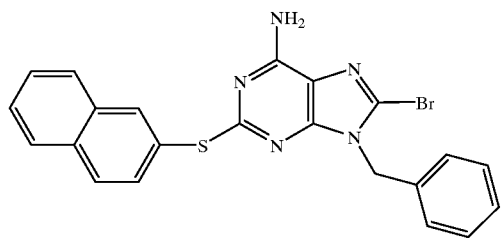

6-Amino-9-benzyl-2-(2-naphthylthio)purine (221 mg, 0.58 mmol) and bromine (0.4 ml) were dissolved in 160 ml of methylene chloride and the solution was stirred at room temperature for 5.5 hours. Aqueous sodium thiosulfate was added to the reaction mixture. The organic layer was separated, dried on magnesium sulfate and filtered. The solvent in the filtrate was evaporated in vacuo. The residue was purified with silica gel chromatography (0.5% methanol/chloroform) to give the subject compound (118 mg, yield 44%).

$^1$H-NMR(CDCl$_3$) δ: 8.42(1H, d, J=8.3 Hz), 7.80–7.87 (3H, m), 7.52–7.66(2H, m), 7.04–7.21(6H, m), 5.56(2H, br s), 5.00(2H, s).

Reference Example 32

6-Amino-9-benzyl-2-benzylthio-8-bromopurine

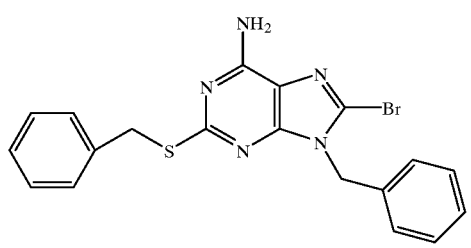

6-Amino-9-benzyl-2-benzylthiopurine (176 mg, 0.51 mmol) and bromine (1 ml) were dissolved in 160 ml of methylene chloride and the solution was stirred at room temperature for 4 hours. Aqueous sodium thiosulfate was added to the reaction mixture. The organic layer was separated, dried on magnesium sulfate and filtered. The solvent in the filtrate was evaporated in vacuo. The residue was purified with silica gel chromatography (0.5% methanol/chloroform) to give the subject compound (19 mg, yield 9%).

$^1$H-NMR(CDCl$_3$) δ: 7.21–7.39(10H, m), 5.50(2H, br s), 5.33(2H, s), 4.41(2H, m).

Reference Example 33

6-Amino-9-benzyl-2-methoxypurine

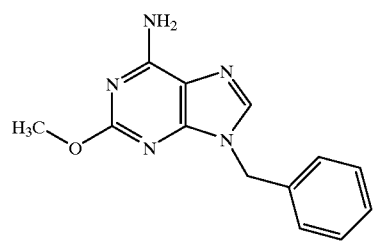

6-Amino-9-benzyl-2-chloropurine (200 mg, 0.77 mmol) and sodium methylate (208 mg, 3.85 mmol) were dissolved in methanol (20 ml) and then the solution was refluxed on heating under stirring for 30 hours. The reaction mixture was evaporated in vacuo to dryness. To the residue was added water and the mixture was extracted with chloroform. The organic layer was dried on sodium sulfate and evaporated in vacuo to dryness. The residue was purified with silica gel chromatography (2% methanol/chloroform) to give the subject compound (151 mg, yield 77%).

$^1$H-NMR(DMSO-d$_6$) δ: 8.05(1H, s), 7.37–7.25(7H, m), 5.26(2H, s), 3.81(3H, s).

Reference Example 34

6-Amino-9-benzyl-2-ethoxypurine

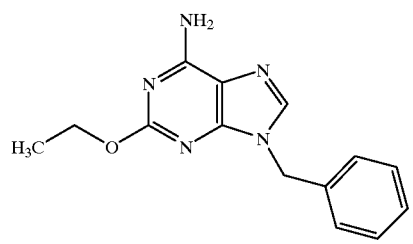

6-Amino-9-benzyl-2-chloropurine (200 mg, 0.77 mmol) and sodium ethylate (262 mg, 3.85 mmol) were dissolved in ethanol (20 ml) and then the solution was refluxed on heating under stirring for 20 hours. The reaction mixture was evaporated in vacuo to dryness. To the residue was added water and the mixture was extracted with chloroform. The organic layer was dried on sodium sulfate and evaporated in vacuo to dryness. The residue was purified with silica gel chromatography (2% methanol/chloroform) to give the subject compound (151 mg, yield 73%).

$^1$H-NMR(DMSO-d$_6$) δ: 8.04(1H, s), 7.37–7.21(7H, m), 5.25(2H, s), 4.25(2H, q, J=7.1 Hz), 1.27(3H, t, J=7.1 Hz).

Reference Example 35

6-Amino-9-benzyl-2-propoxypurine

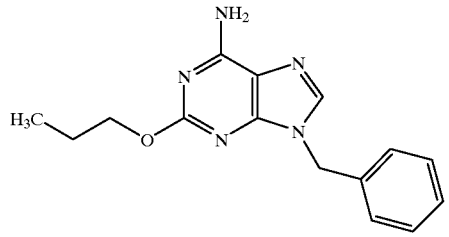

6-Amino-9-benzyl-2-chloropurine (200 mg, 0.77 mmol) and sodium propylate (316 mg, 3.85 mmol) were dissolved in 1-propanol (20 ml) and then the solution was refluxed on heating under stirring for 3 hours. The reaction mixture was evaporated in vacuo to dryness. To the residue was added water and the mixture was extracted with chloroform. The organic layer was dried on sodium sulfate and evaporated in vacuo to dryness. The residue was purified with silica gel chromatography (2% methanol/chloroform) to give the subject compound (162 mg, yield 74%).

$^1$H-NMR(DMSO-$d_6$) δ: 8.04(1H, s), 7.37–7.21(7H, m), 5.26(2H, s), 4.16(2H, t, J=6.6 Hz), 1.68(2H, m), 0.95(3H, t, J=7.3 Hz).

Reference Example 36

6-Amino-9-benzyl-2-butoxypurine

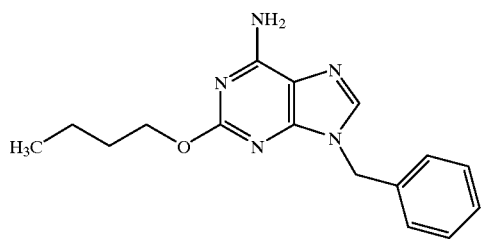

6-Amino-9-benzyl-2-chloropurine (200 mg, 0.77 mmol) and sodium butylate (370 mg, 3.85 mmol) were dissolved in 1-butanol (20 ml) and then the solution was refluxed on heating under stirring for 2 hours. The reaction mixture was evaporated in vacuo to dryness. To the residue was added water and the mixture was extracted with chloroform. The organic layer was dried on sodium sulfate and evaporated in vacuo to dryness. The residue was purified with silica gel chromatography (2% methanol/chloroform) to of give the subject compound (131 mg, yield 54%).

$^1$H-NMR(DMSO-$d_6$) δ: 8.03(1H, s), 7.37–7.21(7H, m), 5.25(2H, s), 4.20(2H, t, J=6.4 Hz), 1.65(2H, m), 1.39(2H, m), 0.92(3H, t, J=7.3 Hz).

Reference Example 37

6-Amino-9-benzyl-2-pentoxypurine

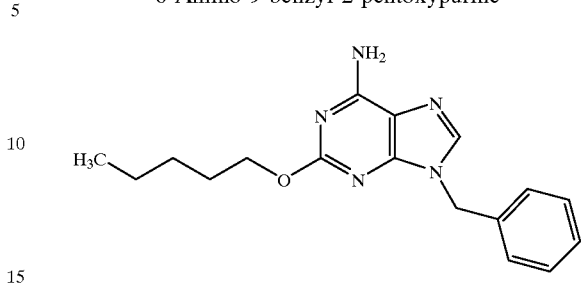

6-Amino-9-benzyl-2-chloropurine (150 mg, 0.58 mmol) and sodium pentylate (318 mg, 2.89 mmol) were dissolved in 1-pentanol (50 ml) and then the solution was stirred under heating at 130° C. for 5 hours. The reaction mixture was evaporated in vacuo to dryness. To the residue was added water and the mixture was extracted with chloroform. The organic layer was dried on sodium sulfate and evaporated in vacuo to dryness. The residue was purified with silica gel chromatography (2% methanol/chloroform) to give the subject compound (103 mg, yield 57%).

$^1$H-NMR(DMSO-$d_6$) δ: 8.03(1H, s), 7.37–7.25(5H, m), 7.20(2H, br s), 5.26(2H, s), 4.20(2H, t, J=6.6 Hz), 1.67(2H, m), 1.33(4H, m), 0.88(3H, t, J=6.6 Hz).

Reference Example 38

6-Amino-9-benzyl-8-bromo-2-methoxypurine

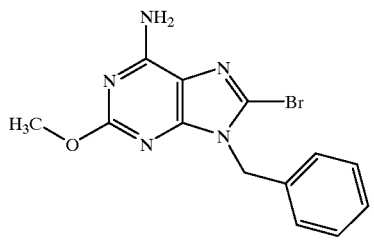

6-Amino-9-benzyl-2-methoxypurine (118 mg, 0.46 mmol) and bromine (0.5 ml) were dissolved in 50 ml of methylene chloride and the solution was stirred at room temperature for 5 hours. Aqueous sodium thiosulfate was added to the reaction mixture. The organic layer was separated, dried on sodium sulfate and evaporated in vacuo to dryness. The residue was purified with silica gel chromatography (1% methanol/chloroform) to give the subject compound (90 mg, yield 58%).

$^1$H-NMR(DMSO-$d_6$) δ: 7.48 (2H, br s), 7.39–7.24 (5H, m), 5.26 (2H, s), 3.82 (3H, s).

Reference Example 39

6-Amino-9-benzyl-8-bromo-2-ethoxypurine

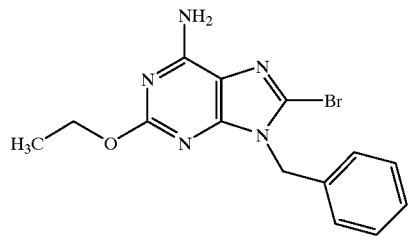

6-Amino-9-benzyl-2-ethoxypurine (143 mg, 0.53 mmol) and bromine (0.5 ml) were dissolved in 50 ml of methylene chloride and the solution was stirred at room temperature for 5 hours. Aqueous sodium thiosulfate was added to the reaction mixture. The organic layer was separated and dried on sodium sulfate, filtered and evaporated in vacuo to dryness. The residue was purified with silica gel chromatography (1% methanol/chloroform) to give the subject compound (42 mg, yield 23%).

$^1$H-NMR(DMSO-$d_6$) δ: 7.43(2H, br s), 7.38–7.24(5H, m), 5.25(2H, s), 4.26(2H, q, J=7.1 Hz), 1.28(3H, t, J=7.1 Hz).

Reference Example 40

6-Amino-9-benzyl-8-bromo-2-propoxypurine

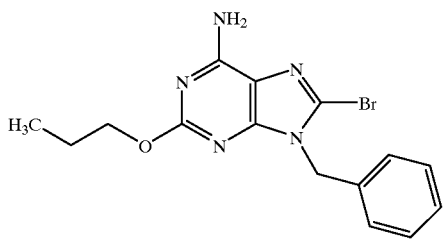

6-Amino-9-benzyl-2-ethoxypurine (134 mg, 0.473 mmol) and bromine (0.5 ml) were dissolved in 50 ml of methylene chloride and the solution was stirred at room temperature for 5 hours. Aqueous sodium thiosulfate was added to the reaction mixture. The organic layer was separated and dried on sodium sulfate and evaporated in vacuo to dryness. The residue was purified with silica gel chromatography (1% methanol/chloroform) to give the subject compound (55 mg, yield 32%).

$^1$H-NMR(DMSO-$d_6$) δ: 7.43(2H, br s), 7.38–7.23(5H, m), 5.25(2H, s), 4.16(2H, t, J=6.6 Hz), 1.70(2H, m), 0.94(3H, t, J=7.3 Hz).

Reference Example 41

6-Amino-9-benzyl-8-bromo-2-butoxypurine

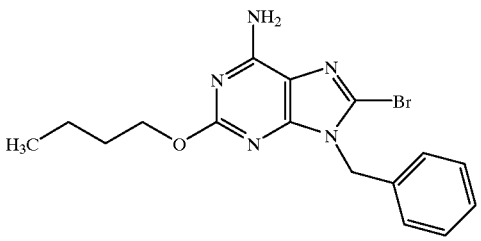

6-Amino-9-benzyl-2-butoxypurine (120 mg, 0.404 mmol) and bromine (0.5 ml) were dissolved in 50 ml of methylene chloride and the solution was stirred at room temperature for 5 hours. Aqueous sodium thiosulfate was added to the reaction mixture. The organic layer was separated and dried on sodium sulfate and evaporated in vacuo to dryness. The residue was purified with silica gel chromatography (1% methanol/chloroform) to give the subject compound (97 mg, yield 64%).

$^1$H-NMR(DMSO-$d_6$) δ: 7.44(2H, br s), 7.37–7.23(5H, m), 5.26(2H, s), 4.21(2H, t, J=6.4 Hz), 1.64(2H, m), 1.39(2H, m), 0.91(3H, t, J=7.3 Hz).

Reference Example 42

6-Amino-9-benzyl-8-bromo-2-pentoxypurine

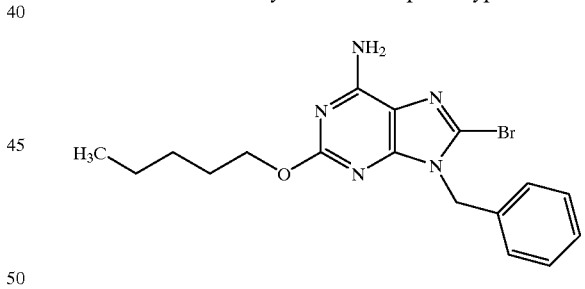

6-Amino-9-benzyl-2-pentoxypurine (95 mg, 0.305 mmol) and bromine (0.5 ml) were dissolved in 100 ml of methylene chloride and the solution was stirred at room temperature for 1 hour. Aqueous sodium thiosulfate was added to the reaction mixture. The organic layer was separated and dried on sodium sulfate and evaporated in vacuo to dryness. The residue was purified with silica gel chromatography (1% methanol/chloroform) to give the subject compound (78 mg, yield 82%).

$^1$H-NMR(DMSO-$d_6$) δ: 7.42(2H, br s), 7.37–7.22(5H, m), 5.25(2H, s), 4.19(2H, t, J=6.4 Hz), 1.66(2H, m), 1.33(4H, m), 0.88(3H, t, J=6.8 Hz).

Reference Example 43

2,6-Diamino-9-benzylpurine

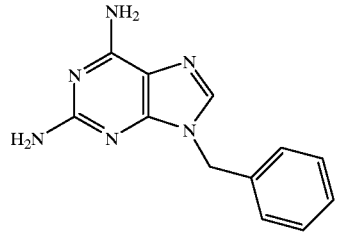

2,6-Diaminopurine (5.00 g, 33.3 mmol) and potassium carbonate (6.91 g, 50.0 mmol) were suspended in DMF (250 ml). Benzyl bromide (8.55 g, 50 mmol) was added thereto and the mixture was stirred at room temperature for 5 hours. After condensing the reaction mixture in vacuo, to the residue was added water and the mixture was extracted with chloroform. The organic layer was dried on sodium sulfate, filtered and the solvent in the filtrate was evaporated in vacuo. The residue was purified with silica gel chromatography (5% methanol/chloroform) to give the subject compound (1.56 g, yield 19%).

$^1$H-NMR(DMSO-$d_6$) δ: 7.78 (1H, s), 7.36–7.21 (5H, m), 6.69 (2H, br s), 5.80 (2H, br s), 5.19 (2H, s).

Reference Example 44

6-Amino-9-benzyl-2-methylaminopurine

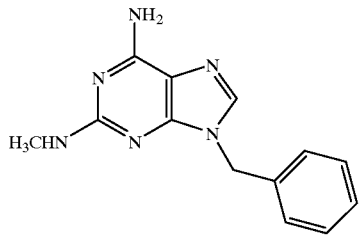

6-Amino-9-benzyl-2-chloropurine (200 mg, 0.77 mmol) and 40% methylamine/methanol solution (50 ml) were heated at 120° C. for 20 hours in autoclave. The reaction mixture was condensed in vacuo. To the residue was added 5N aqueous sodium hydroxide and the solution was extracted with chloroform. The organic layer was dried on sodium sulfate, filtered and the solvent in the filtrate was evaporated in vacuo. The residue was purified with silica gel chromatography (2% methanol/chloroform) to give the subject compound (163 mg, yield 83%).

$^1$H-NMR(DMSO-$d_6$) δ: 7.78 (1H, s), 7.36–7.26 (5H, m), 6.68 (2H, br s), 6.20 (1H, q, J=4.8 Hz), 5.19 (2H, s), 2.76 (3H, d, J=4.8 Hz).

Reference Example 45

6-Amino-9-benzyl-2-ethylaminopurine

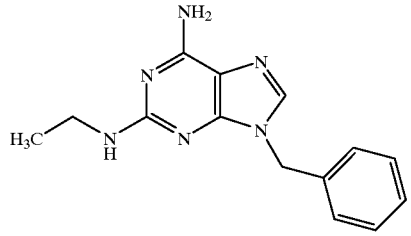

6-Amino-9-benzyl-2-chloropurine (200 mg, 0.77 mmol) and aqueous ethylamine (50 ml) were heated at 120° C. for 20 hours in autoclave. The reaction mixture was condensed in vacuo. To the residue was added 5N aqueous sodium hydroxide and the mixture was extracted with chloroform. The organic layer was dried on sodium sulfate, filtered and the solvent in the filtrate was evaporated in vacuo. The residue was purified with silica gel chromatography (2% methanol/chloroform) to give the subject compound (147 mg, yield 71%).

$^1$H-NMR(DMSO-$d_6$) δ: 7.78 (1H, s), 7.36–7.26 (5H, m), 6.65 (2H, br s), 6.22 (1H, t, J=5.7 Hz), 5.18 (2H, s), 3.26 (2H, m), 1.09 (3H, t, J=7.1 Hz).

Reference Example 46

6-Amino-9-benzyl-2-propylaminopurine

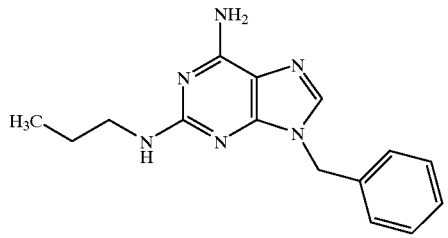

6-Amino-9-benzyl-2-chloropurine (10 mg, 0.385 mmol) and propylamine (228 mg, 3.85 mmol) in methanol (50 ml) were heated at 120° C. for 10 hours in autoclave. The reaction mixture was condensed in vacuo and to the residue was added 5N aqueous sodium hydroxide, followed by extraction with chloroform. The organic layer was dried on sodium sulfate, filtered and the solvent in the filtrate was evaporated in vacuo. The residue was purified with silica gel chromatography (2% methanol/chloroform) to give the subject compound (99 mg, yield 91%).

$^1$H-NMR(DMSO-$d_6$) δ: 7.78 (1H, s), 7.33–7.26 (5H, m), 6.64 (2H, br s), 6.25 (1H, t, J=5.7 Hz), 5.17 (2H, s), 3.18 (2H, m), 1.50 (2H, m), 0.87 (3H, t, J=7.5 Hz).

Reference Example 47

6-Amino-9-benzyl-2-butylamtnopurine

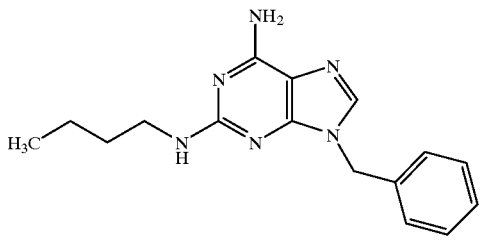

6-Amino-9-benzyl-2-chloropurine (100 mg, 0.38S5 mmol) and butylamine (282 mg, 3.85 mmol) in methanol (50 ml) were heated at 120° C. for 10 hours in autoclave. The reaction mixture was condensed in vacuo. To the residue was added 5N aqueous sodium hydroxide and the solution was extracted with chloroform. The organic layer was dried on sodium sulfate, filtered and the solvent in the filtrate was evaporated in vacuo. The residue was purified with silica gel chromatography (2% methanol/chloroform) to give the subject compound (113 mg, yield 99%).

$^1$H-NMR(DMSO-$d_6$) δ: 7.82 (1H, s), 7.34–7.26 (5H, m), 6.81 (2H, br s), 6.34 (1H, t, J=6.2 Hz), 5.18 (2H, s), 3.24 (2H, m), 1.49 (2H, m), 1.31 (2H, m), 0.88 (3H, t, J=7.3 Hz).

Reference Example 48

6-Amino-9-benzyl-2-pentylaminopurine

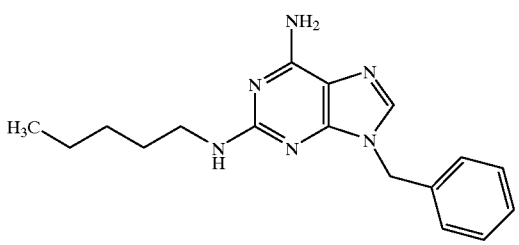

6-Amino-9-benzyl-2-chloropurine (100 mg, 0.385 mmol) and pentylamine (336 mg, 3.85 mmol) suspended in 1-butanol (10 ml) were heated at 100° C. for 10 hours in autoclave. The reaction mixture was condensed in vacuo. To the residue was added 1N aqueous sodium hydroxide and the solution was extracted with chloroform. The organic layer was dried on sodium sulfate, filtered and the solvent in the filtrate was evaporated in vacuo. The residue was purified with silica gel chromatography (2% methanol/chloroform) to give the subject compound (83 mg, yield 70%).

$^1$H-NMR(DMSO-$d_6$) δ: 7.79 (1H, s), 7.32–7.26 (5H, m), 6.62 (2H, br s), 6.21 (1H, t, J=6.0 Hz), 5.17 (2H, s), 3.25–3.18 (2H,m), 1.52–1.47 (2H, m), 1.30–1.26 (4H, m), 0.86 (3H, t, J=6.6 Hz).

Reference Example 49

6-Amino-9-benzyl-2-(isopropylamino)puring

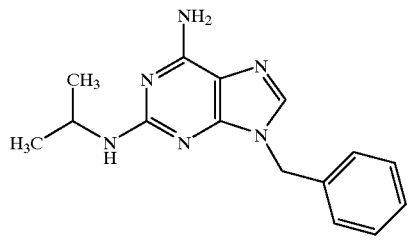

6-Amino-9-benzyl-2-chloropurine (100 mg, 0.385 mmol) and isopropylamine (228 mg, 3.85 mmol) suspended in 1-butanol (10 ml) were heated at 100° C. for 10 hours in autoclave. The reaction mixture was condensed in vacuo. To the residue was added 1N aqueous sodium hydroxide and the solution was extracted with chloroform. The organic layer was dried on sodium sulfate, filtered and the solvent in the filtrate was evaporated in vacuo. The residue was purified with silica gel chromatography (2% methanol/chloroform) to give the subject compound (89 mg, yield 82%).

$^1$H-NMR(DMSO-$d_6$) δ: 7.79 (1H, s), 7.36–7.26 (5H, m), 6.62 (2H, br s), 6.00 (1H, d, J=8.9 Hz), 5.17 (2H, s), 4.10–3.98 (1H, m), 1.11 (6H, d, J=6.6 Hz).

Reference Example 50

6-Amino-9-benzyl-2-(isobutylamino)purine

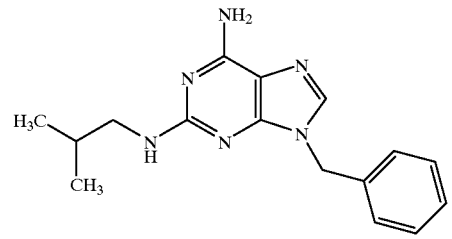

6-Amino-9-benzyl-2-chloropurine (100 mg, 0.385 mmol) and isobutylamine (288 mg, 3.85 mmol) suspended in 1-butanol (10 ml) were heated at 100° C. for 10 hours in autoclave. The reaction mixture was condensed in vacuo. To the residue was added 1N aqueous sodium hydroxide and the solution was extracted with chloroform. The organic layer was dried on sodium sulfate, filtered and the solvent in the filtrate was evaporated in vacuo. The residue was purified with silica gel chromatography (2% methanol/chloroform) to give the subject compound (89 mg, yield 78%).

$^1$H-NMR(DMSO-$d_6$) δ: 7.79 (1H, s), 7.33–7.26 (5H, m), 6.62 (2H, br s), 6.28 (1H, t, J=6.0 Hz), 5.17 (2H, s), 3.07 (2H, dd, J=6.0, 6.0 Hz), 1.89–1.79 (1H, m), 0.87 (6H, d, J=6.8 Hz).

Reference Example 51

6-Amino-9-benzyl-2-(sec-butylamino)purine

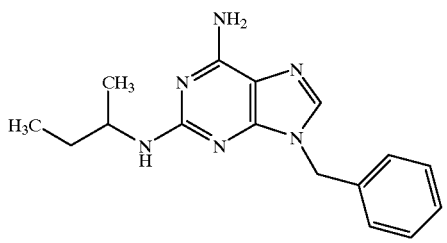

6-Amino-9-benzyl-2-chloropurine (100 mg, 0.385 mmol) and sec-butylamine (282 mg, 3.85 mmol) suspended in 1-butanol (10 ml) were heated at 100° C. for 10 hours in autoclave. The reaction mixture was condensed in vacuo. To the residue was added 1N aqueous sodium hydroxide and the mixture was extracted with chloroform. The organic layer was dried on sodium sulfate, filtered and the solvent in the filtrate was evaporated in vacuo. The residue was purified with silica gel chromatography (2% methanol/chloroform) to give the subject compound (71 mg, yield 62.8%).

$^1$H-NMR(DMSO-$d_6$) δ: 7.78 (1H, s), 7.33–7.26 (5H, m), 6.60 (2H, br s), 5.97 (1H, d, J=8.4 Hz), 5.17 (2H, s), 3.90–3.85 (1H, m), 1.54–1.38 (2H, m), 1.08 (3H, d, J=6.4 Hz), 0.85 (3H, t, J=7.3 Hz).

Reference Example 52

6-Amino-9-benzyl-2-(2,2-dimethylpropyl) aminopurine

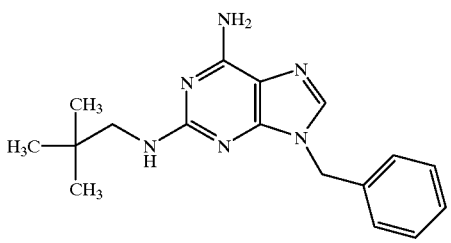

6-Amino-9-benzyl-2-chloropurine (100 mg, 0.385 mmol) and neo-pentylamine (336 mg, 3.85 mmol) suspended in 1-butanol (10 ml) were heated at 100° C. for 10 hours in autoclave. The reaction mixture was condensed in vacuo. To the residue was added 1N aqueous sodium hydroxide and the solution was extracted with chloroform. The organic layer was dried on sodium sulfate, filtered and the solvent in the filtrate was evaporated in vacuo. The residue was purified with silica gel chromatography (2% methanol/chloroform) to give the subject compound (88 mg, yield 74%).

$^1$H-NMR(DMSO-$d_6$) δ: 7.78 (1H, s), 7.32–7.24 (5H, m), 6.61 (2H, br s), 6.08 (1H, t, J=6.2 Hz), 5.17 (2H, s), 3.15 (2H, d, J=6.2 Hz), 0.87 (9H, s).

Reference Example 53

6-Amino-9-benzyl-2-benzylaminopurine

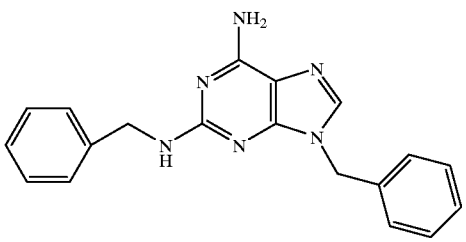

6-Amino-9-benzyl-2-chloropurine (200 mg, 0.77 mmol) and benzylamine (825 mg, 7.70 mmol) in 1-butanol (10 ml) were refluxed on heating for 8 hours. The reaction mixture was condensed in vacuo. To the residue was added 5N aqueous sodium hydroxide and the solution was extracted with chloroform. The organic layer was dried on sodium sulfate, filtered and the solvent in the filtrate was evaporated in vacuo. The residue was purified with silica gel chromatography (2% methanol/chloroform) to give the subject compound (171 mg, yield 67%).

$^1$H-NMR(DMSO-$d_6$) δ: 7.80 (1H, s), 7.34–7.15 (10H, m), 6.86 (1H, t, J=6.4 Hz), 6.69 (2H, br s), 5.15 (2H, s), 4.47 (2H, d, J=6.4 Hz).

Reference Example 54

6-Amino-9-benzyl-2-cyclohexylaminopurine

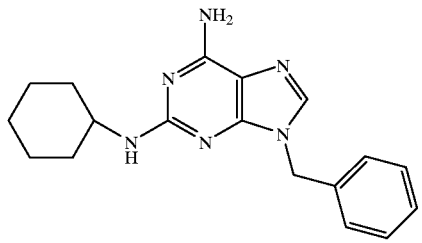

6-Amino-9-benzyl-2-chloropurine (200 mg, 0.77 mmol) and cyclohexylamine (764 mg, 7.70 mmol) in 1-butanol (10 ml) were refluxed on heating for 60 hours. The reaction mixture was condensed in vacuo. To the residue was added 5N aqueous sodium hydroxide and the solution was extracted with chloroform. The organic layer was dried on sodium sulfate, filtered and the solvent in the filtrate was evaporated in vacuo. The residue was purified with silica gel chromatography (2% methanol/chloroform) to give the subject compound (115 mg, yield 46%).

$^1$H-NMR(DMSO-$d_6$) δ: 7.79 (1H, s), 7.33–7.26 (5H, m), 6.60 (2H, br s), 6.00 (1H, d, J=8.1 Hz), 5.16 (2H, s), 3.71 (1H, m), 1.86 (2H, m), 1.72 (2H, m), 1.68 (1H, m), 1.31–1.14 (5H, m).

Reference Example 55

6-Amino-2-anilino-9-benzylpurine

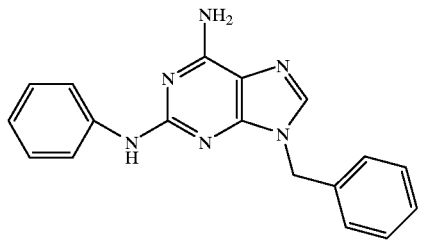

6-Amino-9-benzyl-2-chloropurine (100 mg, 0.385 mmol) and aniline (359 mg, 3.85 mmol) in 1-butanol (10 ml) were refluxed on heating for 20 hours. The reaction mixture was condensed in vacuo. To the residue was added 5N aqueous sodium hydroxide and the mixture was extracted with chloroform. The organic layer was dried on sodium sulfate, filtered and the solvent in the filtrate was evaporated in vacuo. The residue was purified with silica gel chromatography (2% methanol/chloroform) to give the subject compound (108 mg, yield 89%).

$^1$H-NMR(DMSO-d$_6$) δ: 8.88 (1H, s), 7.98 (1H, s), 7.81 (2H, d, J=7.9 Hz), 7.38–7.25 (5H, m), 7.20 (2H, t, J=8.3 Hz), 6.95 (2H, br s), 6.83 (1H, t, J=7.3 Hz), 5.29 (2H, s).

Reference Example 56

6-Amino-9-benzyl-2-dimethylaminopurine

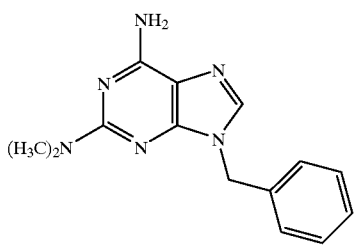

6-Amino-9-benzyl-2-chloropurine (100 mg, 0.385 mmol) and aqueous dimethylamine (30 ml) were heated at 120° C. for 15 hours in autoclave. The reaction mixture was condensed in vacuo. To the residue was added 5N aqueous sodium hydroxide and the solution was extracted with chloroform. The organic layer was dried on sodium sulfate, filtered and the solvent in the filtrate was evaporated in vacuo. The residue was purified with silica gel chromatography (2% methanol/chloroform) to give the subject compound (90 mg, yield 87%).

$^1$H-NMR(DMSO-d$_6$) δ: 7.82 (1H, s), 7.37–7.25 (5H, m), 6.73 (2H, br s), 5.19 (2H, s), 3.07 (6H, s).

Reference Example 57

6-Amino-9-benzyl-(N-benzylmethylamino)purine

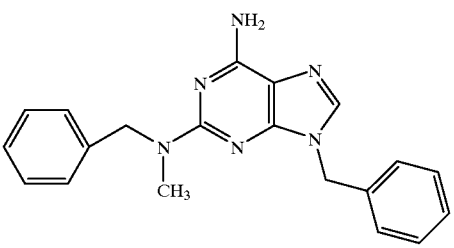

6-Amino-9-benzyl-2-chloropurine (100 mg, 0.385 mmol) and N-methylbenzylamine (467 mg, 3.85 mmol) in 1-butanol (30 ml) were refluxed on heating for 10 hours. The reaction mixture was condensed in vacuo. To the residue was added 5N aqueous sodium hydroxide and the mixture was extracted with chloroform. The organic layer was dried on sodium sulfate, filtered and the solvent in the filtrate was evaporated in vacuo. The residue was purified with silica gel chromatography (2% methanol/chloroform) to give the subject compound (97 mg, yield 73%).

$^1$H-NMR(DMSO-d$_6$) δ: 7.85 (1H, s), 7.35–7.19 (10H, m), 6.78 (2H, br s), 5.18 (2H, s), 4.85 (2H, s), 3.05 (3H, s).

Reference Example 58

2,6-Diamino-9-benzyl-8-bromopurine

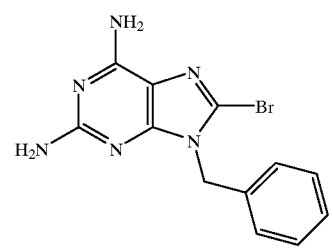

2,6-Diamino-9-benzylpurine (1.00 g, 4.16 mmol) and bromine (1 ml) were dissolved in 100 ml of methylene chloride and the solution was stirred at room temperature for 5 hours. Aqueous sodium thiosulfate was added to the reaction mixture. The organic layer was separated, dried on sodium sulfate and filtered. The solvent in the filtrate was evaporated in vacuo. The residue was purified with silica gel chromatography (1% methanol/chloroform) to give the subject compound (0.62 g, yield 47%).

$^1$H-NMR(DMSO-d$_6$) δ: 7.37–7.16 (5H, m), 6.92 (2H, br s), 5.99 (2H, br s), 5.18 (2H, s).

Reference Example 59

6-Amino-9-benzyl-8-bromo-2-methylaminopurine

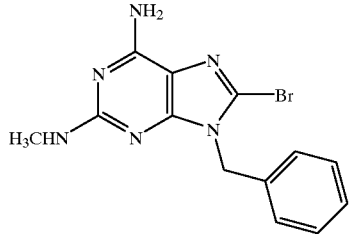

6-Amino-9-benzyl-2-methylaminopurine (75 mg, 0.30 mmol) and bromine (0.5 ml) were dissolved in 50 ml of methylene chloride and the solution was stirred at room temperature for 1 hour. Aqueous sodium thiosulfate was added to the reaction mixture. The organic layer was separated, dried on sodium sulfate and filtered. The solvent of the filtrate was evaporated in vacuo. The residue was purified with silica gel chromatography (1% methanol/chloroform) to give the subject compound (73 mg, yield 74%).

$^1$H-NMR(DMSO-$d_6$) δ: 7.38–7.22 (5H, m), 6.90 (2H, br s), 6.39 (1H, q, J=4.8 Hz), 5.18 (2H, s), 2.75 (3H, d, J=4.8 Hz).

Reference Example 60

6-Amino-9-benzyl-8-bromo-2-ethylaminopurine

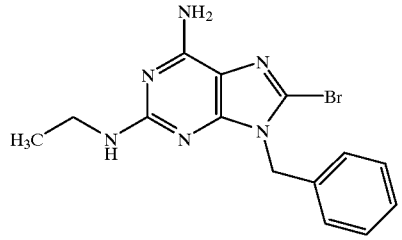

6-Amino-9-benzyl-2-ethylaminopurine (75 mg, 0.28 mmol) and bromine (0.5 ml) were dissolved in 50 ml of methylene chloride and the solution was stirred at room temperature for 1 hour. Aqueous sodium thiosulfate was added to the reaction mixture. The organic layer was separated, dried on sodium sulfate and filtered. The solvent in the filtrate was evaporated in vacuo. The residue was purified with silica gel chromatography (1% methanol/chloroform) to give the subject compound (63 mg, yield 65%).

$^1$H-NMR(DMSO-$d_6$) δ: 7.37–7.23 (5H, m), 6.87 (2H, br s), 6.41 (1H, t, J=5.5 Hz), 5.17 (2H, s), 3.25 (2H, m), 1.08 (3H, t, J=7.1 Hz).

Reference Example 61

6-Amino-9-benzyl-8-bromo-2-propylaminopurine

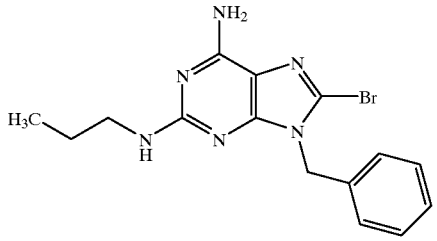

6-Amino-9-benzyl-2-propylaminopurine (87 mg, 0.31 mmol) and bromine (0.5 ml) were dissolved in 50 ml of methylene chloride and the solution was stirred at room temperature for 1 hour. Aqueous sodium thiosulfate was added to the reaction mixture. The organic layer was separated, dried on sodium sulfate and filtered. The solvent in the filtrate was evaporated in vacuo. The residue was purified with silica gel chromatography (1% methanol/chloroform) to give the subject compound (95 mg, yield 85%).

$^1$H-NMR(DMSO-$d_6$) δ: 7.37–7.23 (5H, m), 6.85 (2H, br s), 6.44 (1H, t, J=5.7 Hz), 5.17 (2H, s), 3.18 (2H, m), 1.50 (2H, m), 0.86 (3H, t, J=7.3 Hz).

Reference Example 62

6-Amino-9-benzyl-8-bromo-2-butylaminopurine

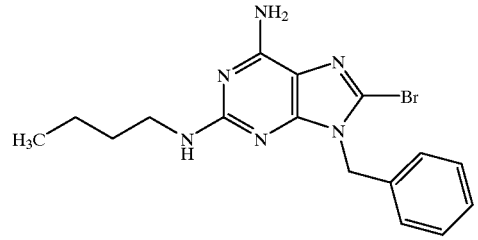

6-Amino-9-benzyl-2-butylaminopurine (101 mg, 0.34 mmol) and bromine (0.5 ml) were dissolved in 50 ml of methylene chloride and the solution was stirred at room temperature for 1 hour. Aqueous sodium thiosulfate was added to the reaction mixture. The organic layer was separated, dried on sodium sulfate and filtered. The solvent in the filtrate was evaporated in vacuo. The residue was purified with silica gel chromatography (1% methanol/chloroform) to give the subject compound (116 mg, yield 91%).

$^1$H-NMR(DMSO-$d_6$) δ: 7.36–7.26 (5H, m), 6.85 (2H, br s), 6.42 (1H, t, J=6.2 Hz), 5.17 (2H, s), 3.22 (2H, m), 1.46 (2H, m), 1.30 (2H, m), 0.87 (3H, t, J=7.3 Hz).

Reference Example 63

6-Amino-9-benzyl-8-bromo-2-pentylaminopurine

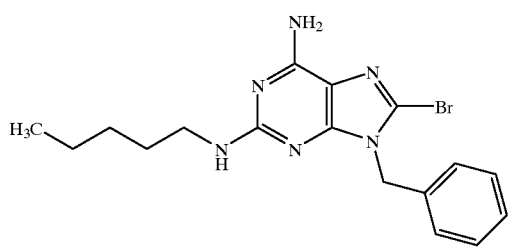

6-Amino-9-benzyl-2-pentylaminopurine (70 mg, 0.23 mmol) and bromine (0.5 ml) were dissolved in 50 ml of methylene chloride and the solution was stirred at room temperature for 1 hour. Aqueous sodium thiosulfate was added to the reaction mixture. The organic layer was separated, dried on sodium sulfate and filtered. The solvent in the filtrate was evaporated in vacuo. The residue was purified with silica gel chromatography (1% methanol/chloroform) to give the subject compound (80 mg, yield 91%).

$^1$H-NMR(DMSO-d$_6$) δ: 7.37–7.24 (5H, m), 6.84 (2H, br s), 6.41 (1H, t, J=5.7 Hz), 5.17 (2H, s), 3.25–3.18 (2H,m), 1.52–1.47 (2H, m), 1.29–1.24 (4H, m), 0.85 (3H, t, J=6.9 Hz).

Reference Example 64

6-Amino-9-benzyl-8-bromo-2-(isopropylamino)purine

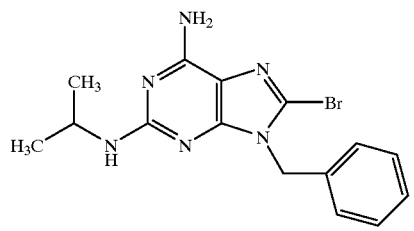

6-Amino-9-benzyl-2-(isopropylamino)purine (71 mg, 0.25 mmol) and bromine (0.5 ml) were dissolved in 50 ml of methylene chloride and the solution was stirred at room temperature for 1 hour. Aqueous sodium thiosulfate was added to the reaction mixture. The organic layer was separated, dried on sodium sulfate and filtered. The solvent in the filtrate was evaporated in vacuo. The residue was purified with silica gel chromatography (1% methanol/chloroform) to give the subject compound (73 mg, yield 81%).

$^1$H-NMR(DMSO-d$_6$) δ: 7.38–7.23 (5H, m), 6.84 (2H, br s), 6.21 (1H, d, J=8.1 Hz), 5.17 (2H, s), 4.09–3.99 (1H, m), 1.11 (6H, d, J=6.4 Hz).

Reference Example 65

6-Amino-9-benzyl-8-bromo-2-(isobutylamino)purine

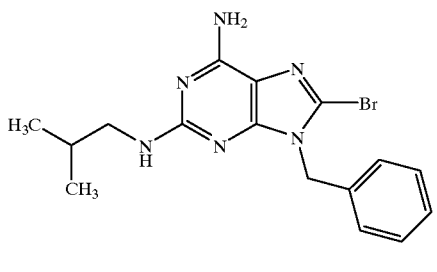

6-Amino-9-benzyl-2-(isobutylamino)purine (75 mg, 0.25 mmol) and bromine (0.5 ml) were dissolved in 50 ml of methylene chloride and the solution was stirred at room temperature for 1 hour. Aqueous sodium thiosulfate was added to the reaction mixture. The organic layer was separated, dried on sodium sulfate and filtered. The solvent of the filtrate was evaporated in vacuo. The residue was purified with silica gel chromatography (1% methanol/chloroform) to give the subject compound (62 mg, yield 65%).

$^1$H-NMR(DMSO-d$_6$) δ: 7.37–7.27 (5H, m), 6.83 (2H, br s), 6.47 (1H, t, J=6.0 Hz), 5.17 (2H, s), 3.06 (2H, dd, J=6.0, 6.0 Hz), 1.88–1.78 (1H, m), 0.86 (6H, d, J=6.8 Hz).

Reference Example 66

6-Amino-9-benzyl-8-bromo-2-(sec-butylamino)purine

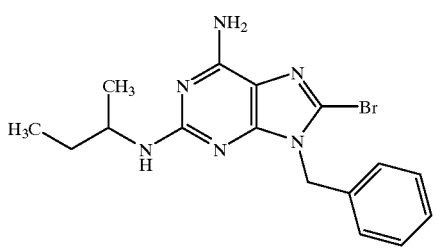

6-Amino-9-benzyl-2-(sec-butylamino)purine (58 mg, 0.20 mmol) and bromine (0.5 ml) were dissolved in 50 ml of methylene chloride and the solution was stirred at room temperature for 1 hour. Aqueous sodium thiosulfate was added to the reaction mixture. The organic layer was separated, dried on sodium sulfate and filtered. The solvent in the filtrate was evaporated in vacuo. The residue was purified with silica gel chromatography (1% methanol/chloroform) to give the subject compound (57 mg, yield 78%).

$^1$H-NMR(DMSO-d$_6$) δ: 7.35–7.25 (5H, m), 6.80 (2H, br s), 6.16 (1H, d, J=8.6 Hz), 5.15 (2H, s), 3.88–3.81 (1H, m), 1.50–1.36 (2H, m), 1.05 (3H, d, J=6.4 Hz), 0.83 (3H, t, J=7.3 Hz).

Reference Example 67

6-Amino-9-benzyl-8-bromo-2-(2,2-dimethylpropyl)aminopurine

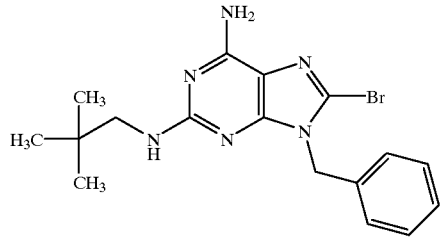

6-Amino-9-benzyl-2-(2,2-dimethyipropyl)aminopurine (69 mg, 0.22 mmol) and bromine (0.5 ml) were dissolved in 50 ml of methylene chloride and the solution was stirred at room temperature for 1 hour. Aqueous sodium thiosulfate was added to the reaction mixture. The organic layer was separated, dried on sodium sulfate and filtered. The solvent in the filtrate was evaporated in vacuo. The residue was purified with silica gel chromatography (1% methanol/chloroform) to give the subject compound (75 mg, yield 87%).

$^1$H-NMR(DMSO-d$_6$) δ: 7.36–7.23 (5H, m), 6.82 (2H, br s), 6.29 (1H, t, J=6.2 Hz), 5.18 (2H, s), 3.14 (2H, d, J=6.2 Hz), 0.86 (9H, s).

Reference Example 68

6-Amino-9-benzyl-2-(N-benzylamino)-8-bromopurine

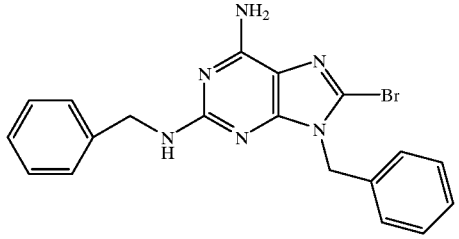

6-Amino-9-benzyl-2-(N-benzylamino)purine (60 mg, 0.18 mmol) and bromine (0.5 ml) were dissolved in 50 ml of methylene chloride and the solution was stirred at room temperature for 1 hour. Aqueous sodium thiosulfate was added to the reaction mixture. The organic layer was separated, dried on sodium sulfate and filtered. The solvent in the filtrate was evaporated in vacuo. The residue was purified with silica gel chromatography (1% methanol/chloroform) to give the subject compound (37 mg, yield 50%).

$^1$H-NMR(DMSO-d$_6$) δ: 7.33–7.20 (10H, m), 7.05 (1H, t, J=6.4 Hz), 6.91 (2H, br s), 5.15 (2H, s), 4.46 (2H, d, J=6.4 Hz).

Reference Example 69

6-Amino-9-benzyl-8-bromo-2-cyclohexylaminopurine

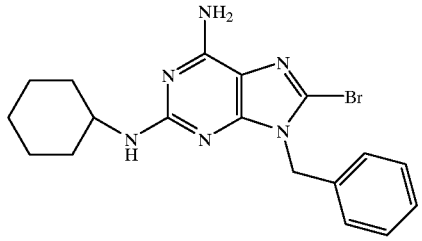

6-Amino-9-benzyl-2-cyclohexylaminopurine (100 mg, 0.31 mmol) and bromine (0.5 ml) were dissolved in 50 ml of methylene chloride and the solution was stirred at room temperature for 1 hour. Aqueous sodium thiosulfate was added to the reaction mixture. The organic layer was separated, dried on sodium sulfate and filtered. The solvent in the filtrate was evaporated in vacuo. The residue was purified with silica gel chromatography (1% methanol/chloroform) to give the subject compound (105 mg, yield 84%).

$^1$H-NMR(DMSO-d$_6$) δ: 7.37–7.27 (5H, m), 6.81 (2H, br s), 6.20 (1H, d, J=7.9 Hz), 5.16 (2H, s), 3.68 (1H, m), 1.87 (2H, m), 1.69 (2H, m), 1.58 (1H, m), 1.30–1.12 (5H, m).

Reference Example 70

6-Amino-2-anilino-9-benzyl-8-bromopurine

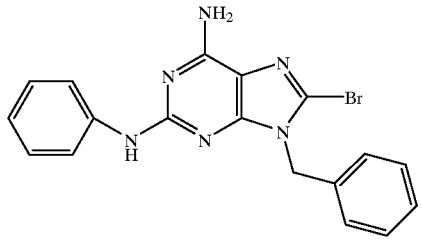

6-Amino-2-anilino-9-benzylpurine (87 mg, 0.31 mmol) was dissolved in a mixture of methylene chloride (50 ml) and acetic acid (10 ml). To the solution were added sodium acetate (105 mg, 1.28 mmol) and bromine (0.5 ml), and the mixture was stirred at room temperature for 3 hour. Aqueous sodium thiosulfate was added to the reaction mixture. The organic layer was separated, washed with aqueous saturated sodium hydrogen carbonate, dried on sodium sulfate and filtered. The solvent in the filtrate was evaporated in vacuo. The residue was purified with silica gel chromatography (1% methanol/chloroform) to give the subject compound (93 mg, yield 92%).

$^1$H-NMR(DMSO-d$_6$) δ: 8.30 (1H, d, J=8.8 Hz), 7.82 (1H, d, J=2.4 Hz), 7.71 (1H, s), 7.49 (1H, dd, J=9.0, 2.4 Hz), 7.39–7.25 (9H, m), 5.27 (2H, s).

Reference Example 71

6-Amino-9-benzyl-8-bromo-2-dimethylaminopurine

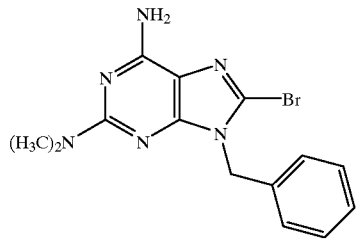

6-Amino-9-benzyl-2-dimethylaminopurine (66 mg, 0.25 mmol) was dissolved in a mixture of methylene chloride (50 ml) and acetic acid (10 ml). To the solution were added sodium acetate (202 mg, 2.46 mmol) and bromine (0.5 ml), and the mixture was stirred at room temperature for 1 hour. Aqueous sodium thiosulfate was added to the reaction mixture. The organic layer was separated, washed with aqueous saturated sodium hydrogen carbonate, dried on sodium sulfate and filtered. The solvent in the filtrate was evaporated in vacuo. The residue was purified with silica gel chromatography (1% methanol/chloroform) to give the subject compound (68 mg, yield 80%).

$^1$H-NMR(DMSO-d$_6$) δ: 7.38–7.25 (5H, m), 6.95 (2H, br s), 5.19 (2H, s), 3.07 (6H, s).

Reference Example 72

6-Amino-9-benzyl-2-(N-benzylmethylamino)-8-bromopurine

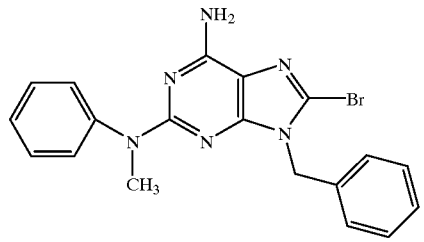

6-Amino-9-benzyl-2-(N-benzylmethylamino)purine (77 mg, 0.22 mmol) and bromine (0.5 ml) were dissolved in 50 ml of methylene chloride and the solution was stirred at room temperature for 1 hour. Aqueous sodium thiosulfate was added to the reaction mixture. The organic layer was separated, dried on sodium sulfate and filtered. The solvent in the filtrate was evaporated in vacuo. The residue was purified with silica gel chromatography (1% methanol/chloroform) to give the subject compound (91 mg, yield 96%).

$^1$H-NMR(DMSO-d$_6$) δ: 7.31–7.19 (10H, m), 7.00 (2H, br s), 5.18 (2H, s), 4.84 (2H, s), 3.05 (3H, s).

Reference Example 73

5-Amino-1-benzyl-4-cyano-2-hydroxyimidazole

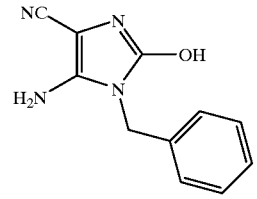

Benzylisocyanate (25 g, 188 mmol) and N,N-diisopropylethylamine (23.5 ml, 130 mmol) were added to aminomalononitrile p-toluenesulfonate (45 g, 178 mmol) suspended in tetrahydrofuran. The mixture was stirred at room temperature for 14 hours and then the solvent was removed in vacuo. To the residue was added ethyl acetate and the solution was washed and the organic layer was dried on magnesium sulfate. The solvent was removed in vacuo. To the residue was added tetrahydrofuran and 1N aqueous sodium hydroxide. The solution was stirred at 50° C. for 20 minutes, and neutralized with 15% aqueous potassium hydrogen sulfide. The resulting crystals were filtered and dried to give the subject compound (41 g, 106%). The crude product was used for next reaction without further purification.

$^1$H NMR (δ, DMSO-d$_6$): 9.91 (s, 1H), 7.31 (m, 5H), 6.51(br s, 2H), 4.76 (s, 2H).

Reference Example 74

1-Amino-9-benzyl-8-hydroxy-2-mercaptpurine

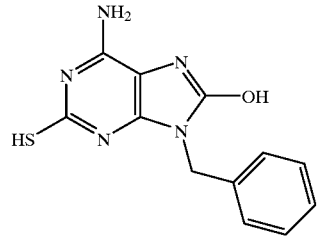

Crude 5-amino-1-benzyl-4-cyano-2-hydroxyimidazole (31.3 g, 146 mmol) of Reference Example 73 was suspended in tetrahydrofuran and to the suspension was dropped benzoylisothiocyanate (41 ml, 305 mmol). After stirring overnight, the solvent was removed in vacuo and to the residue was added ether. The crystals were filtered and dissolved in a mixture of tetrahydrofuran and 2N aqueous sodium hydroxide. The solution was refluxed for 50 hours and then, neutralized with 10% aqueous potassium hydrogen sulfide. The resulting crystals were filtered to give a mixture (27.8 g) of the subject compound and 6-amino-7-benzyl-8-hydroxy-2-mercaptpurine. The mixture was recrystallized from ethyl acetate to give only the subject compound.

$^1$H NMR (δ, DMSO-d$_6$): 12.10 (br s, 1H), 10.06 (br s, 1H), 7.36–7.24 (m, 5H), 6.74 (br s, 2H), 4.85 (s, 2H).

Reference Example 75

6-Amino-9-benzyl-2,8-dimethoxypurine

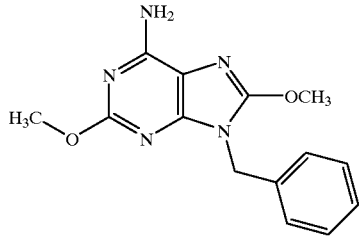

To 6-amino-9-benzyl-8-bromo-2-methoxypurine (125 mg, 0.374 mmol) in 10 ml of methanol was added 10N aqueous sodium hydroxide (50 ml) and the solution was refluxed under heating for 2 hours. The reaction mixture was concentrated in vacuo to dryness and to the residue was added water. The mixture was extracted with chloroform and the organic layer was dried on sodium sulfate. After removal of the solvent the residue was purified with silica gel chromatography (1% methanol/chloroform) to give the subject compound (83 mg, yield 78%).

$^1$H-NMR(DMSO-$d_6$) δ: 7.73–7.23(5H, m), 6.90(2H, br s), 5.05(2H, s), 4.04(3H, s), 3.78(3H, s).

Reference Example 76

6-Amino-9-benzyl-2-ethoxy-8-methoxypurine

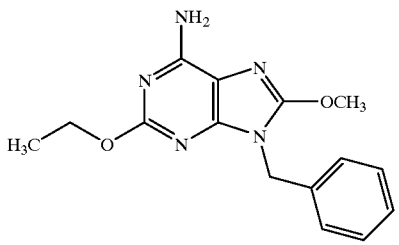

To 6-amino-9-benzyl-8-bromo-2-ethoxypurine (35 mg, 0.101 mmol) in 5 ml of methanol was added 10N aqueous sodium hydroxide (50 ml) and the solution was refluxed under heating for 2 hours. The reaction mixture was concentrated in vacuo to dryness and to the residue was added water. The mixture was extracted with chloroform and the organic layer was dried on sodium sulfate. After removal of the solvent the residue was purified with silica gel chromatography (1% methanol/chloroform) to give the subject compound (22 mg, yield 73%).

$^1$H-NMR(DMSO-$d_6$) δ: 7.73–7.23(5H, m), 6.86(2H, br s), 5.04(2H, s), 4.22(2H, q, J=7.1 Hz), 4.04(3H, s), 1.27(3H, t, J=7.1 Hz).

Reference Example 77

6-Amino-9-benzyl-8-methoxy-2-propoxypurine

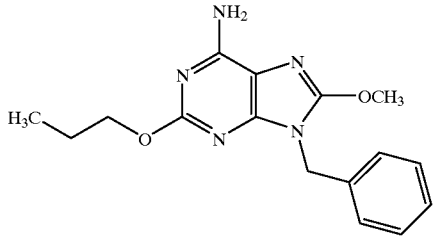

To 6-amino-9-benzyl-8-bromo-2-propoxypurine (123 mg, 0.339 mmol) in 10 ml of methanol was added 10N aqueous sodium hydroxide (50 ml) and the solution was refluxed under heating for 2 hours. The reaction mixture was concentrated in vacuo to dryness and to the residue was added water. The mixture was extracted with chloroform and the organic layer was dried on sodium sulfate. After removal of the solvent the residue was purified with silica gel chromatography (1% methanol/chloroform) to give the subject compound (99 mg, yield 93%).

$^1$H-NMR(DMSO-$d_6$) δ: 7.36–7.22(5H, m), 6.86(2H, br s), 5.04(2H, s), 4.12(2H, t, J=6.8 Hz), 4.04(3H, s), 1.67(2H, m), 0.94(3H, t, J=7.3 Hz).

Reference Example 78

6-Amino-9-benzyl-2-(2-methoxyethyl)aminopurine

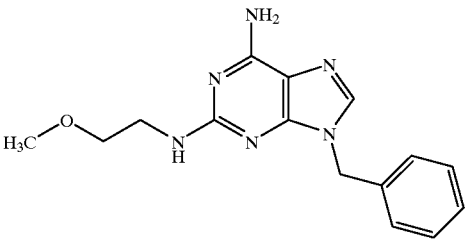

6-Amino-9-benzyl-2-chloropurine (10 mg, 0.385 mmol) and 2-methoxyethylamine in 2 ml of butanol were heated at 120° C. for 9 hours in autoclave. The reaction mixture was concentrated in vacuo to dryness and to the residue was added water. The mixture was extracted with chloroform and the organic layer was dried on sodium sulfate and concentrated in vacuo to dryness. The residue was purified with silica gel chromatography (3% methanol/chloroform) to give the subject compound (83 mg, yield 72%).

$^1$H-NMR(DMSO-$d_6$) δ: 7.81(1H, s), 7.35–7.26(5H, m), 6.72(2H, br s), 6.18(1H, t, J=4.8 Hz), 5.19(2H, s), 3.45–3.36 (4H, m), 3.24(3H, s).

Reference Example 79

6-Amino-9-benzyl-8-bromo-2-(2-methoxyethylamino)purine

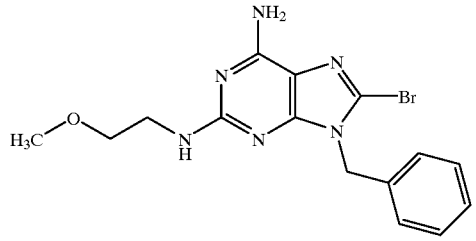

6-Amino-9-benzyl-2-(2-methoxyethyl)aminopurine (70 mg, 0.24 mmol) and bromine (0.5 ml) were dissolved in methylene chloride (50 ml). The solution was stirred at room temperature for 1 hour. Aqueous sodium thiosulfate was added to the reaction mixture. The organic layer was separated, dried on sodium sulfate and concentrated in vacuo to dryness. The residue was purified with silica gel chromatography (1% methanol/chloroform) to give the subject compound (71 mg, yield 80%).

$^1$H-NMR(DMSO-d$_6$) δ: 7.36–7.23(5H, m), 6.94(2H, br s), 6.38(1H, t, J=4.8 Hz), 5.18(2H, s), 3.45–3.36(4H, m), 3.23 (3H, s).

Reference Example 80

6-Amino-9-benzyl-8-methoxy-2-(2-methoxyethyl]aminopurine

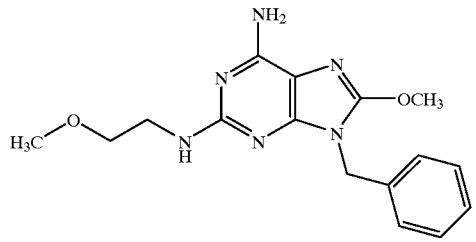

6-Amino-9-benzyl-8-bromo-2-(2-methoxyethyl)aminopurine (68 mg, 0.18 mmol) was dissolved in 28% sodium methoxide in methanol (30 ml) and the solution was refluxed on heating under stirring for 4 hours. The reaction mixture was concentrated in vacuo to dryness and to the residue was added water. The mixture was extracted with chloroform and the organic layer was dried on sodium sulfate and concentrated in vacuo to dryness. The residue was purified with silica gel chromatography (2% methanol/chloroform) to give the subject compound (26 mg, yield 44%).

$^1$H-NMR(DMSO-d$_6$) δ: 7.35–7.21(5H, m), 6.36(2H, br s), 6.01 (1H, t, J=4.8 Hz), 4.98(2H, s), 3.99(3H, s), 3.45–3.36 (4H, m), 3.23 (3H, S).

Reference Example 81

6-Amino-9-benzyl-8-methoxy-2-(2-ethoxyethoxy)purine

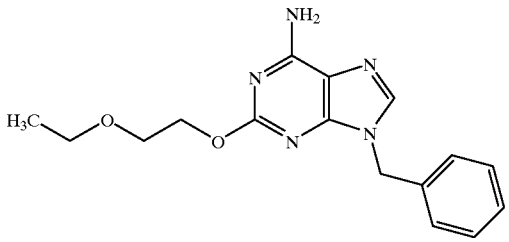

6-Amino-9-benzyl-2-chloropurine (500 mg, 1.93 mmol) was dissolved in 40 ml of sodium 2-ethoxyethoxy in 2-ethoxyethanol and the solution was heated at 100° C. for 6 hours. The reaction mixture was concentrated in vacuo to dryness and to the residue was added water. The mixture was extracted with chloroform and the organic layer was washed with water, dried on sodium sulfate and concentrated in vacuo to dryness. The residue was purified with silica gel chromatography (2% methanol/chloroform) to give the subject compound (410 mg, yield 68%).

$^1$H-NMR(DMSO-d$_6$) δ: 8.05(1H, s), 7.38–7.26(5H, m), 7.24(2H, br s), 5.26(2H, s), 4.32(2H, t, J=4.8 Hz), 3.65(2H, t, J=4.8 Hz), 3.47(2H, q, J=7.0 Hz), 1.11(3H, t, J=7.0 Hz).

Reference Example 82

6-Amino-9-benzyl-8-bromo-2-(2-ethoxyethoxy)purine

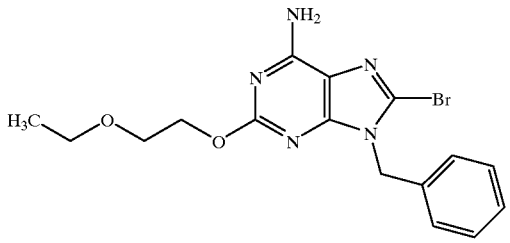

6-Amino-9-benzyl-2-(2-ethoxyethoxy)purine (300 mg, 0.96 mmol) and bromine (2.0 ml) were dissolved in methylene chloride (50 ml). The solution was stirred at room temperature for 1 hour. Aqueous sodium thiosulfate was added to the reaction mixture. The organic layer was separated, dried on sodium sulfate and concentrated in vacuo to dryness. The residue was purified with silica gel chromatography (1% methanol/chloroform) to give the subject compound (256 mg, yield 68%).

$^1$H-NMR(DMSO-d$_6$) δ: 7.47(2H, br s), 7.39–7.23(5H, m), 5.26(2H, s), 4.32(2H, t, J=4.8 Hz), 3.65(2H,t, J=4.8 Hz), 3.47(2H, q, J=7.0 Hz), 1.11(3H, t, J=7.0 Hz).

Reference Example 83

6-Amino-9-benzyl-2-(2-ethoxyethoxyl-8-methoxypurine

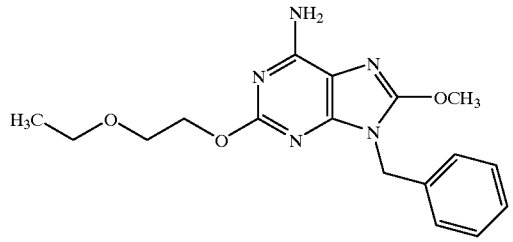

6-Amino-9-benzyl-8-bromo-2-(2-ethoxyethoxy)purine (206 mg, 0.18 mmol) was dissolved in 1N sodium hydroxide in methanol (20 ml) and the mixture was refluxed on heating under stirring for 2 hours. The reaction mixture was concentrated in vacuo to dryness, and to the residue was added water. The solution was extracted with chloroform and the organic layer was dried on sodium sulfate and concentrated in vacuo to dryness. The residue was purified with silica gel chromatography (2% methanol/chloroform) to give the subject compound (123 mg, yield 68%).

$^1$H-NMR(DMSO-d$_6$) δ: 7.36–7.23(5H, m), 6.89(2H, br s), 5.04(2H, s), 4.29(2H, t, J=4.6 Hz), 4.05(3H, s), 3.64(2H, t, J=4.6 Hz), 3.47(2H, q, J=7.0 Hz), 1.11(3H, t, J=7.0 Hz).

Reference Example 84

6-Amino-2-chloro-9-(4-fluorobenzyl)purine

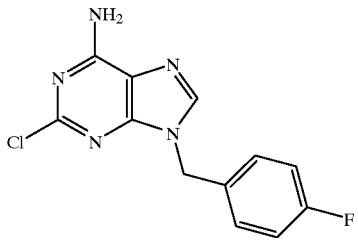

6-Amino-2-chloropurine (5.02 g) and potassium carbonate (5 g, 36 mmol) were suspended in DMF (200 ml) and thereto was added 4-fluorobenzyl chloride (5 ml, 42 mmol). The mixture was stirred at room temperature for 3 hours. The reaction mixture was concentrated in vacuo to dryness, and to the residue was added water. The mixture was extracted with chloroform and the organic layer was washed with water, dried on sodium sulfate and concentrated in vacuo to dryness. The residue was purified with silica gel chromatography (2% methanol/chloroform) to give the subject compound (162 g).

$^1$H-NMR(DMSO-dE) δ: 8.25(1H, s), 7.80(2H, br s), 7.37 (5H, m), 7.18(2H, m), 5.33(2H, s).

Reference Example 85

6-Amino-9-(4-fluorobenzyl)-2-(2-methoxyethoxy)purine

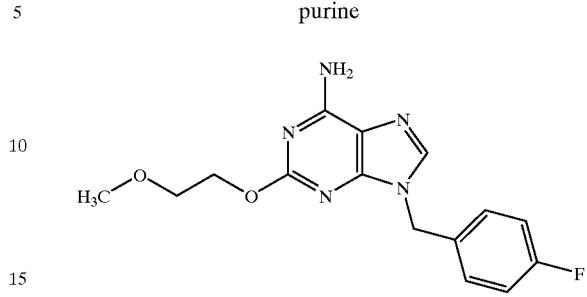

6-Amino-9-(4-fluorobenzyl)purine (100 mg, 0.36 mmol) was dissolved in 30 ml of sodium 2-mehoxyethoxide in 2-methoxyethanol and the solution was heated at 20° C. for 3 hours. The reaction mixture was concentrated in vacuo to dryness and to the residue was added water. The mixture was extracted with chloroform and the organic layer was washed with water, dried on sodium sulfate and concentrated in vacuo to dryness. The residue was purified with silica gel chromatography (2% methanol/chloroform) to give the subject compound (109 mg, yield 95%).

$^1$H-NMR(DMSO-d$_6$) δ: 8.05(1H, s), 7.40 (2H, m), 7.24 (2H, br s), 7.17(2H, m), 5.25(2H, s), 4.33(2H, t, J=4.4 Hz), 3.62(2H, t, J=4.4 Hz), 3.29(3H, s).

Reference Example 86

6-Amino-8-bromo-9-(fluorobenzyl)-2-(2-methoxyethoxy)purine

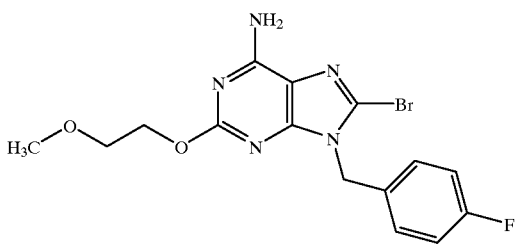

6-Amino-9-(4-fluorobenzyl)-2-(2-methoxyethoxy)purine (mg, 0.96 mmol) and bromine (1.0 ml) were dissolved in methylene chloride (20 ml). The solution was stirred at room temperature for 1 hour. Aqueous sodium thiosulfate was added to the reaction mixture. The organic layer was separated, dried on sodium sulfate and concentrated in vacuo to dryness. The residue was purified with silica gel chromatography (1% methanol/chloroform) to give the subject compound (79 mg, yield 69%).

$^1$H-NMR(DMSO-d$_6$) δ: 7.46(2H, br s), 7.31(2H, m), 7.19(2H, m), 5.24(2H, s), 4.34(2H, t, J=4.6 Hz), 3.62(2H,t, J=4.6 Hz), 3.29(3H, s).

Reference Example 87

6-Amino-9-(4-fuluorobenzyl)-8-methoxy-2-(2-methoxyethoxy)purine

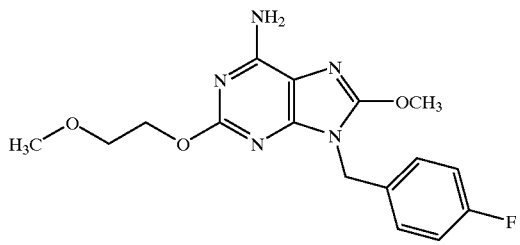

6-Amino-8-bromo-9-(4-fluorobenzyl)-2-(2-methoxyethoxy)purine (70 mg, 0.18 mmol) was dissolved in 1N sodium hydroxide in methanol (20 ml) and the solution was refluxed on heating under stirring for 2 hours. The reaction mixture was concentrated in vacuo to dryness, and to the residue was added water. The mixture was extracted with chloroform and the organic layer was dried on sodium sulfate and concentrated in vacuo to dryness. The residue was purified with silica gel chromatography (2% methanol/chloroform) to give the subject compound (57 mg, yield 93%).

$^1$H-NMR(DMSO-$d_6$) δ: 7.31(2H, m), 7.16(2H, m), 6.87 (2H, br s), 5.02(2H, s), 4.30(2H, t, J=4.6 Hz), 4.05(3H, s), 3.61(2H, t, J=4.6 Hz), 3.29(3H, s).

Reference Example 88

5-Amino-4-cyano-1-(4-fluorobenzyl)-2-hydroxyimidazole

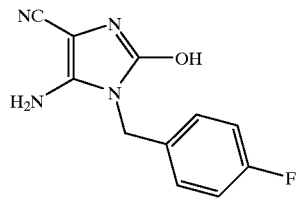

4-Fluorobenzylisocyanate (1.37 g, 10 mmol) and N,N-diisopropylethylamine (1.29 g, 10 mmol) were added to aminomalononitrile p-toluenesulfonate (2.53 g, 10 mmol) suspended in tetrahydrofuran (50 ml). The mixture was stirred at room temperature for 24 hours and then the solvent was removed in vacuo. To the residue was added ethyl acetate and the solution was washed and the organic layer was extracted with 1N aqueous sodium hydroxide. The extract was neutralized with 10% aqueous potassium hydrogen sulfide and extracted with ethyl acetate. The organic layer was dried on sodium sulfate and the solvent was removed in vacuo. The residue was purified with silica gel chromatography (1% methanol/chloroform) to give the subject compound (1.93 g, yield 89%).

$^1$H-NMR (DMSO-$d_6$): 9.93(1H, br s), 7.31(2H, m), 7.15 (2H, m), 6.53(2H, br s), 4.75(2H, s).

Reference Example 89

6-Amino-9-(4-fluorobenzyl)-8-hydroxy-2-thiopurine

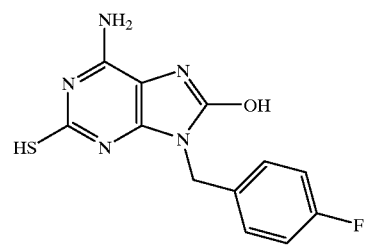

5-amino-4-cyano-1-(4-fluorobenzyl)-2-hydroxyimidazole (1.90 g, 8.79 mmol) was suspended in tetrahydrofuran (50 ml) and to the suspension was dropped benzoylisothiocyanate (2.87 g, 17.6 mmol). After stirring at room temperature for 8 hours, the solvent was removed in vacuo and to the residue was added ether. The crystals were filtered and refluxed in a mixture of tetrahydrofuran and 1N aqueous sodium hydroxide for 40 hours and neutralized with 10% aqueous potassium hydrogen sulfide. The crystals were harvested by filtration to give the subject compound (1.22 g, yield: 48%).

$^1$H NMR (δ, DMSO-$d_6$): 10.14(1H, s), 7.31(2H, m), 7.15(2H, m), 6.83(2H, s), 4.84(2H, s).

Reference Example 90

6-Amino-9-benzyl-2,8-dihydroxypurine

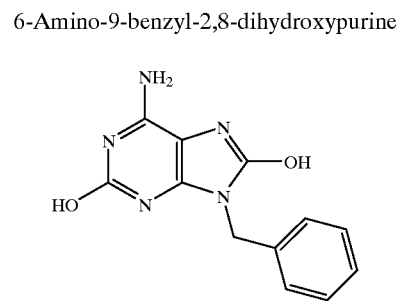

6-Amino-9-benzyl-8-bromo-2-methoxypurine (75 mg, 0.224 mmol) in concentrated hydrochloric acid (15 ml) was refluxed under heating for 5 hours. The reaction mixture was made basic by 28% aqueous ammonia, the crystals were filtered, washed with water and purified by silica gel chromatography (0.2%aqueous ammonia-5% methanol/chroloform) to give the subject compound (12 mg, yield 21%).

$^1$H-NMR(DMSO-$d_6$) δ: 9.64(2H, br s), 7.34–7.22(6H, m), 6.51(2H, br s), 4.78(2H, s).

Reference Example 91

2,6-Diamino-9-benzyl-8-purinol

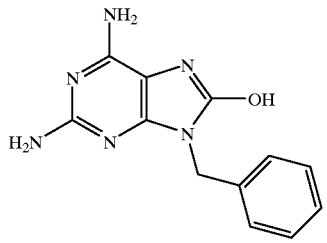

2,6-Diamino-9-benzyl-8-bromopurine (400 mg, 1.25 mmol) in concentrated hydrochloric acid (20 ml) was refluxed under heating for 5 hours. The reaction mixture was made basic by 28% aqueous ammonia, the crystals were filtered, washed with water and dried to give the subject compound (138 mg, yield 43%).

$^1$H-NMR(DMSO-d$_6$) δ: 9.63 (1H, br s), 7.34–7.22 (5H, m), 6.02 (2H, br s), 5.74 (2H, br s), 4.81 (2H, s).

Reference Example 92

6-Amino-9-benzyl-2-(2-aminoethyl)thiopurine

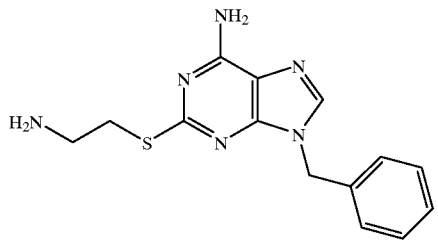

To sodium hydride (300 mg, 7.5 mmol, 60% in mineral oil) were added DMF (10 ml), 2-aminoethanethiol (620 mg, 8 mmol) and 6-amino-9-benzyl-2-chloropurine (200 mg, 0.77 mmol) in order. The mixture was stirred at 100° C. for 3 hours. After addition of saturated brine the reaction mixture was extracted with chloroform and the organic layer was dried on magnesium sulfate and concentrated in vacuo to dryness. The residue was purified with silica gel chromatography (10% methanol/chloroform) to give the subject compound (126 mg, yield 54%).

$^1$H NMR (CDCl$_3$) δ: 7.64 (s, 1H), 7.31–7.26 (m, 5H), 5.53 (br s, 2H), 5.29 (s, 2H), 3.26 (t, 2H, J=6.0 Hz), 3.02 (t, 2H, J=6.3 Hz).

Reference Example 93

6-Amino-9-benzyl-2-(2-dimethylaminoethyl)thiopurine

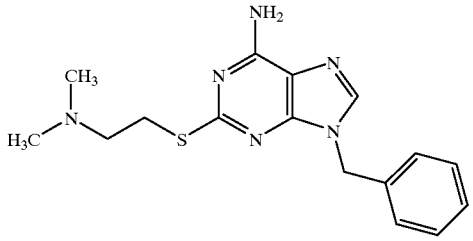

To sodium hydride (600 mg, 15 mmol 60% in mineral oil) were added DMF (10 ml), 2-dimethylaminoethanethiol (1.3 g, 9.2 mmol) and 6-amino-9-benzyl-2-chloropurine (100 mg, 0.39 mmol) in order. The mixture was stirred at 100° C. for 10 hours. After addition of saturated brine the reaction mixture was extracted with chloroform and the organic layer was dried on magnesium sulfate and concentrated in vacuo to dryness. The residue was purified with silica gel chromatography (10% methanol/chloroform) to give the subject compound (24 mg, yield 21%).

$^1$H NMR (CDCl$_3$) δ: 7.63 (s, 1H), 7.36–7.26 (m, 5H), 5.55 (br s, 2H), 5.30 (s, 2H), 3.29 (t, 2H, J=7.6 Hz), 2.68 (t, 2H, J=7.9 Hz), 2.30 (s, 6H), 1.80 (br s, 2H).

Reference Example 94

3-(6-Amino-9-benzyl-2-purinyl)thiopropionic Acid

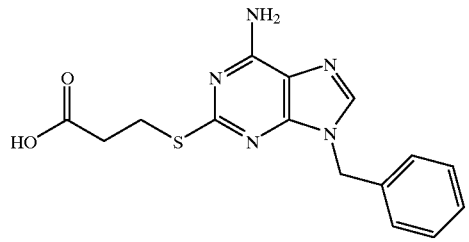

To sodium hydride (300 mg, 7.5 mmol 60% in mineral oil) were added DMF (10 ml), 3-mercaptopropionic acid (1 ml, 11 mmol) and 6-amino-9-benzyl-2-chloropurine (200 mg, 0.77 mmol) in order. The mixture was stirred at 100° C. for 5 hours. After addition of saturated brine, the reaction mixture was acidified with 2N hydrochloric acid and extracted with chloroform. The organic layer was dried on magnesium sulfate and concentrated in vacuo to dryness. The residue was purified with silica gel chromatography (4% methanol/chloroform) to give the subject compound (120 mg, yield 47%).

$^1$H NMR (DMSO-d$_6$) δ: 12.26 (br s, 1H); 8.16 (s, 1H), 7.39–7.17 (m, 5H), 5.29 (s, 2H), 3.22 (t, 2H, J=7.2 Hz), 2.66 (t, 2H, J=6.9 Hz).

Reference Example 95

2-(2-Acetylaminoethyl)thio-6-amino-9-benzylpurine

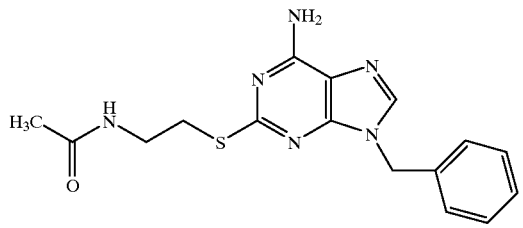

To 6-amino-9-benzyl-2-(2-aminoethyl)thiopurine (50 mg, 0.17 mmol) suspended in 2 ml of dichloromethane was added triethylamine (30 ml, 0.2 mmol) and then acetic acid anhydride (20 ml, 0.2 mmol) under ice cooling. After 1 hour the mixture warmed to room temperature. Thereto was added saturated brine. The mixture was extracted with chloroform and the organic layer was dried on magnesium sulfate and concentrated in vacuo to dryness. The residue was purified with silica gel chromatography (1% methanol/chloroform) to give the subject compound (34 mg, yield 66%).

$^1$H NMR (CDCl$_3$) δ: 7.67 (s, 1H), 7.34–7.26 (m, 5H), 6.17 (br s, 3H), 5.31 (s, 2H), 3.59 (q, 2H, J=5.6 Hz), 3.31 (t, 2H, J=5.2 Hz).

Reference Example 96

Methyl-3-(6-amino-9-benzyl-2-purinyl)thiopropionate

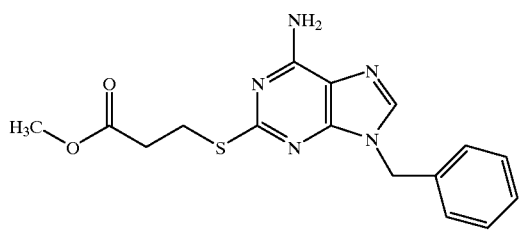

To 3-(6-amino-9-benzyl-2-purinyl) thiopropionic acid (100 mg, 0.30 mmol) suspended in 10 ml of chloroform was added thionylchloride (0.14 ml, 2 mmol). After refluxing under heating for 1 hour methanol was dropped to the mixture under ice cooling. The solvent was removed in vacuo and the residue was purified by silica gel chromatography (1% methanol/chloroform) to give the subject compound (70 mg, yield 68%).

$^1$H NMR (CDCl$_3$) δ: 7.65 (s, 1H), 7.36–7.26 (m, 5H), 5.67 (br s, 2H), 5.28 (s, 2H), 3.69 (s, 3H), 3.39 (t, 2H, J=7.3 Hz), 2.82 (t, 2H, J=7.6 Hz).

Reference Example 97

N-Methyl-(6-amino-9-benzyl-2-purinyl)thioacetamide

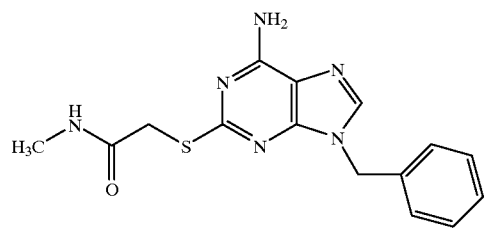

Sodium hydride (320 mg, 8 mmol 60% in mineral oil) was washed with hexane. Thereto were added DMF (10 ml), 2-mercapto-N-methylacetamide (1 ml) and 6-amino-9-benzyl-2-chloropurine (200 mg, 0.77 mmol) in order. The mixture was stirred at 100° C. for 8 hours. After addition of saturated brine the reaction mixture was extracted with ethyl acetate. The organic layer was dried on magnesium sulfate and the solvent was removed in vacuo. The residue was purified with silica gel chromatography (3% methanol/chloroform) to give the subject compound (158 mg, yield 60%).

$^1$H NMR (DMSO-d$_6$) δ: 8.14 (s, 1H), 7.87 (br s, 1H), 7.33 (m, 5H), 5.30 (s, 2H), 3.75 (s, 2H), 2.53 (d, 3H, J=4.6 Hz).

Reference Example 98

3-(6-Amino-9-benzyl-2-purinyl)thio-1-propanol

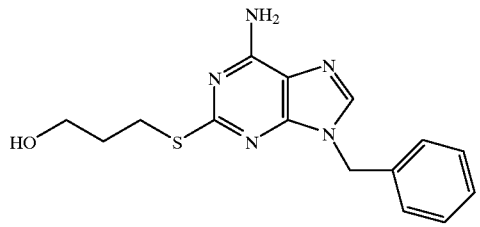

Sodium hydride (600 mg, 15 mmol 60% in mineral oil) were added DMF (10 ml), 3-mercapto-1-propanol (1 ml, 12 mmol) and 6-amino-9-benzyl-2-chloropurine (200 mg, 0.77 mmol) in order. The mixture was stirred at 100° C. for 2 hours. After addition of saturated brine the reaction mixture was extracted with ethyl acetate. The organic layer was dried on magnesium sulfate and the solvent was removed in vacuo. The residue was purified with silica gel chromatography (1% methanol/chloroform) to give the subject compound (30 mg, yield 12%).

$^1$H NMR (CDCl$_3$) δ: 7.62 (s, 1H), 7.37–7.26 (m, 5H), 5.59 (br s, 2H), 5.29 (s, 2H), 3.76 (m, 3H), 3.33 (t, 2H, J=6.3 Hz), 1.96 (m, 2H).

119

Reference Example 99

3-(6-Amino-9-benzyl-2-purinylithio-1-propanethiol

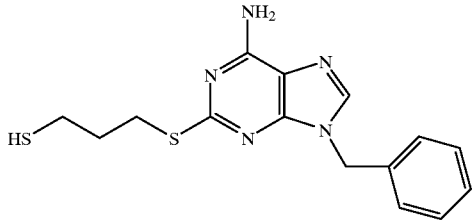

Sodium hydride (600 mg, 15 mmol 60% in mineral oil) were added DMF (10 ml), 1,3-propanedithiol (1 ml, 10 mmol) and 6-amino-9-benzyl-2-chloropurine (200 mg, 0.77 mmol) in order. The mixture was stirred at 100° C. for 2 hours. After addition of saturated brine the reaction mixture was extracted with ethyl acetate. The organic layer was dried on magnesium sulfate and the solvent was removed in vacuo. The residue was purified with silica gel chromatography (1% methanol/chloroform) to give the subject compound (135 mg, yield 53%).

$^1$H NMR (CDCl$_3$) δ: 7.65 (s, 1H), 7.36–7.26 (m, 5H), 5.56 (br s, 2H), 5.31 (s, 2H), 3.28 (t, 2H, J=6.6 Hz), 2.65 (m, 2H), 2.05 (m, 2H), 1.40 (t, 1H, J=7.9 Hz).

Reference Example 100

6-Amino-9-benzyl-2-(2-phenylethyl)thiopurine

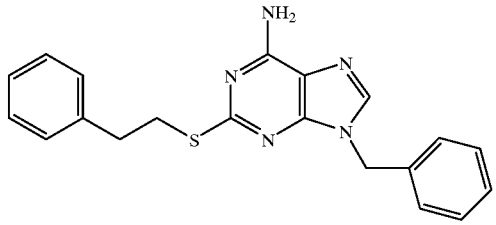

Sodium hydride (300 mg, 7.5 mmol 60% in mineral oil) were added DMF (10 ml), 2-phenylethanethiol (1 ml, 7 mmol) and 6-amino-9-benzyl-2-chloropurine (100 mg, 0.39 mmol) in order. The mixture was stirred at 100° C. for 10 hours. After addition of saturated brine the mixture was extracted with ethyl acetate. The organic layer was dried on magnesium sulfate and the solvent was removed in vacuo. The residue was purified with silica gel chromatography (1% methanol/chloroform) to give the subject compound (51 mg, yield 37%).

$^1$H NMR (CDCl$_3$) δ: 7.65 (s, 1H), 7.32–7.24 (m, 5H), 5.57 (br s, 2H), 5.33 (s, 2H), 3.39 (dd, 2H, J=10.6, 7.6 Hz), 3.07 (dd, 2H, J=15.8, 7.2 Hz).

120

Reference Example 101

6-Amino-9-benzyl-2-(2-hydroxyethoxy)purine

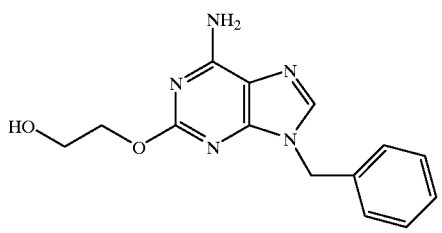

To sodium (74 mg, 3.2 mmol) in 5 ml of ethylene glycol were added 6-amino-9-benzyl-2-chloropurine (157 mg, 0.58 mmol). The mixture was heated at 100° C. for 4 hours and concentrated in vacuo to dryness. To the residue was added water and the mixture was extracted with chloroform. The organic layer was dried on magnesium sulfate and the solvent was removed in vacuo. The residue was purified with silica gel chromatography (3% methanol/chloroform) to give the subject compound (121 mg, yield 70%).

$^1$H-NMR(DMSO-d$_6$) δ: 8.04(1H, s), 7.32(5H, m), 7.22 (2H, br s), 5.25(2H, s), 4.81(1H, t, J=5.3 Hz), 4.22(2H, t, J=4.9 Hz), 3.68(2H, q, J=5.3 Hz).

Reference Example 102

6-Amino-9-benzyl-8-bromo-2-(2-hydroxyethoxy) purine

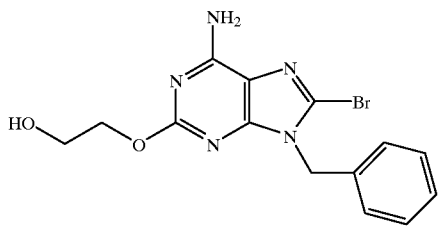

6-Amino-9-benzyl-2-(2-methoxyethoxy)purine (100 mg, 0.36 mmol) and bromine (0.25 ml) were dissolved in methylene chloride (100 ml). The solution was stirred at room temperature for 6 hours. Aqueous sodium thiosulfate was added to the reaction mixture. The organic layer was separated, dried on sodium sulfate and the solvent was removed in vacuo. The residue was purified with silica gel chromatography (2% methanol/chloroform) to give the subject compound (55 mg, yield 43%).

$^1$H-NMR(DMSO-d$_6$) δ: 7.44(2H, br s), 7.36–7.23(5H, m), 5.25(2H, s), 4.82(1H, t, J=5.6 Hz), 4.22(2H, t, J=5.0 Hz), 3.66(2H, q, J=5.0 Hz).

Reference Example 103

6-Amino-9-benzyl-2-(2-hydroxyethoxyl)-8-methoxypurine

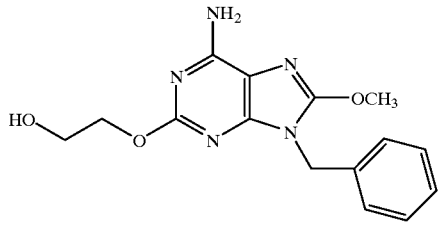

6-Amino-9-benzyl-8-bromo-2-(2-methoxyethoxyl)purine (130 mg, 0.36 mmol) in methanol (50 ml) was dissolved in 28% sodium methoxide/methanol (3 ml) and the solution was refluxed on heating under stirring for 10 hours. The reaction mixture was concentrated in vacuo to dryness, and to the residue was added saturated brine. The mixture was extracted with chloroform and the organic layer was dried on sodium sulfate, followed by removal of the solvent. The residue was purified with silica gel chromatography (3% methanol/chloroform) to give the subject compound (78 mg, yield 69%).

$^1$H-NMR(DMSO-d$_6$) δ: 7.26(5H, m), 6.86(2H, br s), 5.03(2H, s), 4.78(1H, t, J=5.6 Hz), 4.18(2H, t, J=5.0 Hz), 4.04(3H, s), 3.66(2H, m).

Reference Example 104

6-Amino-9-benzyl-2-(3-hydroxypropoxy)purine

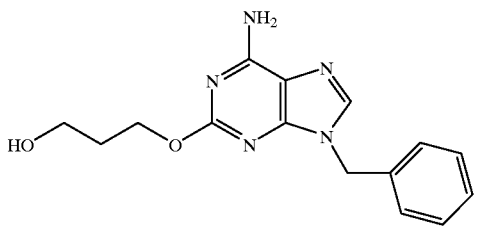

Sodium (80 mg, 3.5 mmol) in 3 ml of 1,3-propanediol was added 6-amino-9-benzyl-2-chloropurine (235 mg, 0.90 mmol). The mixture was heated at 100° C. for 3 hours. The reaction mixture was concentrated in vacuo to dryness. To the residue was added water and the mixture was extracted with chloroform. The organic layer was dried on sodium sulfate and the solvent was removed. The residue was purified with silica gel chromatography (3% methanol/chloroform) to give the subject compound (137 mg, yield 51%).

$^1$H-NMR(DMSO-d$_6$) δ: 8.03(1H, s), 7.32(5H, m), 7.21 (2H, br s), 5.25(2H, s), 4.51(1H, t, J=4.9 Hz), 4.26(2H, t, J=6.3 Hz), 3.52(2H, q, J=5.6 Hz), 1.81(2H, m).

Reference Example 105

6-Amino-9-benzyl-8-bromo-2-(3-hydroxypropoxy)purine

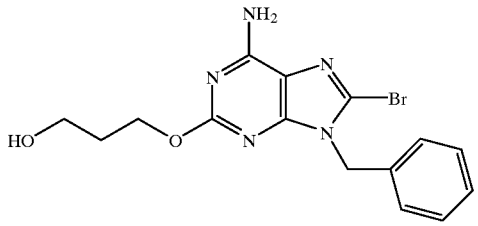

6-Amino-9-benzyl-2-(3-hydroxypropoxy)purine (210 mg, 0.7 mmol) and bromine (0.5 ml) were dissolved in methylene chloride (200 ml). The solution was stirred at room temperature for 4 hours. Aqueous sodium thiosulfate was added to the reaction mixture. The organic layer was separated, dried on magnesium sulfate and concentrated in vacuo to dryness. The residue was purified with silica gel chromatography (5% methanol/chloroform) to give the subject compound (143 mg, yield 54%).

$^1$H-NMR(DMSO-d$_6$) δ: 7.45(2H, br s), 7.32(5H, m), 5.25(2H, s), 4.52(1H, t, J=5.0 Hz), 4.26(2H, t, J=6.6 Hz), 3.52(2H, q, J=5.6 Hz), 1.81(2H, m).

Reference Example 106

6-Amino-9-benzyl-2-(3-hydroxypropoxy)-8-methoxypurine

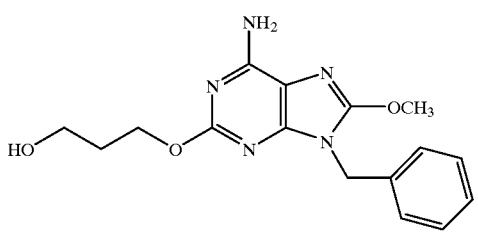

6-Amino-9-benzyl-8-bromo-2-(3-hydroxypropoxy) purine (140 mg, 0.37 mmol) in methanol (50 ml) was dissolved in 28%. sodium methoxide/methanol (3 ml) and the solution was refluxed on heating under stirring for 10 hours. The reaction mixture was concentrated in vacuo to dryness and to the residue was added saturated brine. The mixture was extracted with chloroform and the organic layer was dried on sodium sulfate and the solvent was removed. The residue was purified with silica gel chromatography (3% methanol/chloroform) to give the subject compound (88 mg, yield 72%).

$^1$H-NMR(DMSO-d$_6$) δ: 7.31(5H, m), 6.86(2H, br s), 5.04(2H, s), 4.50(1H, t, J=5.0 Hz), 4.22(2H, t, J=6.6 Hz), 4.03(3H, s), 3.52(2H, m), 1.80(2H, m).

Reference Example 107

6-Amino-9-benzyl-2-(3-ethoxypropoxy)purine

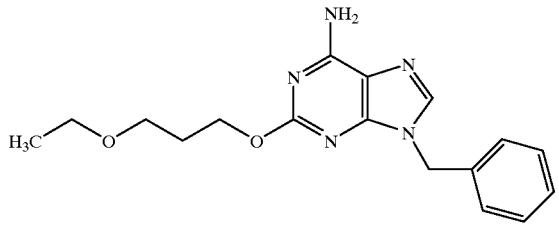

To sodium (150 mg, 6.5 mmol) in 5 ml of 3-ethoxypropanol were added 6-amino-9-benzyl-2-chloropurine (500 mg, 1.93 mmol) and DMF (10 ml). The mixture was heated at 120° C. for 1 hour. The reaction mixture was concentrated in vacuo to dryness. To the residue was added water and the mixture was extracted with chloroform. The organic layer was dried on sodium sulfate and the solvent was removed. The residue was purified with silica gel chromatography (2% methanol/chloroform) to give the subject compound (481 mg, yield 76%).

$^1$H-NMR(DMSO-d$_6$) δ: 8.04(1H, s), 7.34–7.25(5H, m), 7.24(2H, br s), 5.27(2H, s), 4.27(2H, t, J=6.4 Hz), 3.48(2H, t, J=6.4 Hz), 3.41(2H, q, J=7.0 Hz), 1.91(2H, m), 1.10(3H, t, J=7.0 Hz).

Reference Example 108

6-Amino-9-benzyl-8-bromo-2-(3-ethoxypropoxy)purine

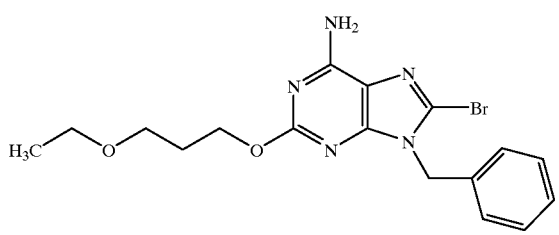

6-Amino-9-benzyl-2-(3-ethoxypropoxy)purine (354 mg, 1.08 mmol) and bromine (1.0 ml) were dissolved in methylene chloride (50 ml). The solution was stirred at room temperature for 2 hours. Aqueous sodium thiosulfate was added to the reaction mixture. The organic layer was separated, dried on sodium sulfate and the solvent was removed. The residue was purified with silica gel chromatography (1% methanol/chloroform) to give the subject compound (289 mg, yield 66%).

$^1$H-NMR(DMSO-d$_6$) δ: 7.37(2H, br s), 7.36–7.23(5H, m), 5.26(2H, s), 4.26(2H, t, J=6.4 Hz), 3.47(2H, t, J=6.4 Hz), 3.40(2H, q, J=7.0 Hz), 1.90(2H, m), 1.09(3H, t, J=7.0 Hz).

Reference Example 109

6-Amino-9-benzyl-2-(3-ethoxypropoxy)-8-methoxypurine

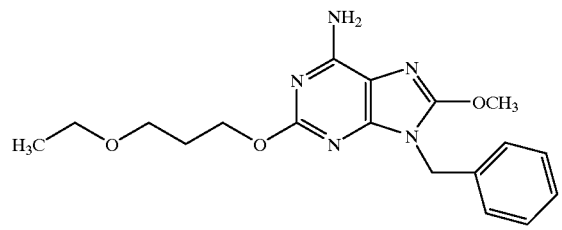

To 6-amino-9-benzyl-8-bromo-2-(3-ethoxypropoxy)purine (250 mg, 0.36 mmol) in 20 ml of methanol was added 1N aqueous sodium hydroxide (80 ml). The mixture was refluxed on heating under stirring for 2 hours. The reaction mixture was concentrated in vacuo to dryness. To the residue was added water and the mixture was extracted with chloroform. The organic layer was dried on sodium sulfate and the solvent was removed. The residue was purified with silica gel chromatography (2% methanol/chloroform) to give the subject compound (187 mg, yield 85%).

$^1$H-NMR(DMSO-d$_6$) δ: 7.36–7.23(5H, m), 6.88(2H, br s), 5.05(2H, s), 4.23(2H, t, J=6.4 Hz), 4.05(3H, s), 3.47(2H, t, J=6.4 Hz), 3.38(2H, q, J=7.0 Hz), 1.89(2H, m), 1.10(3H, t, J=7.0 Hz).

Reference Example 110

6-Amino-9-benzyl-2-(4-hydroxybutoxy)purine

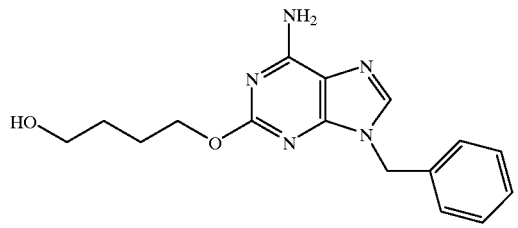

Sodium (150 mg, 6.5 mmol) in 5 ml of 1,5-butanediol were added 6-amino-9-benzyl-2-chloropurine (500 mg, 1.93 mmol) and DMF (10 ml). The mixture was heated at 120° C. for 1 hour. The reaction mixture was concentrated in vacuo to dryness. To the residue was added water and the mixture was extracted with chloroform. The organic layer was dried on sodium sulfate and the solvent was removed. The residue was purified with silica gel chromatography (3% methanol/chloroform) to give the subject compound (336 mg, yield 56%).

$^1$H-NMR(DMSO-d$_6$) δ: 8.04(1H, s), 7.37–7.25(5H, m), 7.22(2H, br s), 5.26(2H, s), 4.46(1H, t, J=5.3 Hz), 4.22(2H, t, J=6.6 Hz), 3.43(2H, m), 1.71(2H, m), 1.53(2H, m).

Reference Example 111

6-Amino-9-benzyl-8-bromo-2-(4-hydroxybutoxy)purine

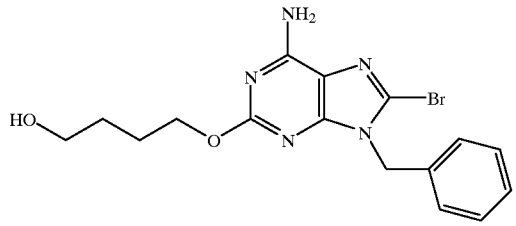

6-Amino-9-benzyl-2-(4-hydroxybutoxy)purine (200 mg, 0.638 mmol) and bromine (1.0 ml) were dissolved in methylene chloride (50 ml). The solution was stirred at room temperature for 2 hours. Aqueous sodium thiosulfate was added to the reaction mixture. The organic layer was separated, dried on sodium sulfate and the solvent was removed. The residue was purified with silica gel chromatography (2% methanol/chloroform) to give the subject compound (213 mg, yield 85%).

$^1$H-NMR(DMSO-$d_6$) δ: 7.44(2H, br s), 7.39–7.24(5H, m), 5.26(2H, s), 4.45(1H, t, J=5.1 Hz)$_1$ 4.23(2H, t, J=6.6 Hz), 3.44(2H, m), 1.71(2H, m), 1.54(2H, m).

Reference Example 112

6-Amino-9-benzyl-2-(4-hydroxybutoxy)-8-methoxypurine

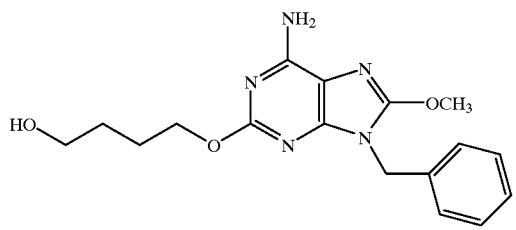

To 6-amino-9-benzyl-8-bromo-2-(4-hydroxybutoxy)purine (185 mg, 0.472 mmol) in 10 ml of methanol was added 1N aqueous sodium hydroxide (40 ml). The mixture was refluxed on heating under stirring for 2 hours. The reaction mixture was concentrated in vacuo to dryness. To the residue was added water and the mixture was extracted with chloroform. The organic layer was dried on sodium sulfate and the solvent was removed. The residue was purified with silica gel chromatography (2% methanol/chloroform) to give the subject compound (123 mg, yield 68%).

$^1$H-NMR(DMSO-$d_6$) δ: 7.37–7.23(5H, m), 6.87(2H, br s), 5.04(2H, s), 4.43(1H, br s), 4.18(2H, t, J=6.4 Hz), 3.43(2H, t, J=6.6 Hz), 1.68(2H, m), 1.53(2H, m).

Reference Example 113

6-Amino-9-benzyl-2-(2-methoxyethoxy)purine

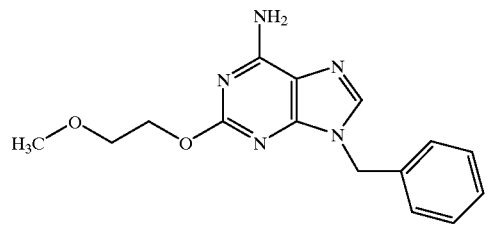

Sodium (66 mg, 2.9 mmol) in 50 ml of 2-methoxyethanol was added 6-amino-9-benzyl-2-chloropurine (150 mg, 0.58 mmol) and DMF (10 ml). The mixture was heated at 130° C. for 6 hour. The reaction mixture was concentrated in vacuo to dryness. To the residue was added water and the mixture was extracted with chloroform. The organic layer was dried on sodium sulfate and concentrated in vacuo to dryness. The residue was purified with silica gel chromatography (3% methanol/chloroform) to give the subject compound (123 mg, yield 71%).

$^1$H-NMR(DMSO-$d_6$) δ: 8.05(1H, s), 7.36–7.27(5H, m), 7.23(2H, br s), 5.26(2H, s), 4.32(2H, t, J=4.6 Hz), 3.61(2H, t, J=4.6 Hz), 3.28(3H, s).

Reference Example 114

6-Amino-9-benzyl-8-bromo-2-(2-methoxyethoxy)purine

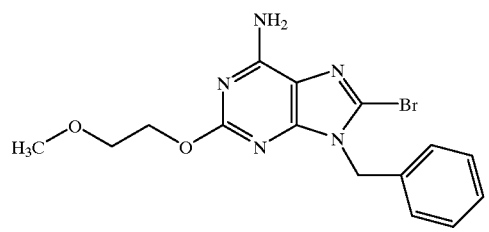

6-Amino-9-benzyl-2-(2-methoxyethoxy)purine (93 mg, 0.31 mmol) and bromine (1 ml) were dissolved in methylene chloride (100 ml). The solution was stirred at room temperature for 1 hour. Aqueous sodium thiosulfate was added to the reaction mixture. The organic layer was separated, dried on sodium sulfate and concentrated in vacuo to dryness. The residue was purified with silica gel chromatography (1% methanol/chloroform) to give the subject compound (75 mg, yield 64%).

$^1$H-NMR(DMSO-$d_6$) δ: 7.46(2H, br s), 7.38–7.23(5H, m), 5.25(2H, s), 4.33(2H, t, J=4.6 Hz), 3.61(2H, t, J=4.6 Hz), 3.28(3H, s).

Reference Example 115

6-Amino-9-benzyl-8-methoxy-2-(2-methoxyethoxy)purine

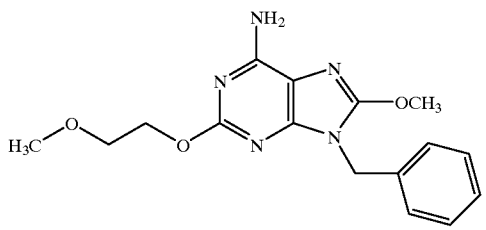

6-Amino-9-benzyl-8-bromo-2-(2-methoxyethoxy)purine (69 mg, 0.18 mmol) in methanol (50 ml) was dissolved in 28% sodium methoxide/methanol (1 ml) and the mixture was refluxed on heating under stirring for 5 hours. The reaction mixture was concentrated in vacuo to dryness, and to the residue was added water. The solution was extracted with chloroform and the organic layer was dried on sodium sulfate and concentrated in vacuo to dryness. The residue was purified with silica gel chromatography (3% methanol/chloroform) to give the subject compound (26 mg, yield 43%).

$^1$H-NMR(DMSO-d$_6$) δ: 7.36–7.23(5H, m), 6.88(2H, br s), 5.04(2H, s), 4.29(2H, t, J=4.6 Hz), 4.04(3H, s), 3.60(2H, t, J=4.6 Hz), 3.28(3H, s).

INDUSTRIAL APPLICABILITY

According to the present invention an interferon inducer containing a compound of the present invention as an active agent is provided. The interferon inducer of the present invention has inducing and activating activity for biosynthesis of interferon and therefore, is useful as therapeutic agents based on biological activities of interferon, such as antiviral activity, preventing activity of cell growth, immune modulation etc., that is, therapeutic agents for virus infected diseases (e.g. hepatitis C, hepatitis B), anticancer agents and agents for immunologic diseases.

What is claimed is:

1. A heterocyclic compound of the following formula (I):

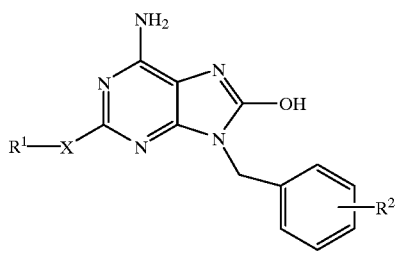

(I)

wherein X is sulfur atom, oxygen atom or —NR$^{3a}$— (in which R$^{3a}$ is hydrogen atom, C$_{1-10}$ alkyl group, C$_{3-7}$ cycloalkyl group, or C$_{1-10}$ alkyl substituted by C$_{3-6}$ cyclo-alkyl group, hydroxy group, C$_{3-6}$ alkoxy group, amino group, cyano group, aryl group, aryl group substituted by C$_{1-6}$ alkoxy, hydroxy or halogen, halogen atom, or nitro group, or may form a heterocyclic ring or a substituted heterocyclic ring together with R$^1$ via the nitrogen atom, wherein said substituent means C$_{1-6}$ alkyl group, hydroxy C$_{1-6}$ alkyl group, C$_{1-6}$ alkoxy C$_{1-6}$ alkyl group, hydroxy group, C$_{1-6}$ alkoxy group, or cyano group), R$^1$ is C$_{1-10}$ alkyl group; C$_{3-7}$ cycloalkyl group; C$_{3-7}$ cycloalkyl substituted by C$_{1-6}$ alkyl;

a group selected from C$_{1-10}$ alkyl group, C$_{3-7}$ cycloalkyl group or C$_{1-6}$ alkyl-substituted C$_{3-7}$ cycloalkyl group, which is substituted by C$_{3-6}$ cycloalkyl group, hydroxy group, C$_{1-6}$ alkoxy group, C$_{1-6}$ alkoxy group substituted by C$_{1-6}$ alkoxy, hydroxy or halogen, amino group, C$_{1-6}$ alkylamino group, cyano group, nitro group, acyl group, carboxyl group, C$_{2-7}$ alkoxycarbonyl group, halogen atom, mercapto group, C$_{1-6}$ alkylthio group, C$_{1-6}$ alkylthio group substituted by C$_{1-6}$ alkoxy, C$_{1-6}$ alkylthio, hydroxy or halogen, aryl group, aryl group substituted by C$_{1-6}$ alkoxy, hydroxy or halogen, or heterocyclic group;

aryl group;

aryl group substituted by

C$_{1-6}$ alkyl group, hydroxy C$_{1-6}$ alkyl group,

C$_{1-6}$ alkoxy C$_{1-6}$ alkyl group, hydroxy group, C$_{1-6}$ alkoxy group, cyano group, amino group, C$_{1-6}$ alkylamino group, C$_{2-7}$ alkoxycarbonyl group, acyl group, nitro group, halogen atom, aryl group, aryl group substituted by C$_{1-6}$ alkoxy, hydroxy or halogen, or heterocyclic group;

heterocyclic group; or heterocyclic group substituted by

C$_{1-6}$ alkyl group, hydroxy C$_{1-6}$ alkyl group, C$_{1-6}$ alkoxy C$_{1-6}$ alkyl group, hydroxy group, C$_{1-6}$ alkoxy group, cyano group, nitro group, halogen atom, amino group, C$_{1-6}$ alkylamino group, C$_{2-7}$ alkoxycarbonyl group, acyl group, aryl group, aryl group substituted by C$_{1-6}$ alkoxy, hydroxy or halogen or heterocyclic group, and R$^2$ is hydrogen atom, or one or more substituents on the benzene ring, and said substituent is the same or different and is hydroxy group, C$_{1-6}$ alkyl group, C$_{1-6}$ alkyl group substituted by hydroxy group, C$_{1-6}$ alkoxy group, carboxyl, C$_{2-7}$ alkoxycarbonyl group or halogen atom, C$_{1-6}$ alkoxy group, C$_{1-6}$ alkoxy group substituted by hydroxy group, C$_{1-6}$ alkoxy group, carboxyl, C$_{2-7}$ alkoxycarbonyl group or halogen atom, C$_{1-6}$ alkanoyl group, C$_{1-6}$ alkanoyl group substituted by hydroxy group, C$_{1-6}$ alkoxy group, carboxyl, C$_{2-7}$ alkoxycarbonyl group or halogen atom, aroyl group, aroyl group substituted by hydroxy group, C$_{1-6}$ alkoxy group, carboxyl, C$_{2-7}$ alkoxycarbonyl group or halogen atom, carboxyl group, C$_{2-7}$ alkoxycarbonyl group, C$_{2-7}$ alkoxycarbonyl group substituted by hydroxy group, C$_{1-6}$ alkoxy group, carboxyl, C$_{2-7}$ alkoxycarbonyl group or halogen atom, amino group, C$_{1-6}$ alkylamino group, di(C$_{1-6}$ alkyl)amino group, carbamoyl group, C$_{1-6}$ alkylcarbamoyl group, di(C$_{1-6}$ alkyl)carbamoyl group, halogen atom, nitro group, or cyano group, or a pharmaceutically acceptable salt thereof.

2. The heterocyclic compound of claim 1, wherein X is sulfur atom, or its pharmaceutically acceptable salt.

3. The heterocyclic compound of claim 1, wherein X is oxygen atom, or its pharmaceutically acceptable salt.

4. The heterocyclic compound of claim 1, wherein X is —NH—, or its pharmaceutically acceptable salt.

5. The heterocyclic compound of claim 1, wherein X is —$NR^{3a}$— in which $R^{3a}$ means $C_{1-6}$ alkyl group or substituted $C_{1-6}$ alkyl substituted by $C_{3-6}$ cycloalkyl group, hydroxy group, $C_{1-6}$ alkoxy group, amino group, cyano group, aryl group, aryl group substituted by $C_{1-6}$ alkoxy, hydroxy or halogen, halogen atom, or nitro group, or its pharmaceutically acceptable salt.

6. The heterocyclic compound of claim 1, wherein $R^{3a}$ forms a heterocyclic ring or a substituted heterocyclic ring together with $R^1$ via the nitrogen atom, or its pharmaceutically acceptable salt.

7. The heterocyclic compound of claim 1, wherein $R^1$ means $C_{1-6}$ alkyl group or substituted $C_{1-6}$ alkoxy, $C_{1-6}$ alkylthio, $C_{2-7}$ alkoxycarbonyl, hydroxy, halogen atom, cyano, amino, cyclohexyl, trifluoromethyl, pyridyl, phenyl, methoxyphenyl, hydroxyphenyl, halophenyl or thienyl, or its pharmaceutically acceptable salt.

8. The heterocyclic compound of claim 1, wherein $R^1$ means $C_{1-6}$ substituted alkyl group and said substituent is hydroxyl, or its pharmaceutically acceptable salt.

9. 6-Amino-9-benzyl-8-hydroxy-2-[(2-hydroxyethyl)thio]purine or its pharmaceutically acceptable salt.

10. 6-Amino-9-(4-fluorobenzyl)-8-hydroxy-2-(2-methoxyethoxy)purine or its pharmaceutically acceptable salt.

11. 6-Amino-9-benzyl-8-hydroxy-2-(2-methoxyethoxy)purine or its pharmaceutically acceptable salt.

12. A pharmaceutical composition comprising a heterocyclic compound or its pharmaceutically acceptable salt of claim 1, as an active ingredient.

13. A method for inducing interferons in a patient having virus infected disease, cancer or allergic disease by administering the heterocyclic compound of claim 1, or its pharmaceutically acceptable salt to the patient in an amount effective to induce interferons.

* * * * *